(12) United States Patent
Xing et al.

(10) Patent No.: US 8,580,755 B2
(45) Date of Patent: Nov. 12, 2013

(54) METHODS AND COMPOSITIONS FOR TREATING INFLAMMATORY CONDITIONS

(75) Inventors: Lianping Xing, Webster, NY (US); Brendan F. Boyce, Pittsford, NY (US); Edward M. Schwarz, Rochester, NY (US)

(73) Assignee: University of Rochester, Rochester, NY (US)

( * ) Notice: Subject to any disclaimer, the term of this patent is extended or adjusted under 35 U.S.C. 154(b) by 42 days.

(21) Appl. No.: 12/389,193

(22) Filed: Feb. 19, 2009

(65) Prior Publication Data
US 2009/0232829 A1 Sep. 17, 2009

Related U.S. Application Data

(60) Provisional application No. 61/029,799, filed on Feb. 19, 2008.

(51) Int. Cl.
*A61K 48/00* (2006.01)
*A01N 63/00* (2006.01)
*A01N 65/00* (2009.01)

(52) U.S. Cl.
USPC .................. 514/44 R; 424/93.1; 424/93.2

(58) Field of Classification Search
None
See application file for complete search history.

(56) References Cited

U.S. PATENT DOCUMENTS

| | | |
|---|---|---|
| 2002/0032313 A1 | 3/2002 | Ferrara et al. |
| 2002/0164667 A1 | 11/2002 | Alitalo et al. |
| 2004/0120950 A1 | 6/2004 | Alitalo et al. |
| 2004/0247597 A1 | 12/2004 | Carmeliet et al. |
| 2007/0082848 A1 | 4/2007 | Alitalo et al. |
| 2007/0135489 A1 | 6/2007 | Huth et al. |
| 2007/0224137 A1 | 9/2007 | Delmar |
| 2007/0253952 A1 | 11/2007 | Alvarez Vallina et al. |
| 2007/0258984 A1 | 11/2007 | Fyfe et al. |
| 2008/0003228 A1 | 1/2008 | Le et al. |

OTHER PUBLICATIONS

Friedmann (1997) Overcoming the obstacles to gene therapy. Scientific American, Jun. 1997, pp. 97-101.*
Orkin and Motulsky (1995) Report and recommendations of the panel to assess the NIH investment in research on gene therapy. pp. 1-40.*
Verma et al. (1997) Gene therapy—promises, problems and prospects. Nature 389: 239-242.*
Huggenberger et al. (2010) Stimulation of lymphangiogenesis via VEGFR-3 inhibits chronic skin inflammation. J. Exp. Med. 207(10): 2255-2269.*
Brent (2009) Inflammatory arthritis: an overview for primary care physicians. Postgraduate Medicine 121(2): 148-162.*
Ghivizzani et al. (2008) Perspectives on the use of gene therapy for chronic joint diseases. Current Gene Therapy 8(4): 273-286.*
Wauke et al., "Expression and Localization of Vascular Endothelial Growh Factor-C in Rheumatoid Arthitis Synovial Tissue," J Rheumatol 29:34-38 (2002).
Cha et al., "Tumor Necrosis Factor-Alpha Induces Vascular Endothelial Growth Factor-C Expression in Rheumatoid Synoviocytes," J. Rheumatol 34:16-19 (2007).
Huh et al., "The Role of Popliteal Lymph Nodes in Differentiating Rheumatoid Arthritis from Osteoarthritis by Using CE 3D FSPGR MR Imaging: Relationship of the Inflamed Synovial Volume," Korean J Radiol 6:117-124 (2005).
Olszewski et al., "Lymph Draining from Foot Joints in Rheumatoid Arthritis Provides Insight into Local Cytokine and Chemokine Production and Transport to Lymph Nodes," Arthritis Rheum 44:541-549 (2001).
Ristimaki et al., "Proinflammatory Cytokines Regulate Expression of the Lymphatic Endothelial Mitogen Vascular Endothelial Growth Factor-C," J Biol Chem 273:8413-8418 (1998).
Kajiya et al., "An Important Role of Lymphatic Vessels in the Control of UVB-Induced Edema Formation and Inflammation," J Invest Dermatol 126:919-921 (2006).
Baluk et al., "Pathogenesis of Persistent Lymphatic Vessel Hyperplasia in Chronic Airway Inflammation," J Clin. Invest 115:247-257 (2005).
Yoon et al., "VEGF-C Gene Therapy Augments Postnatal Lymphangiogenesis and Ameliorates Secondary Lymphedema," J Clin Invest 111:717-725 (2003).
Xing et al., "Lymphangiogenesis, Myeloid Cells and Inflammation," Expert Rev Clin Immunol 4(5):599-613 (2008).
Zhang et al., "Increased Lymphangiogenesis in Joints of Mice with Inflammatory Arthritis," Arthritis Res Ther 9(6):R118 (2007).
Paavonen et al., "Vascular Endothelial Growth Factors C and D and their VEGFR-2 and 3 Receptors in Blood and Lymphatic Vessels in Healthy and Arthritic Synovium," J Rheumatol 29(1):39-45 (2002).
Polzer et al., "Tumour Necrosis Factor Blockade Increases Lymphangiogenesis in Murine and Human Arthritic Joints," Ann Rheum Dis 67(11):1610-6 (2008).
Joukov et al., "A Recombinant Mutant Vascular Endothelial Growth Factor-C That Has Lost Vascular Endothelial Growth Factor Receptor-2 Binding, Activation, and Vascular Permeability Activities," J. Biol Chem 273(12):6599-6602 (1998).
Suzuki et al., "Roles of Vascular Endothelial Growth Factor Receptor 3 Signaling in Differentiation of Mouse Embryonic Stem Cell-derived Vascular Progenitor Cells into Endothelial Cells," Blood 105(6):2372-2379 (2005).
Kajiya et al., "Activation of the VEGFR-3 Pathway by VEGF-C Attenuates UVB-Induced Edema Formation and Skin Inflammation by Promoting Lymphangiogenesis," J. Invest Dermatol. 129:1292-1298 (2009).

* cited by examiner

*Primary Examiner* — Anne-Marie Falk
(74) *Attorney, Agent, or Firm* — LeClairRyan, a Professional Corporation

(57) ABSTRACT

The present invention is directed to methods of treating an inflammatory condition in a patient. This method includes providing a therapeutic agent that is a vascular endothelial growth factor receptor-3 (VEGFR-3) agonist or a nucleic acid molecule encoding a VEGFR-3 agonist. The present invention is further directed to pharmaceutical compositions and therapeutic systems for treating an inflammatory condition.

26 Claims, 38 Drawing Sheets

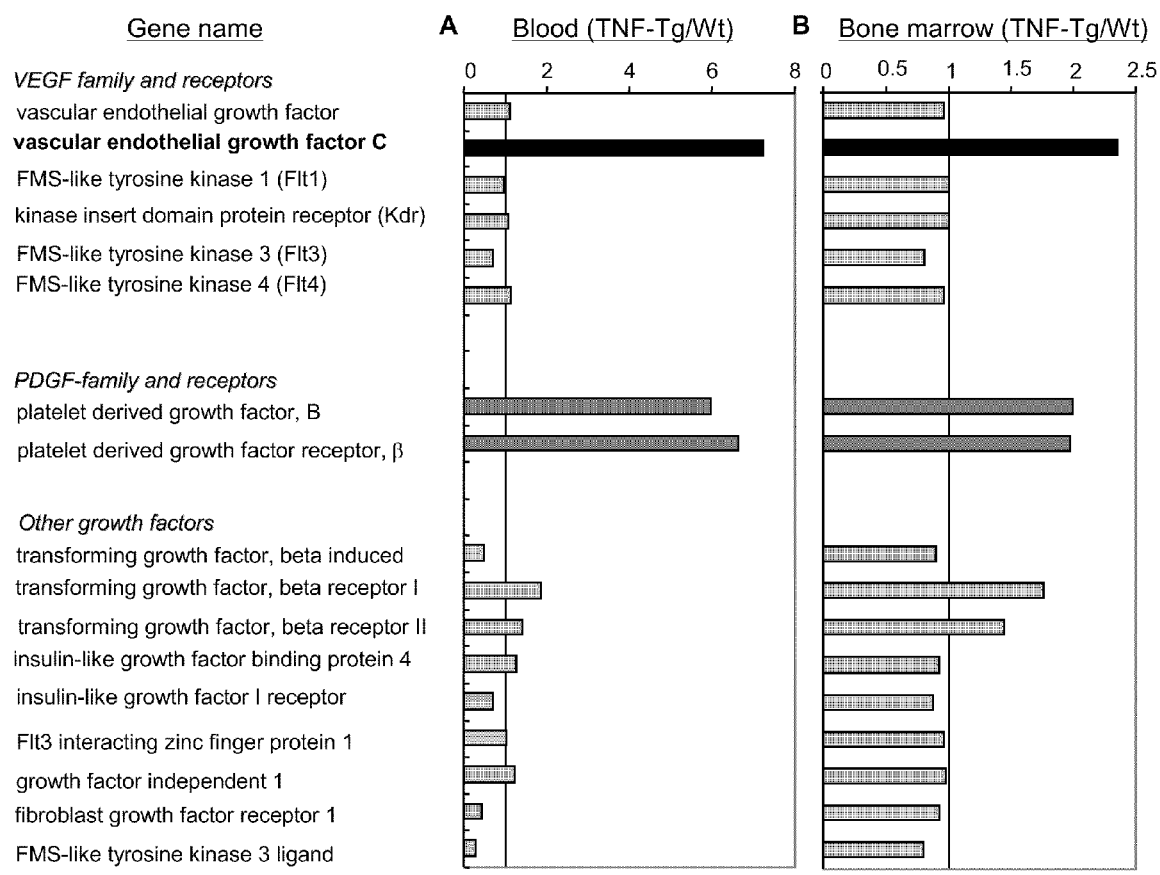
Figures 1A-B

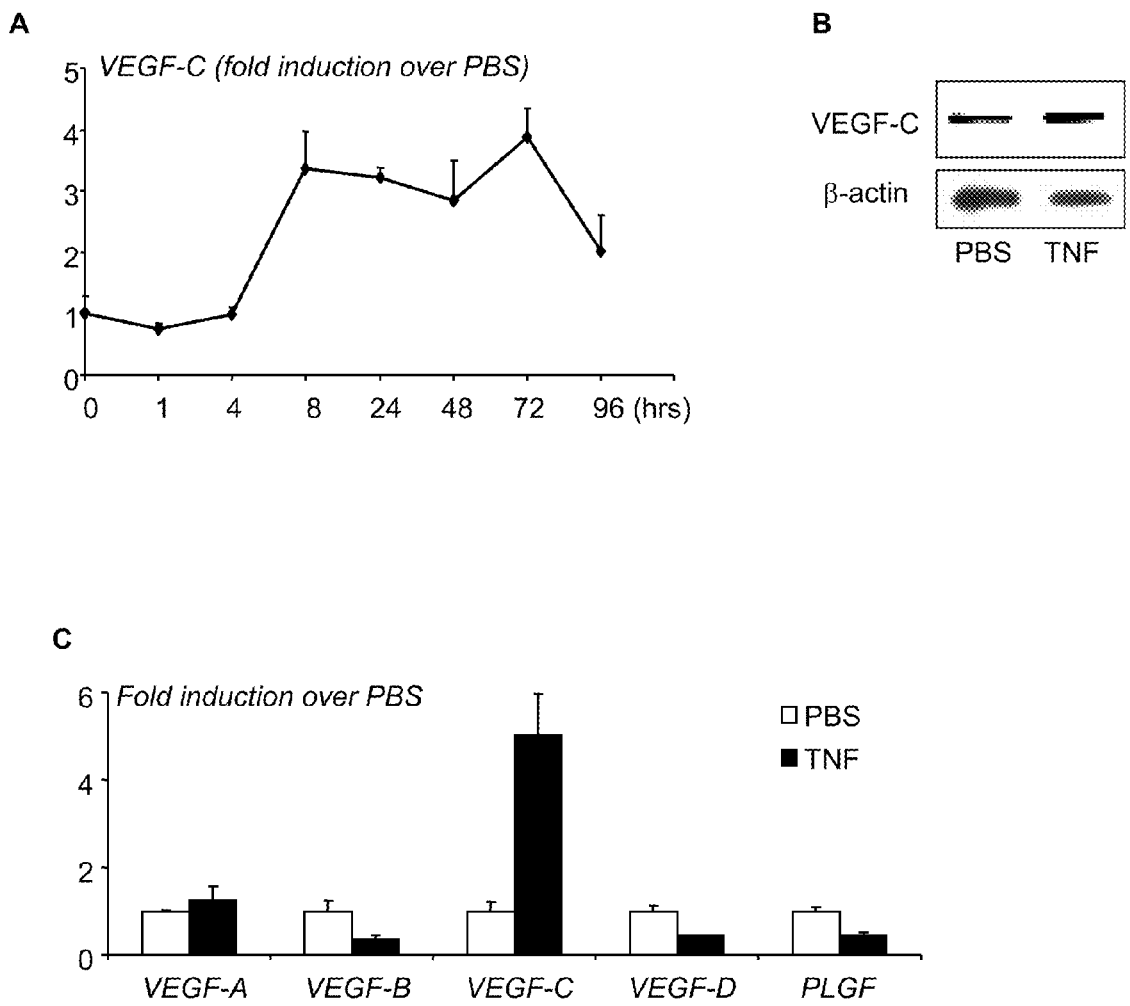
Figures 2A-C

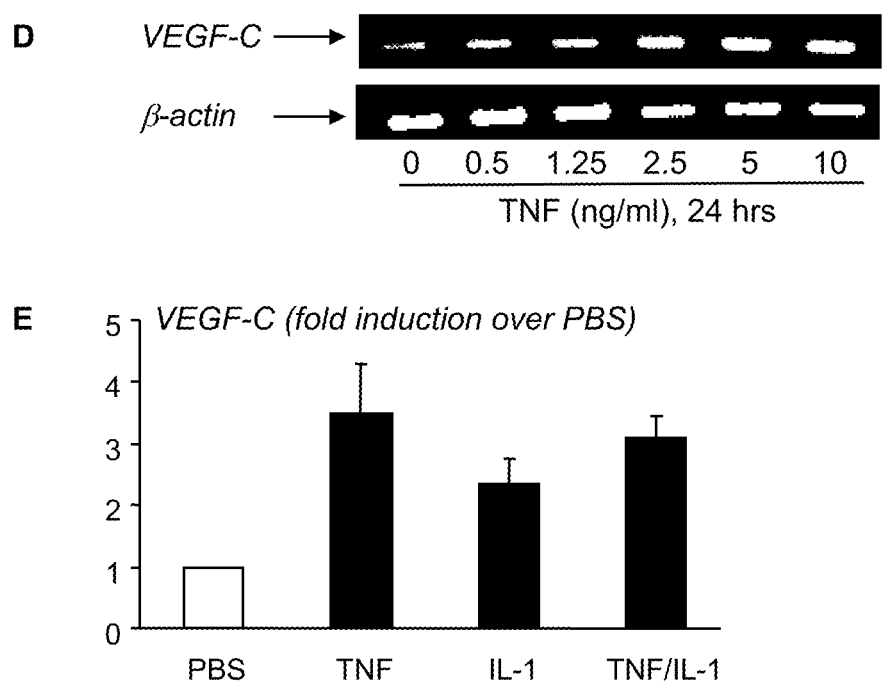
Figures 2D-E

A
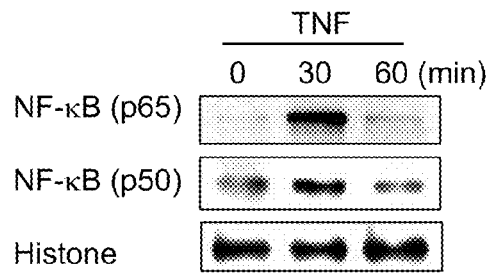
B
NF-κB binding sequence:
Wild type VEGF-C:    5'-GCCCCAGGGGGGTCCCCGGGAGG-3' (SEQ ID NO:17)
Mutant    VEGF-C:    5'-GCCCCAG*GGGATTCTCC*GGGAGG-3' (SEQ ID NO:18)
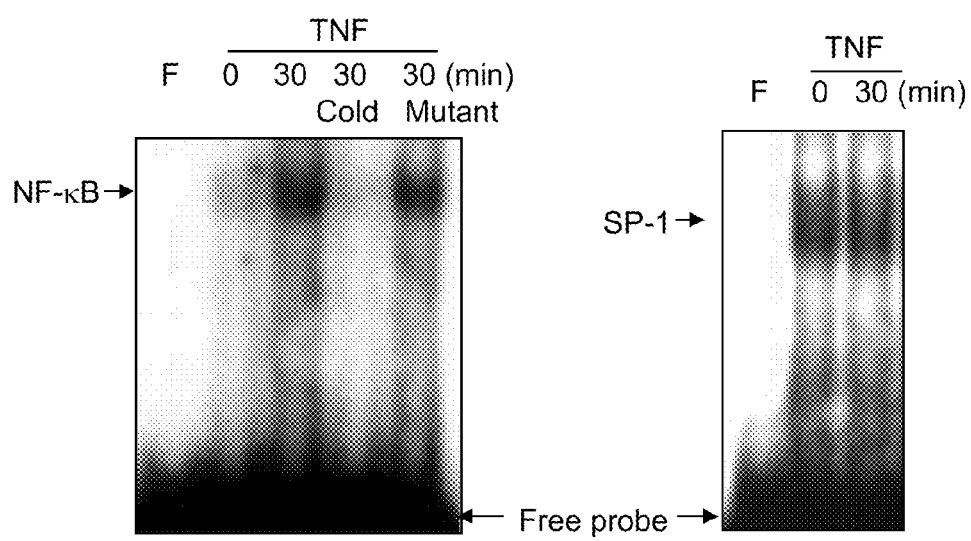
Figures 3A-B

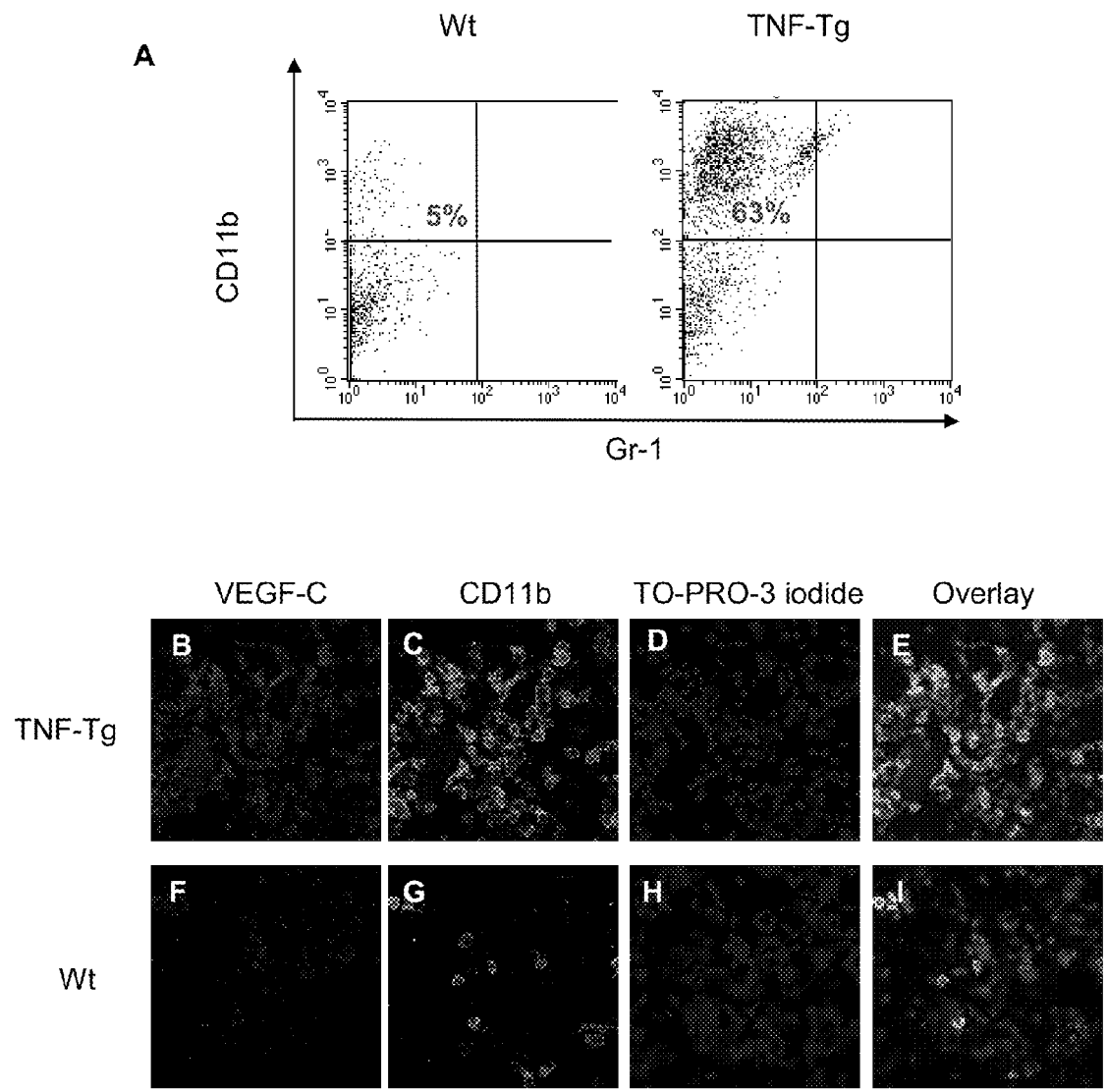
Figures 4A-I

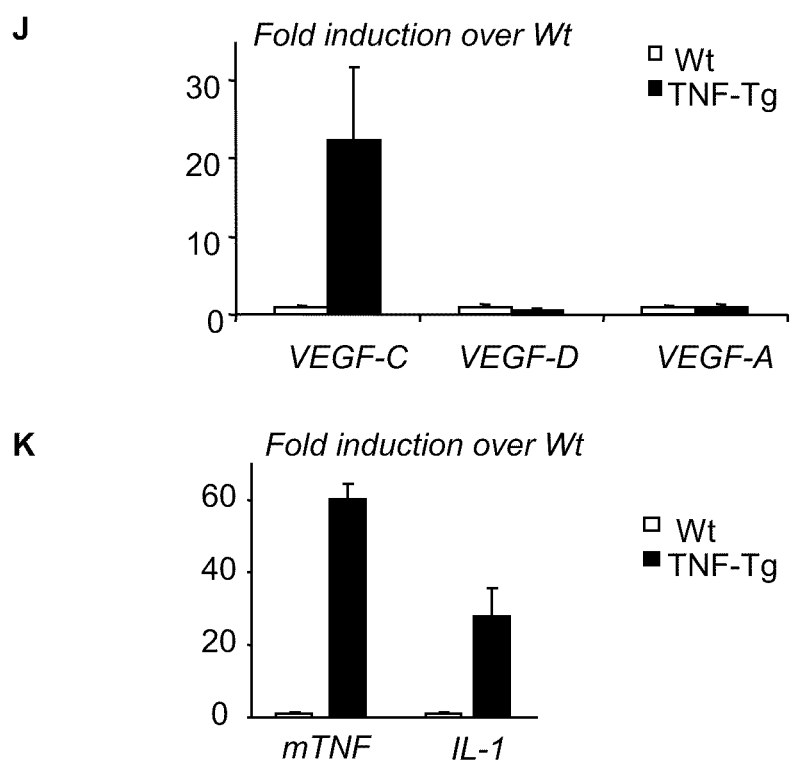
Figures 4J-K

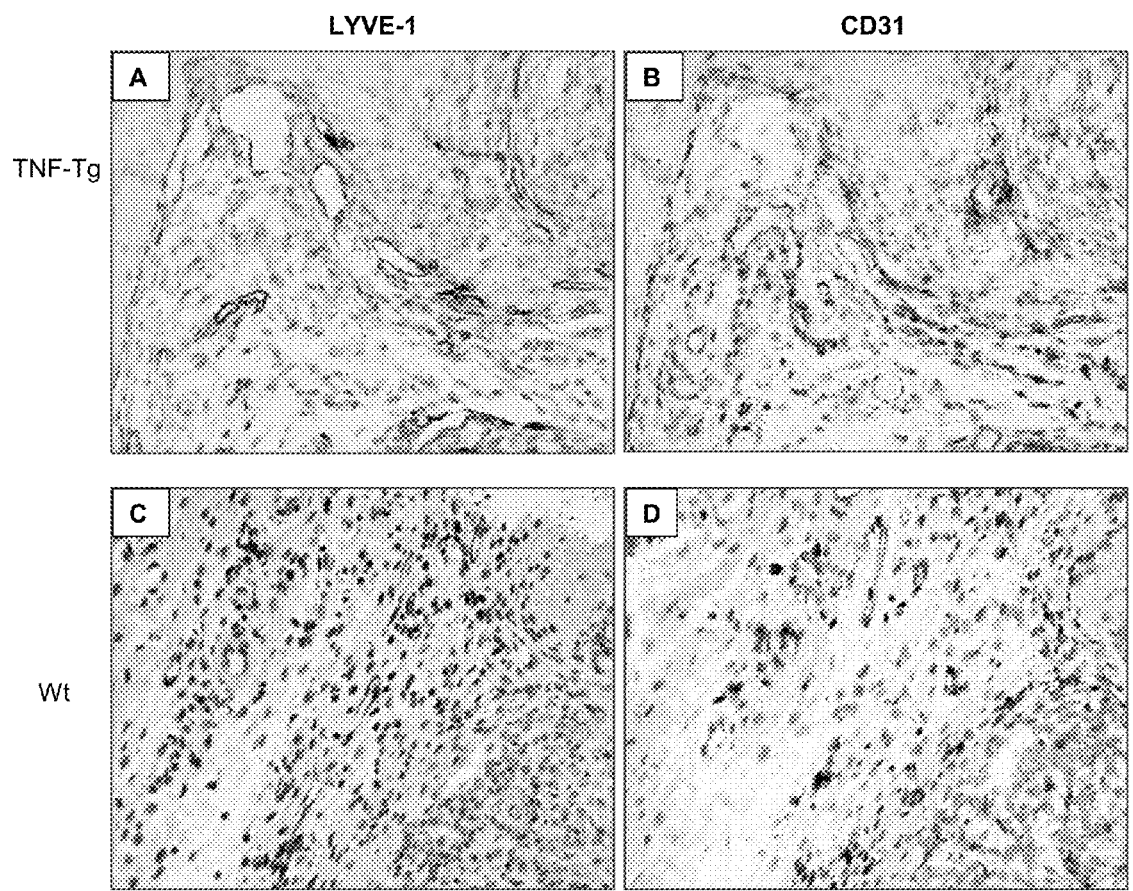
Figures 5A-D

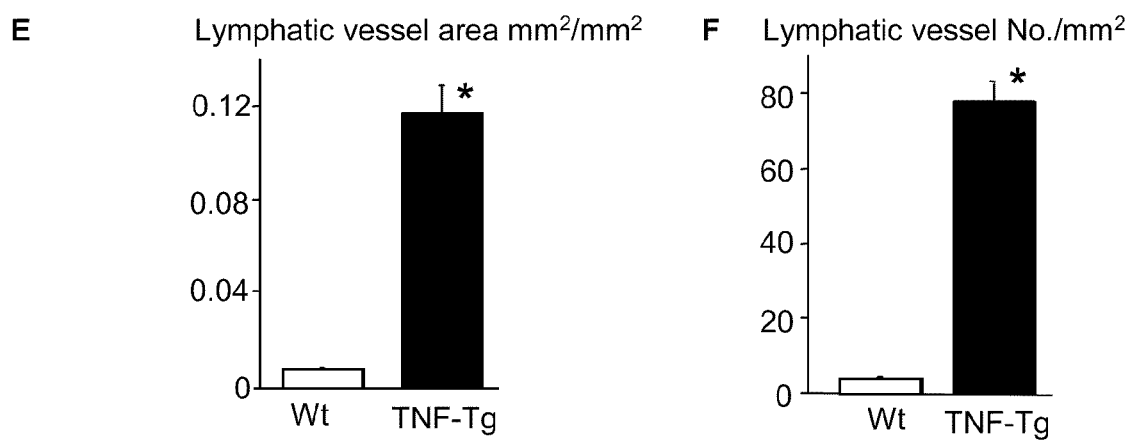
Figures 5E-F

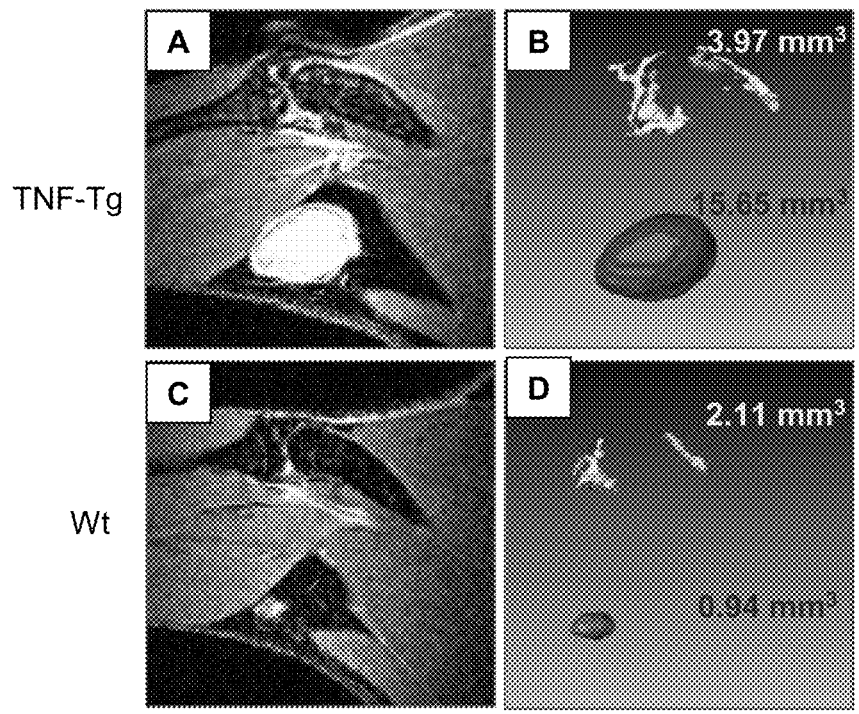
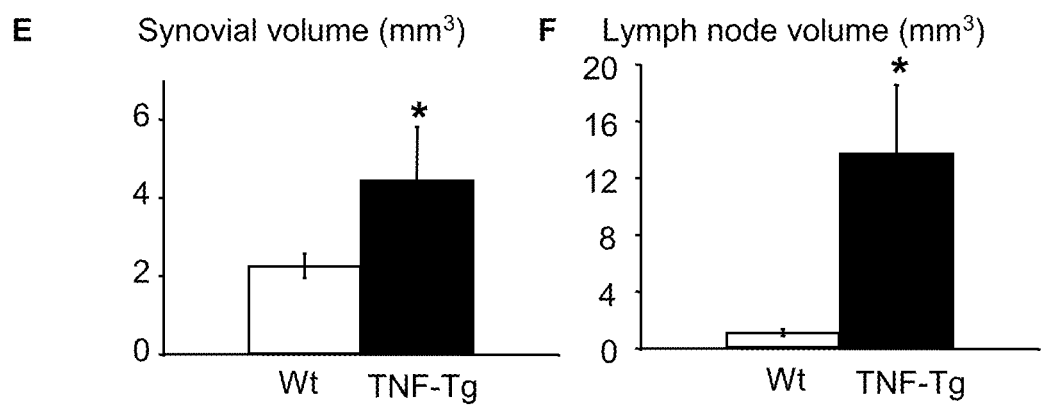
Figures 6A-F

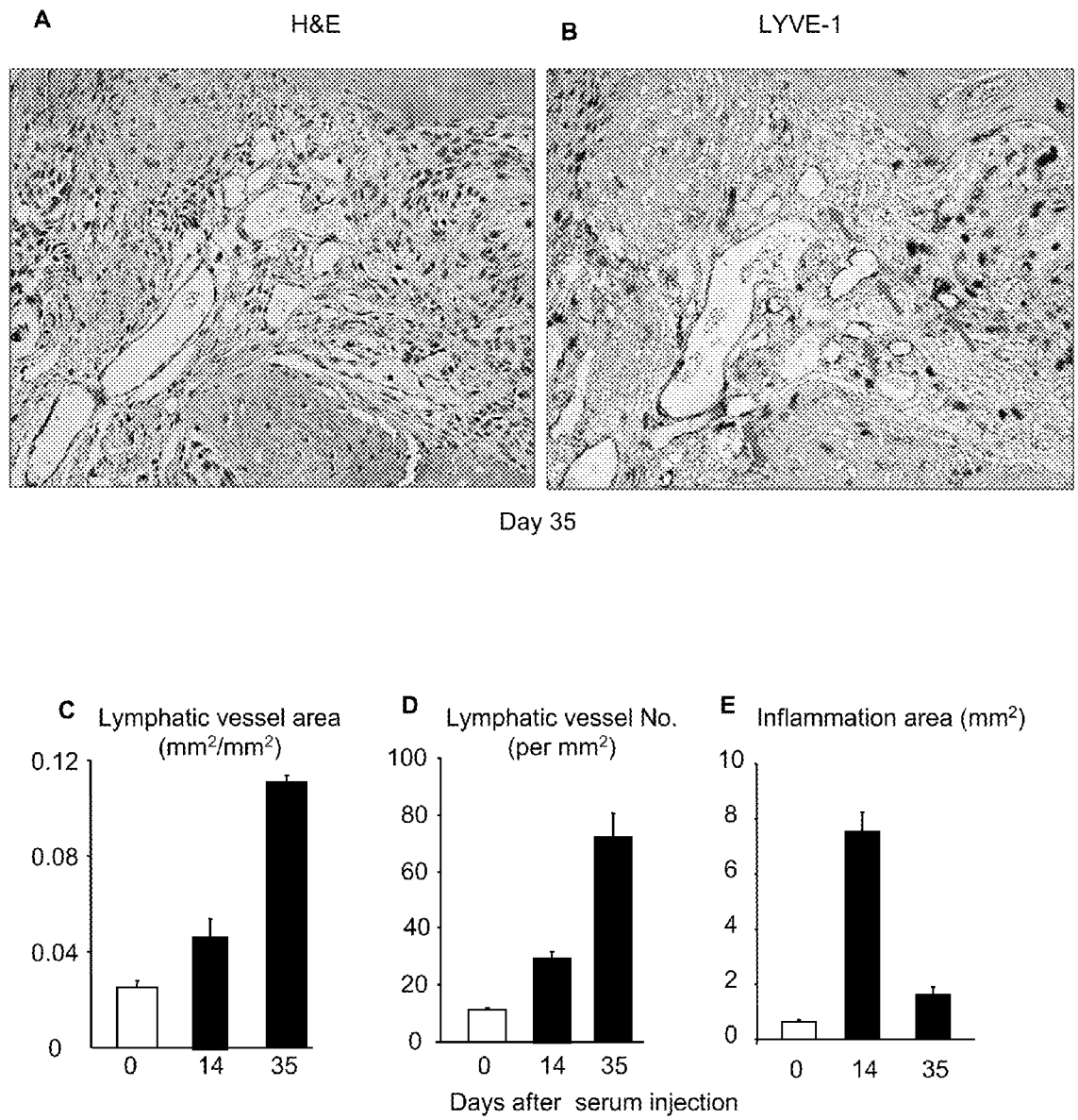
Figures 7A-E

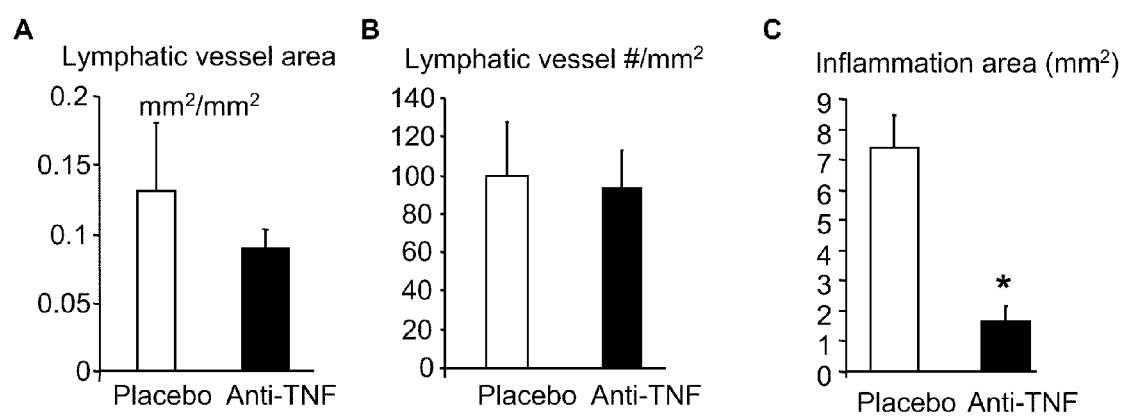
Figures 8A-C

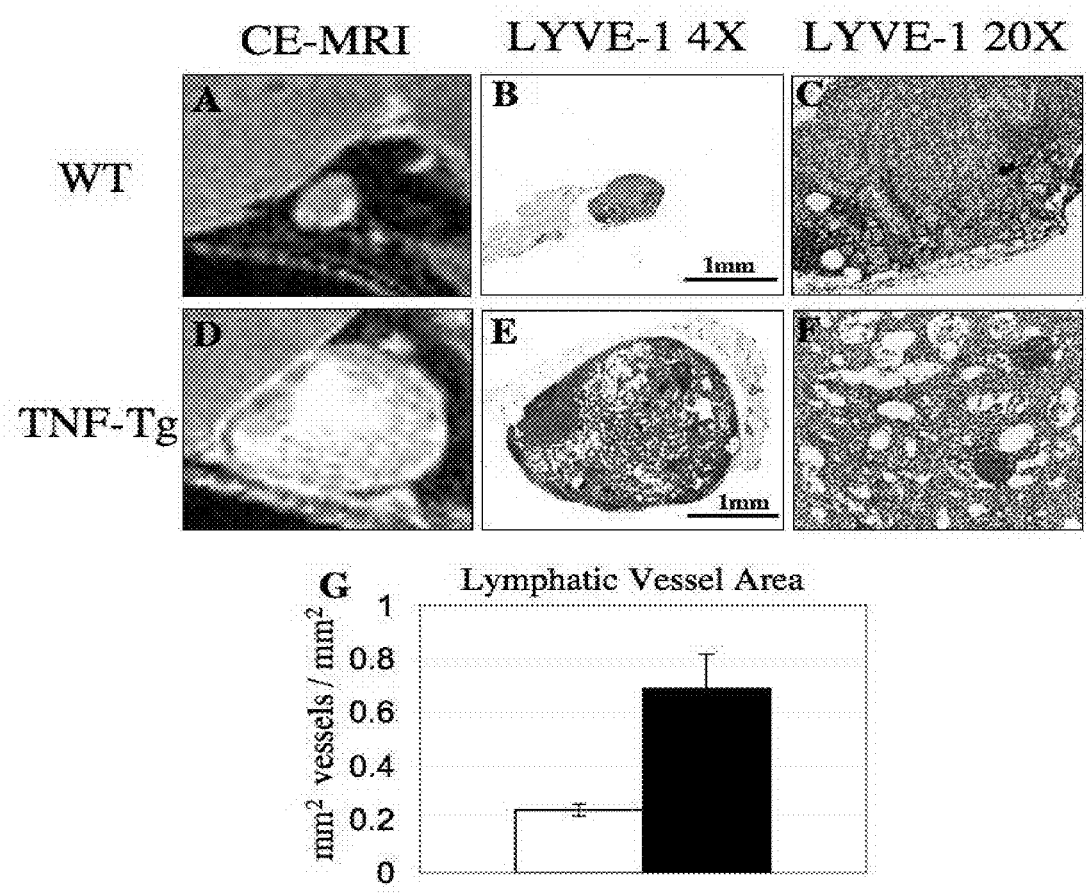
Figures 9A-G

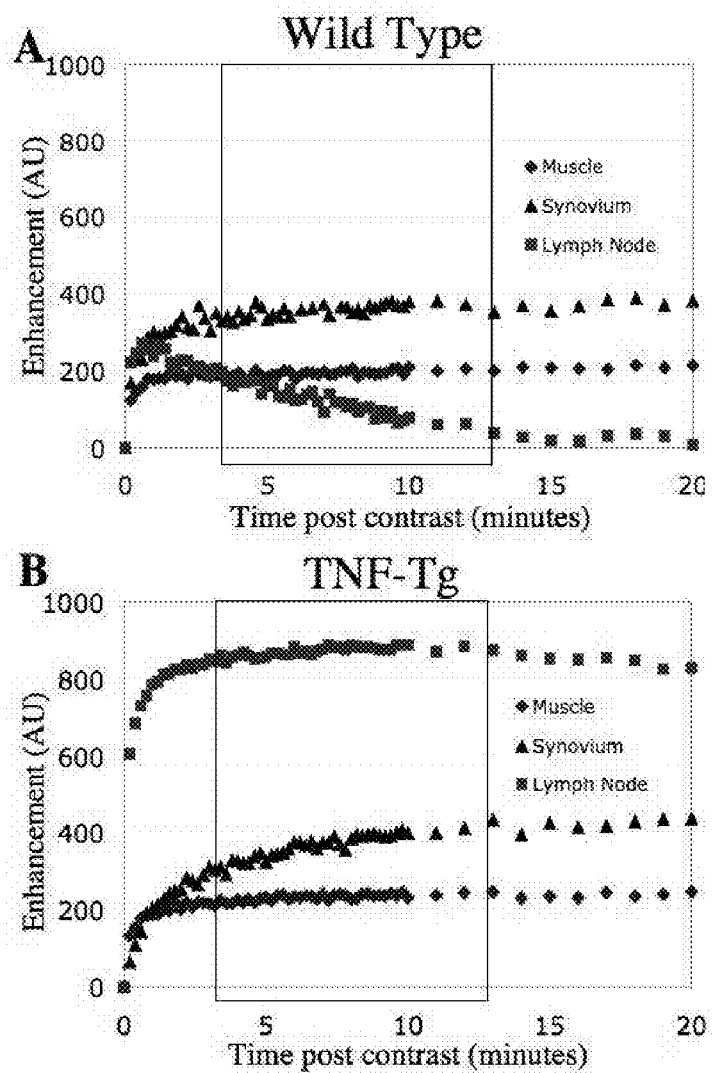
Figures 10A-B

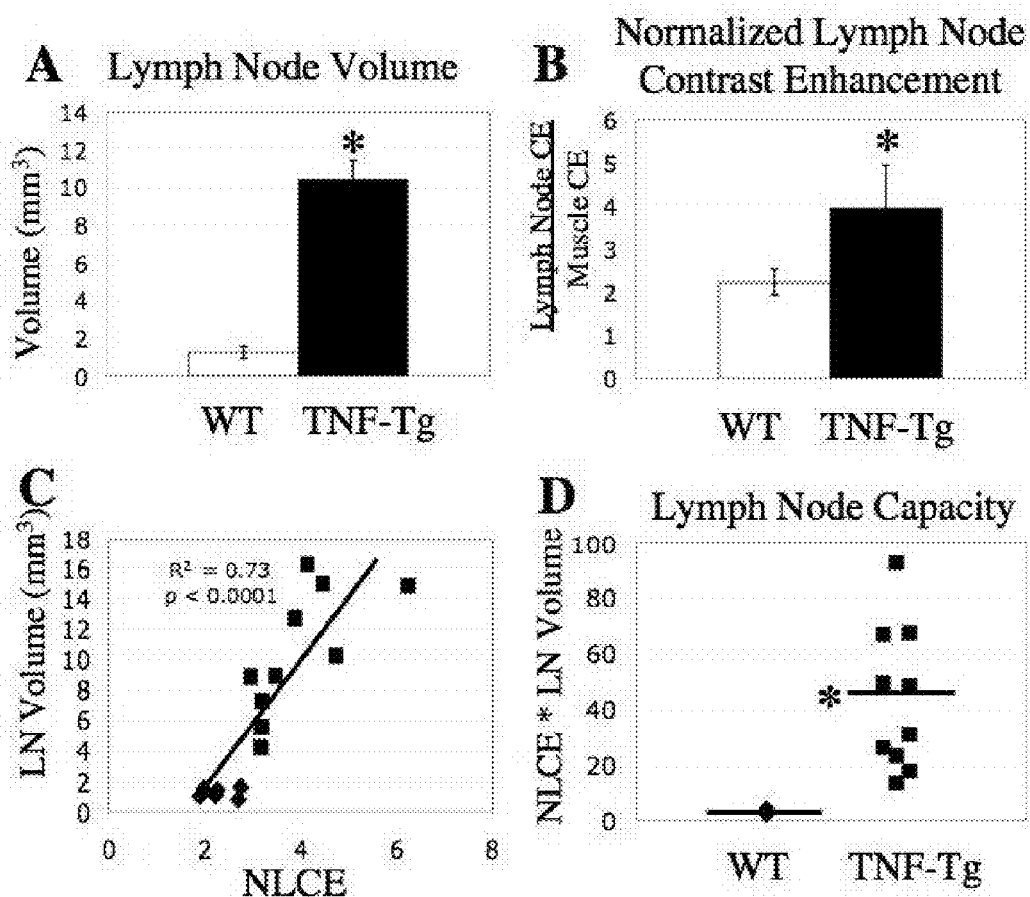
Figures 11A-D

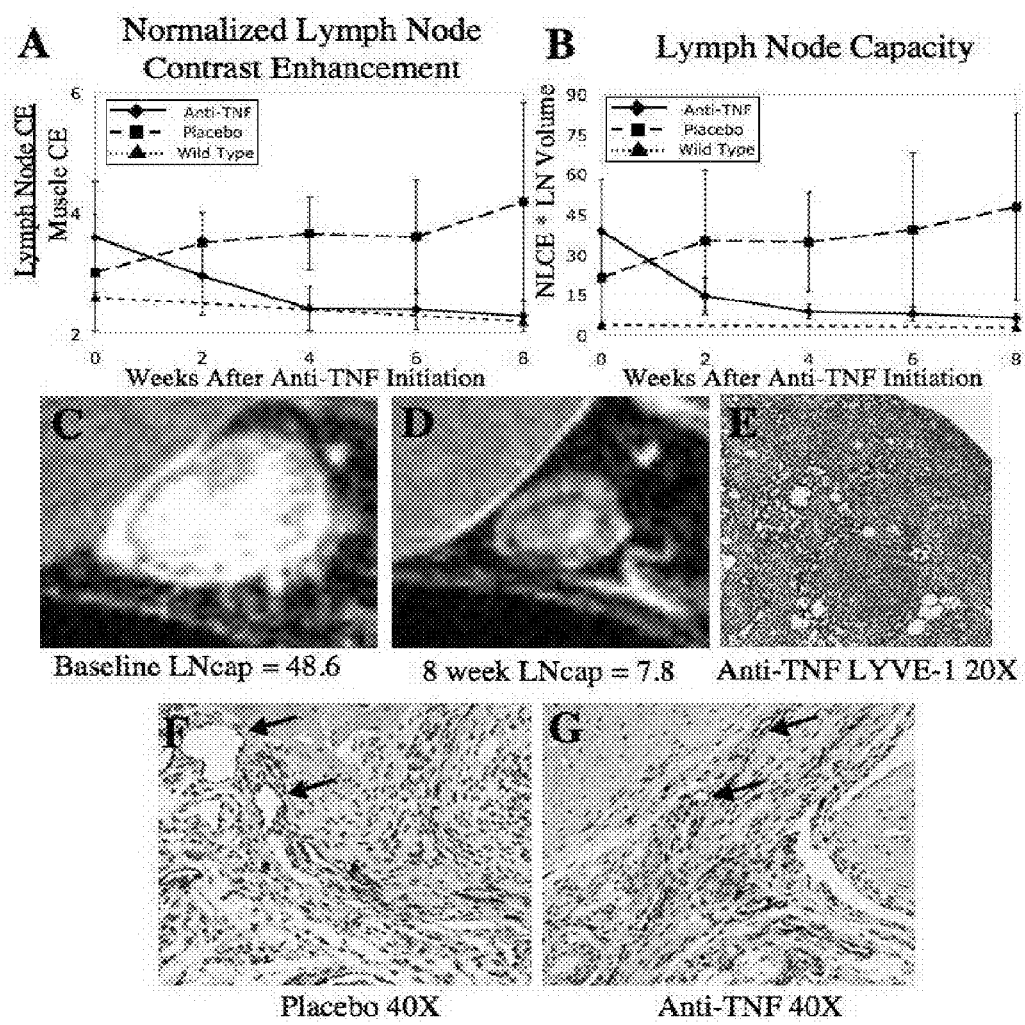
Figures 12A-G

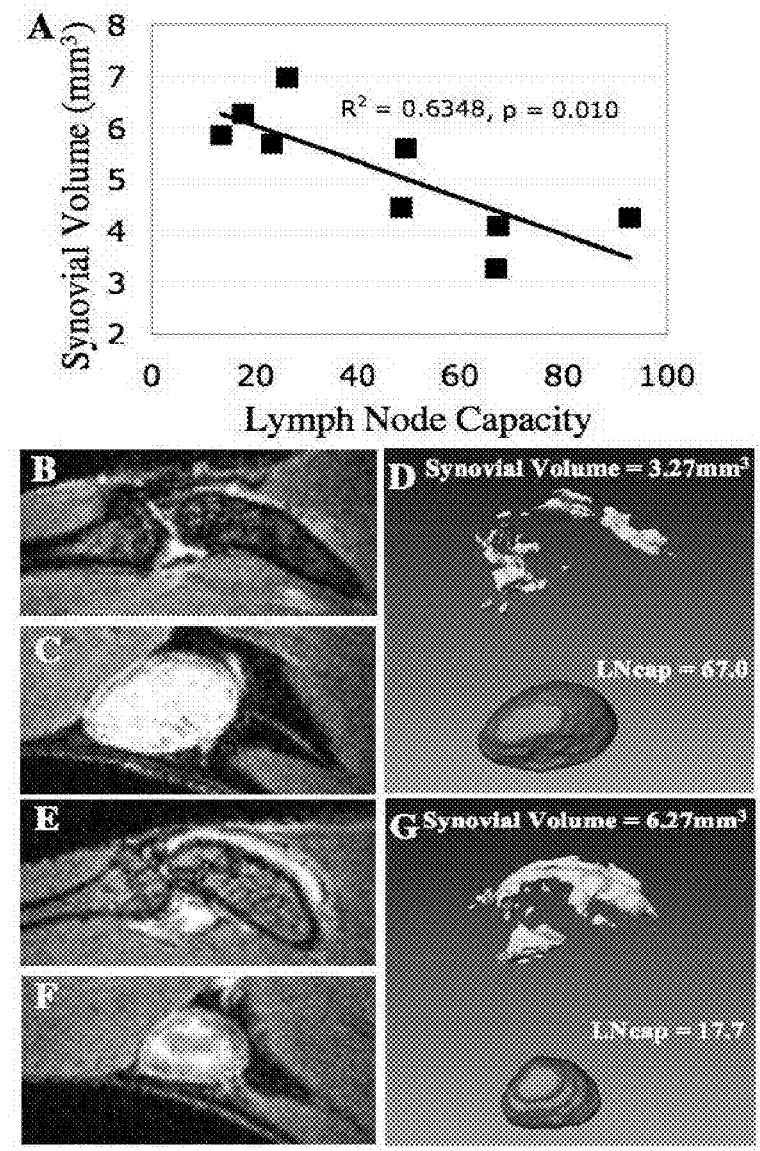
Figures 13A-G

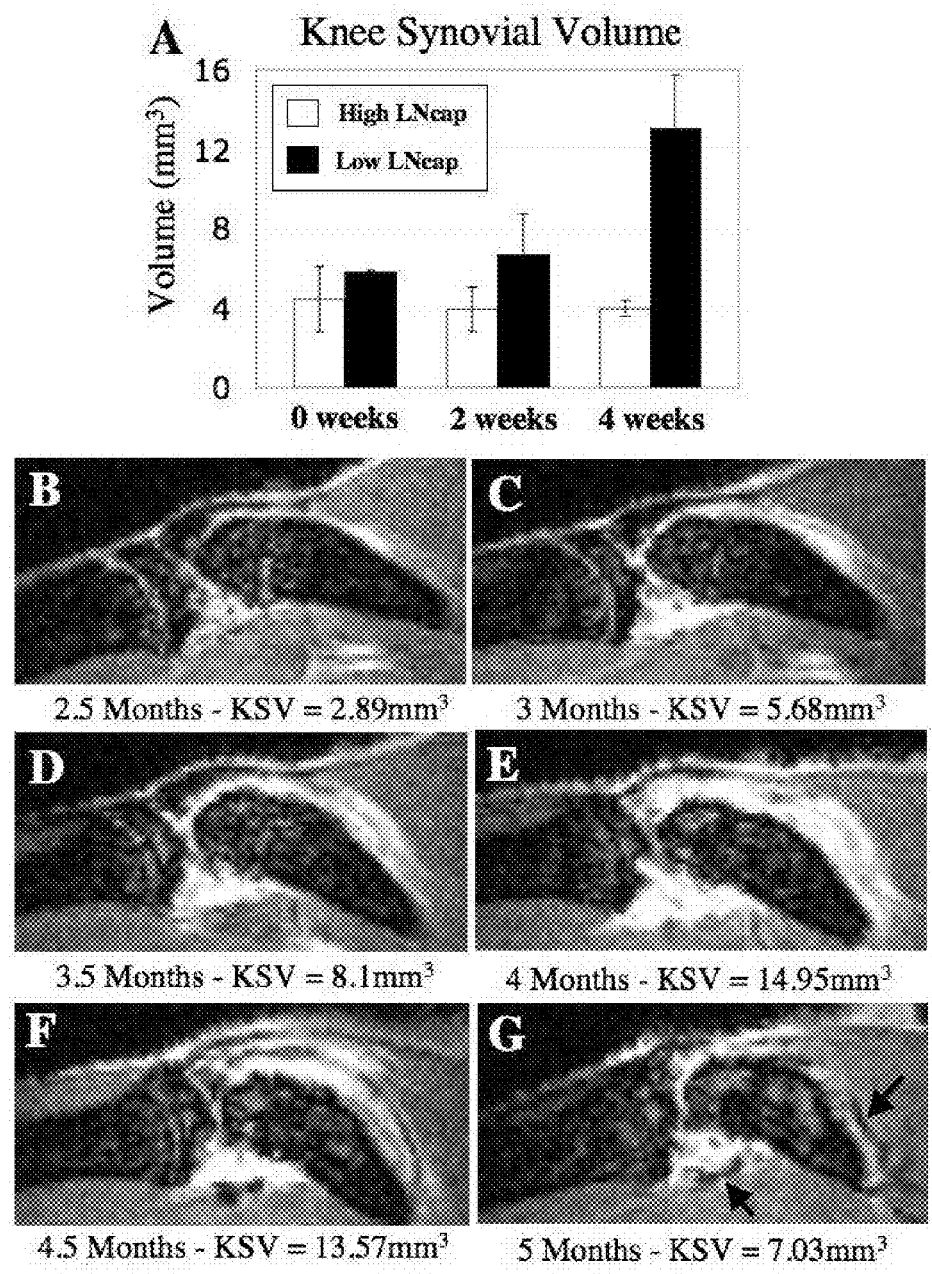
Figures 14A-G

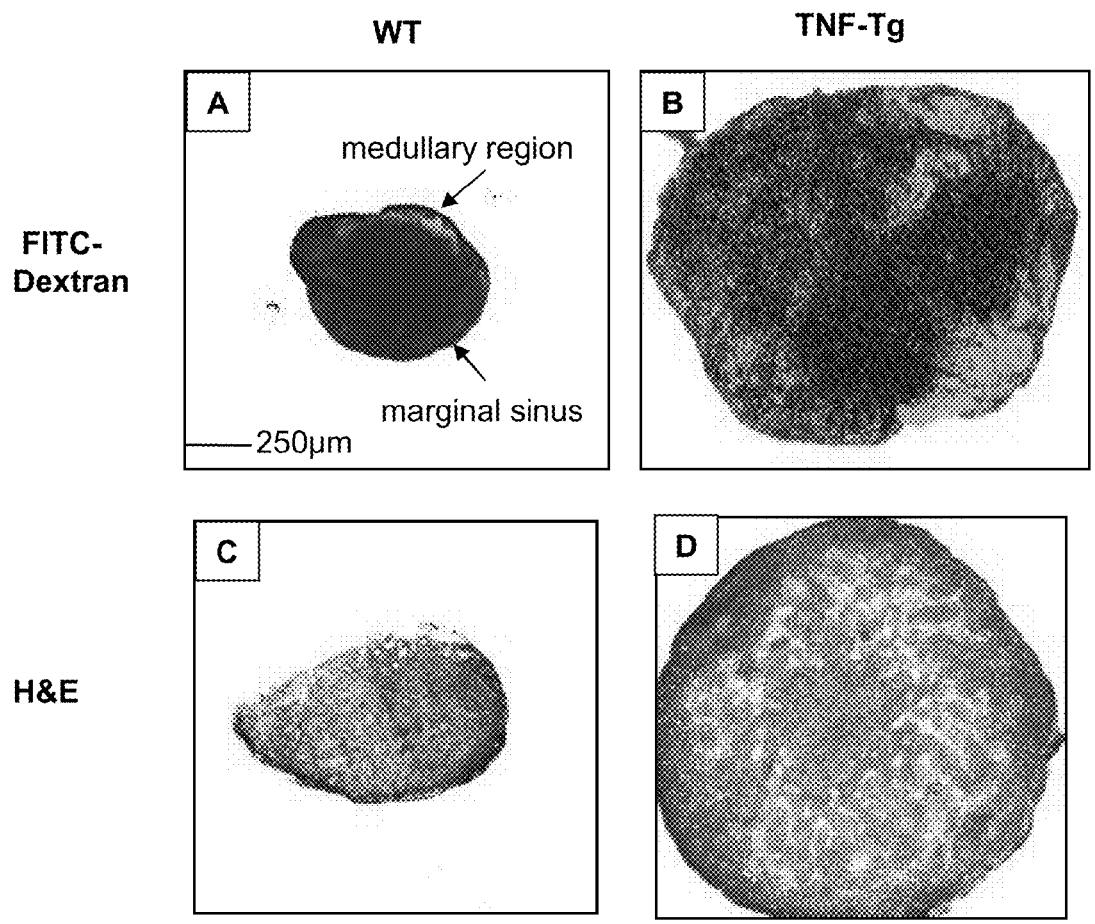
Figures 16A-D

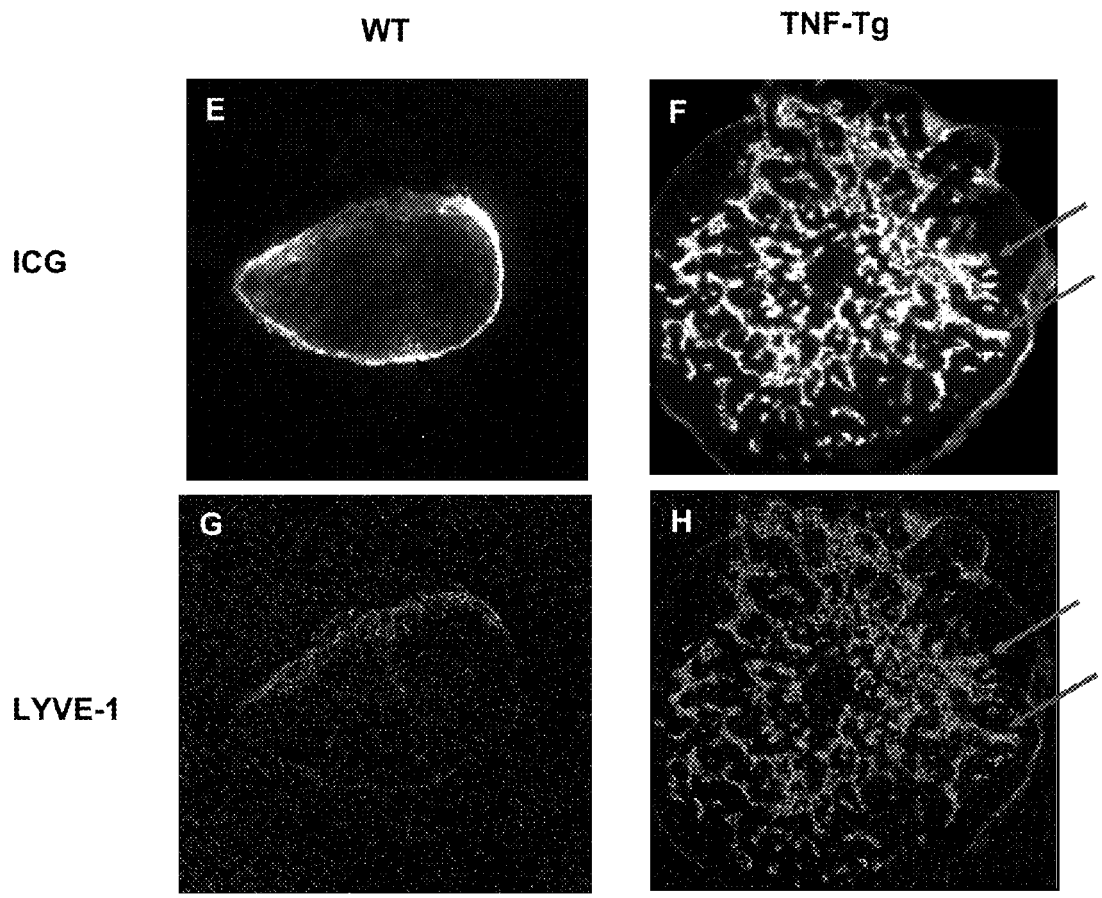
Figures 16E-H

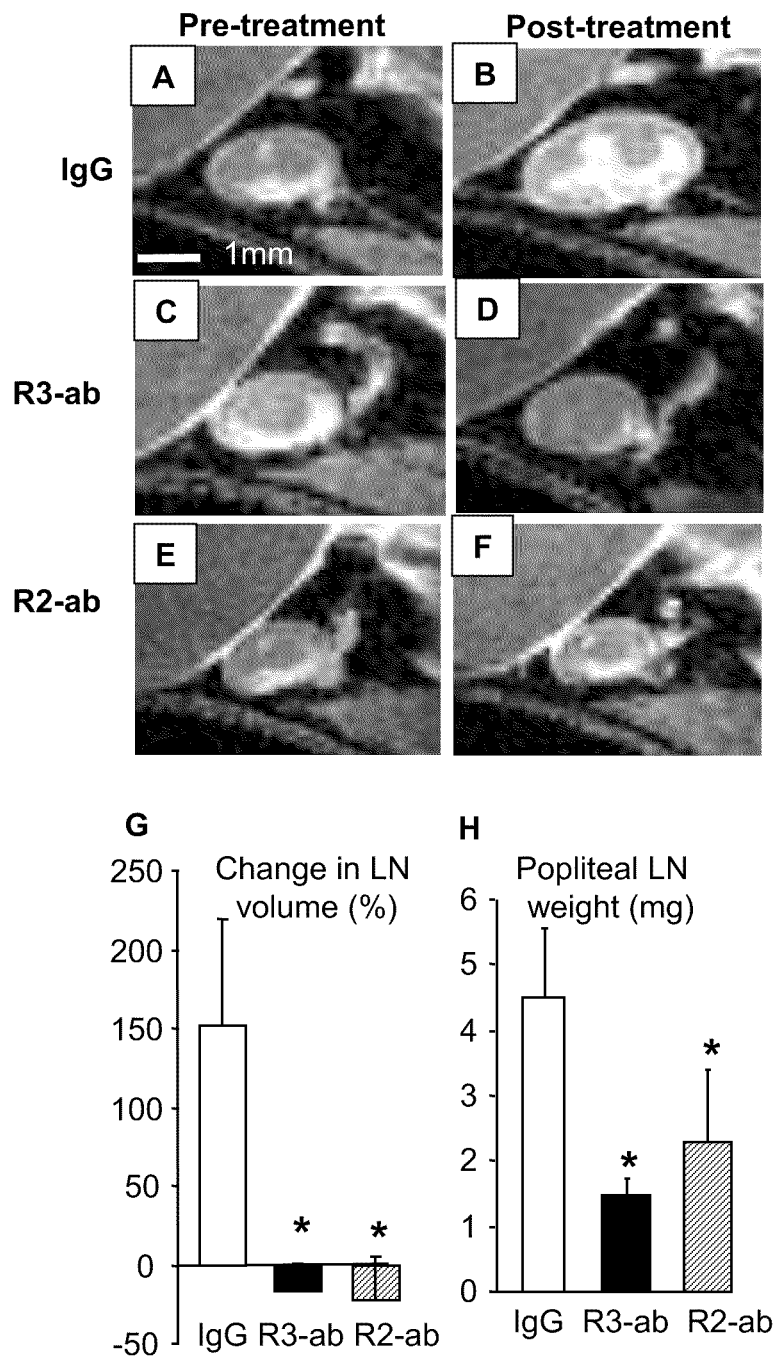
Figures 18A-H

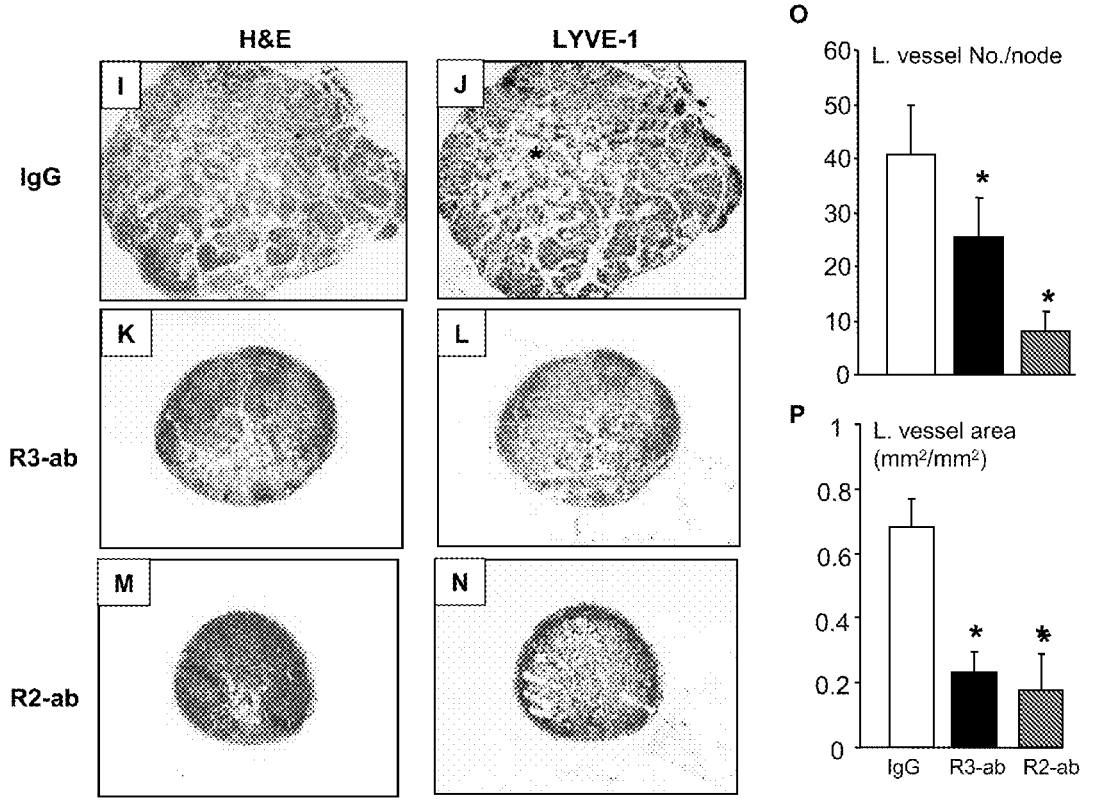
Figures 18I-P

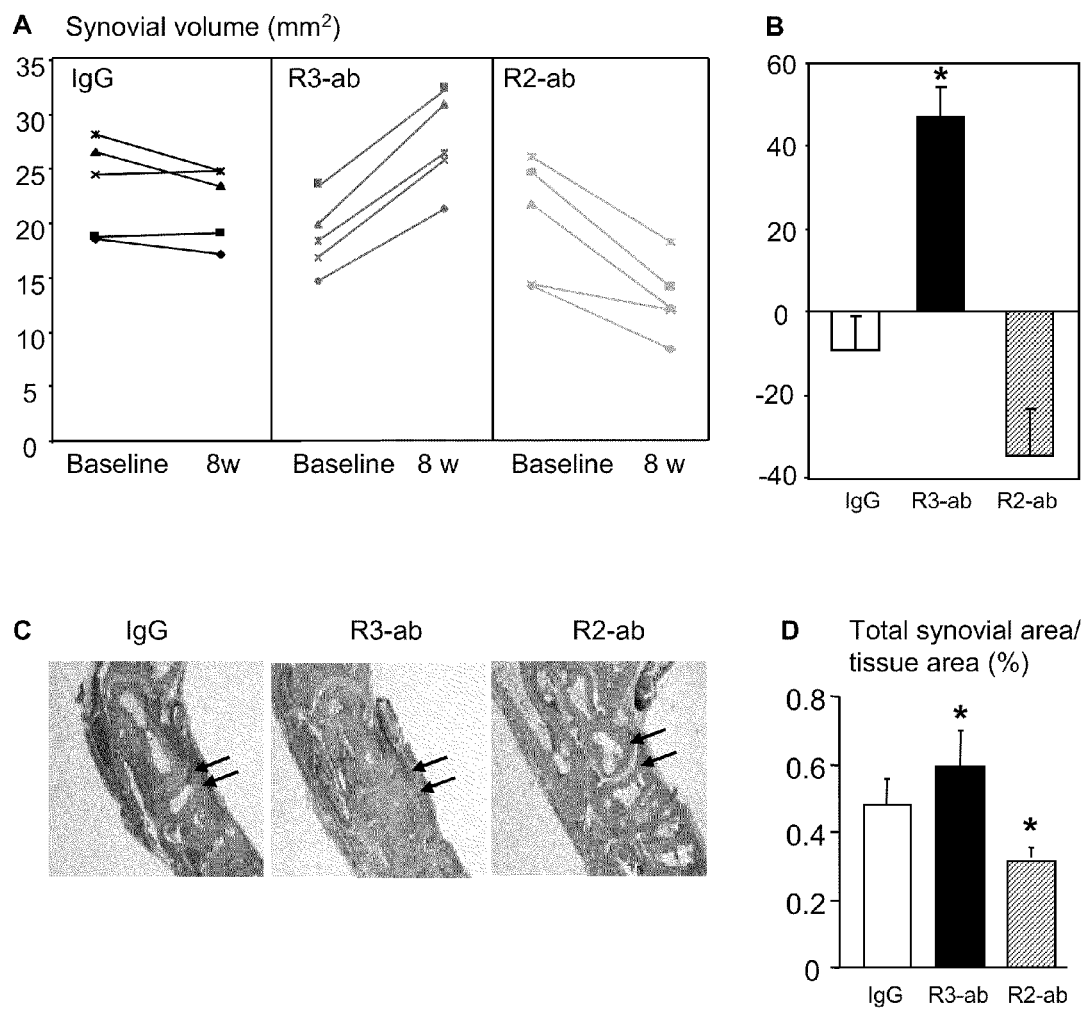
Figures 19A-D

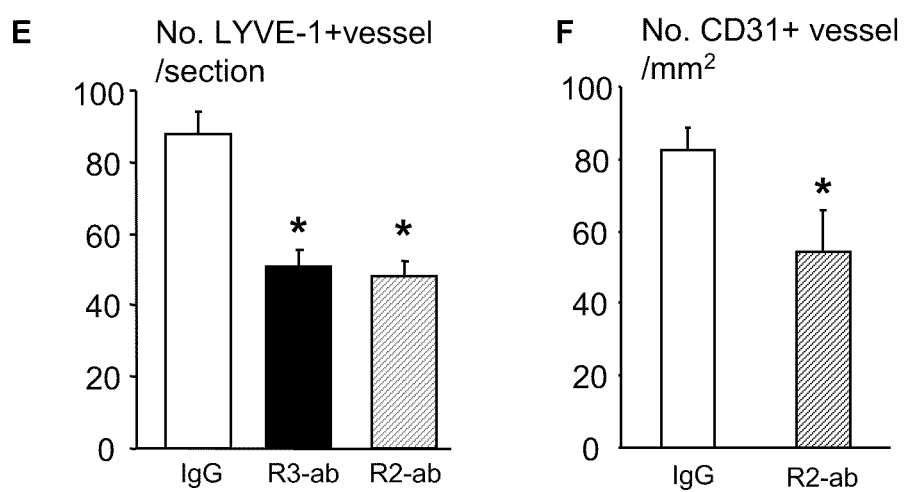
Figures 19E-F

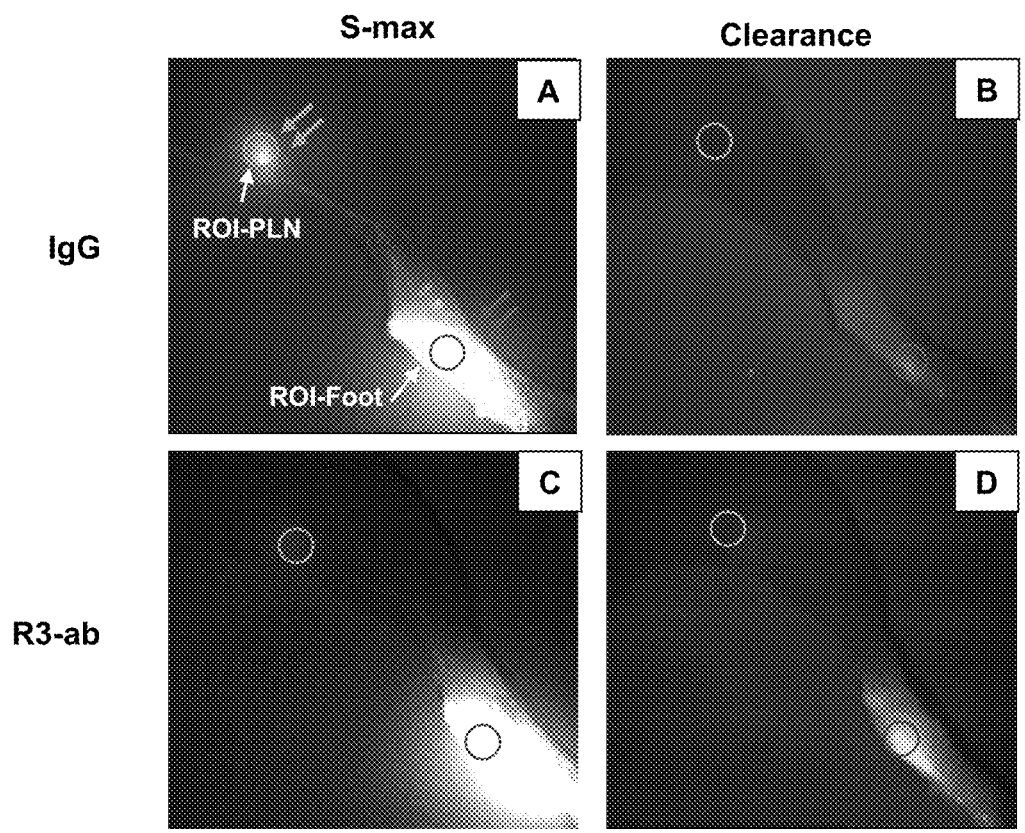
Figures 20A-D

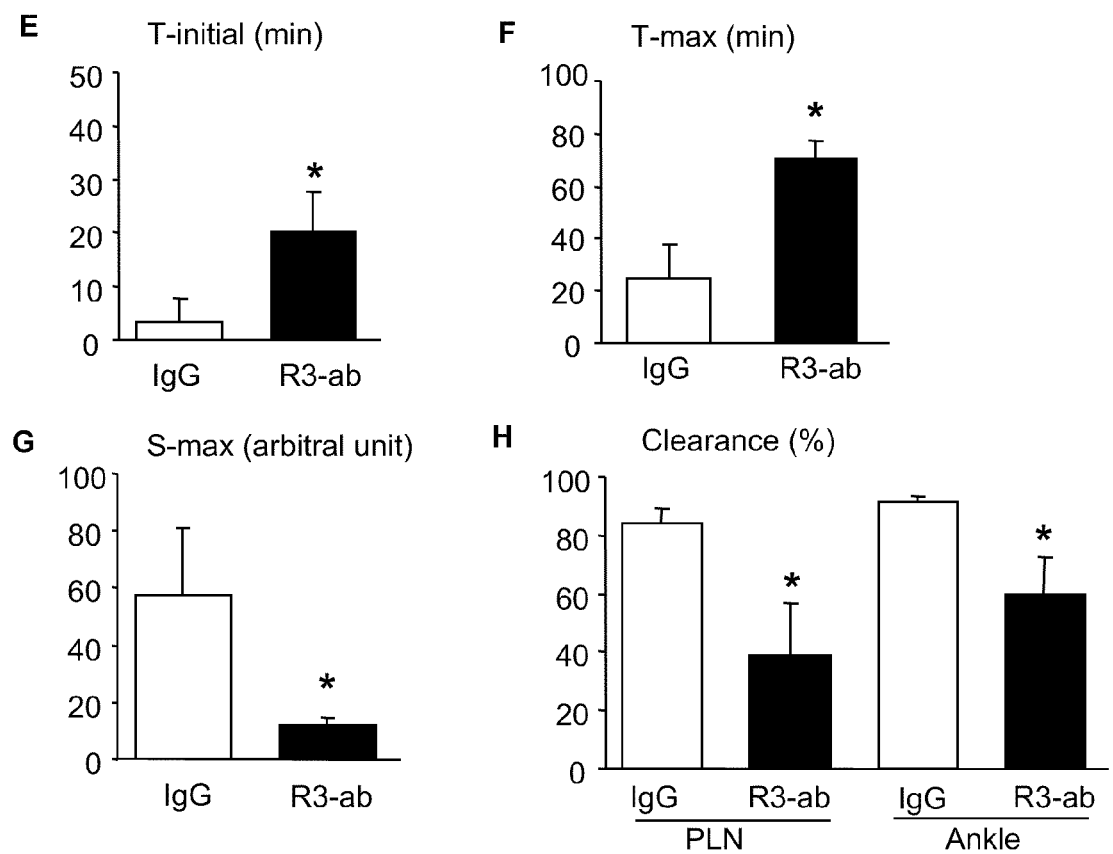
Figures 20E-H

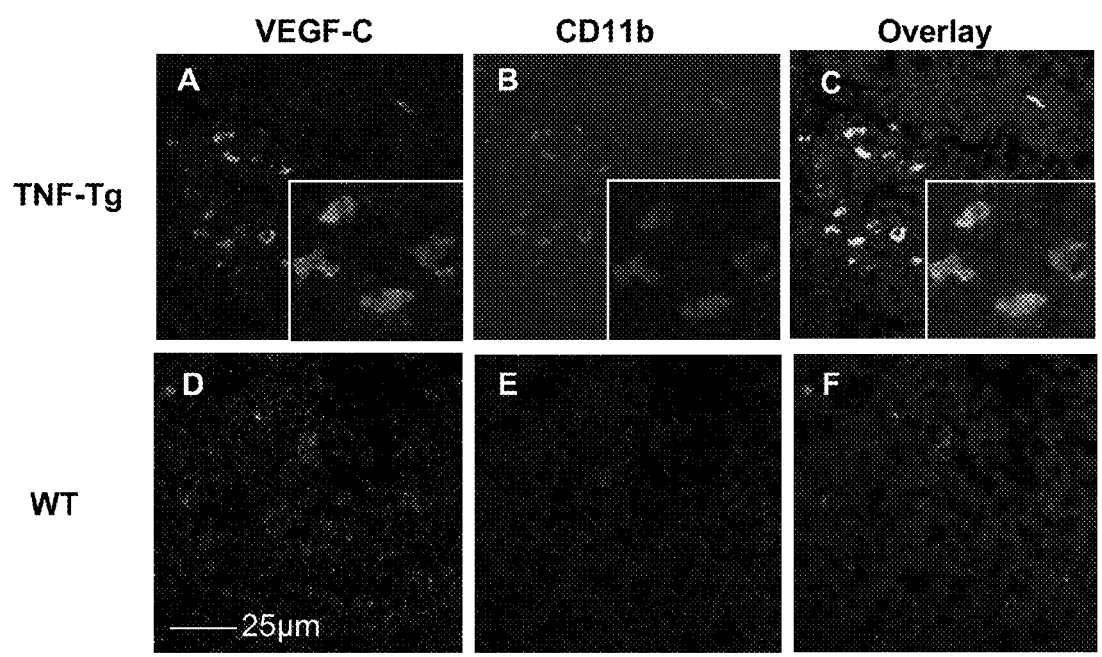
Figures 21A-F

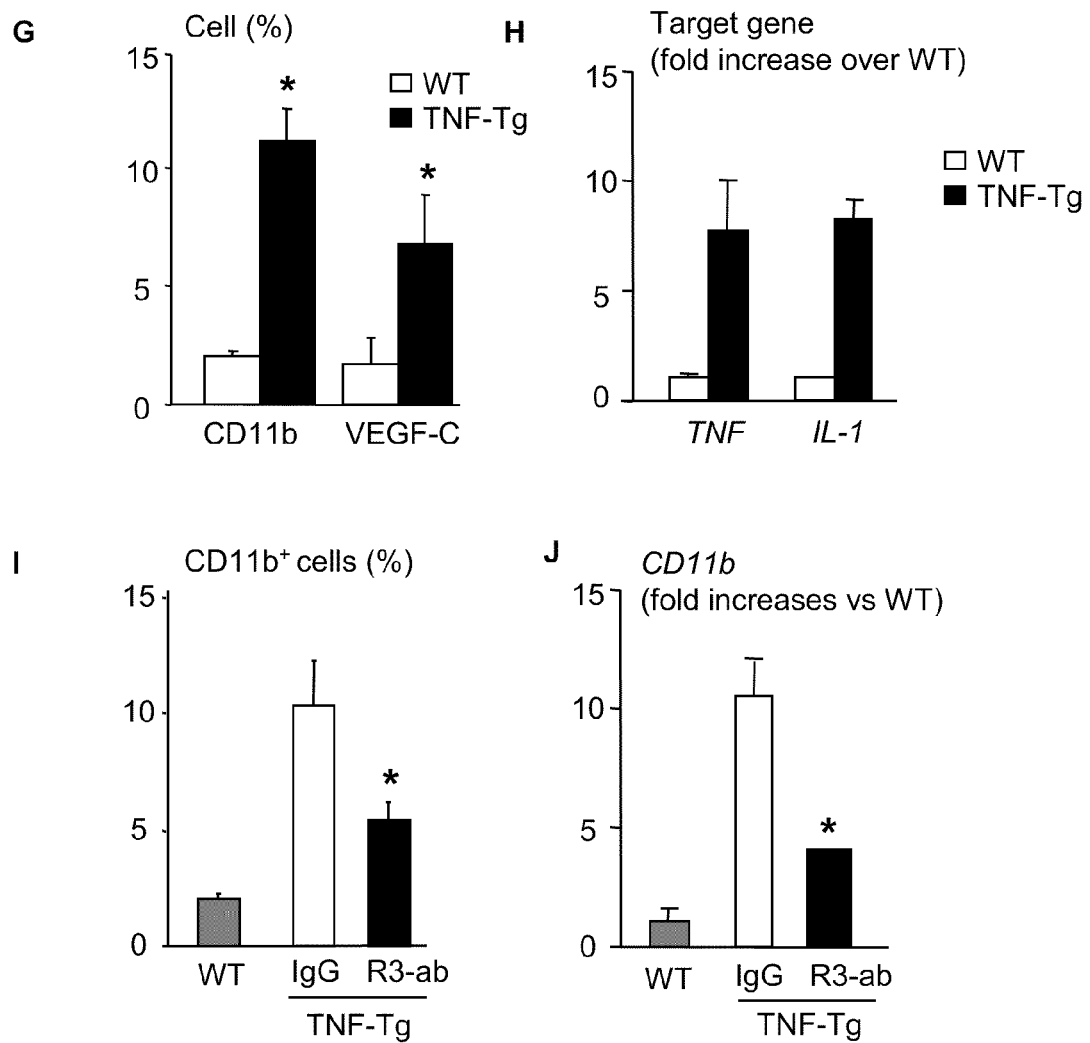
Figures 21G-J

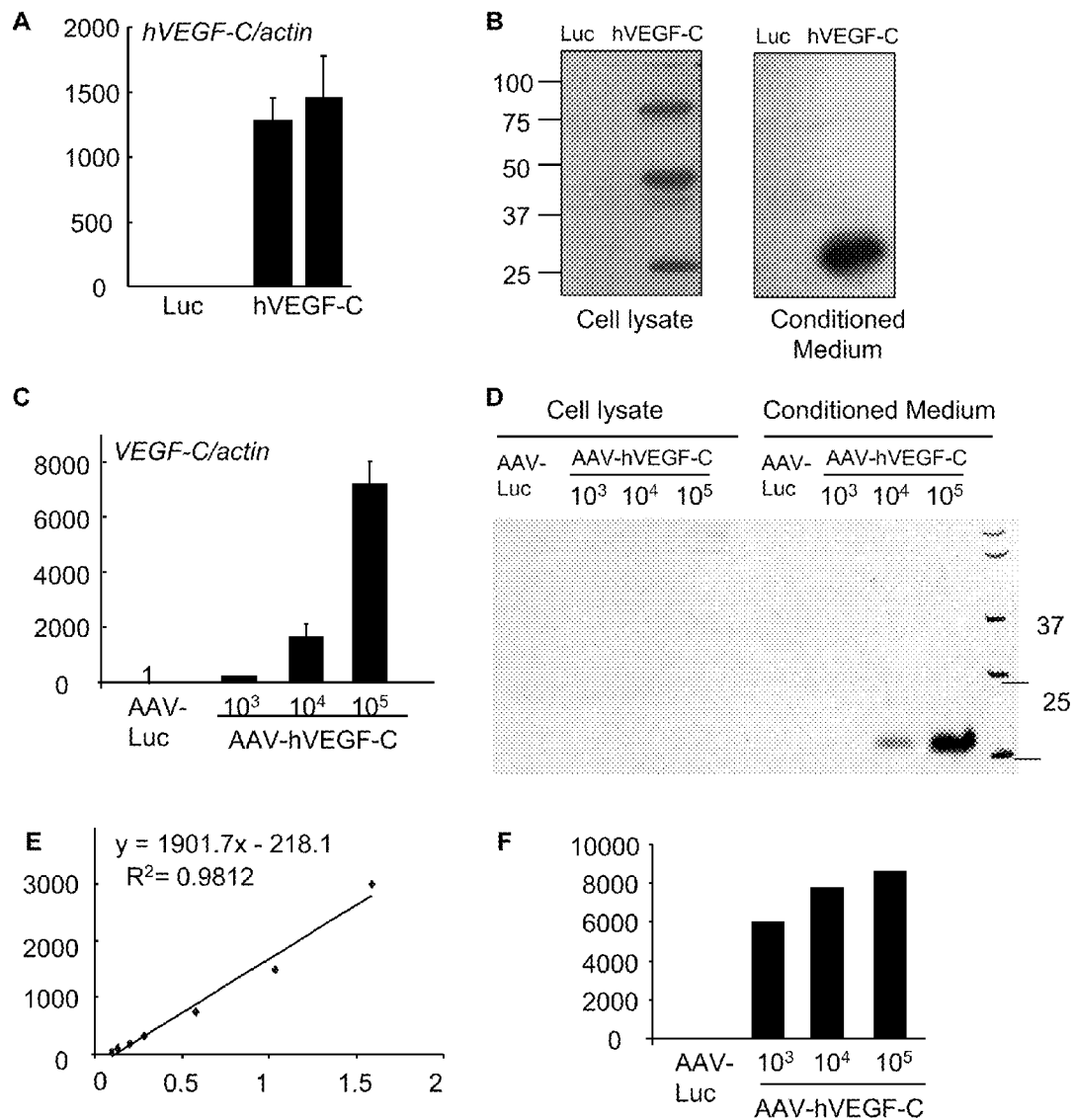
Figures 23A-F

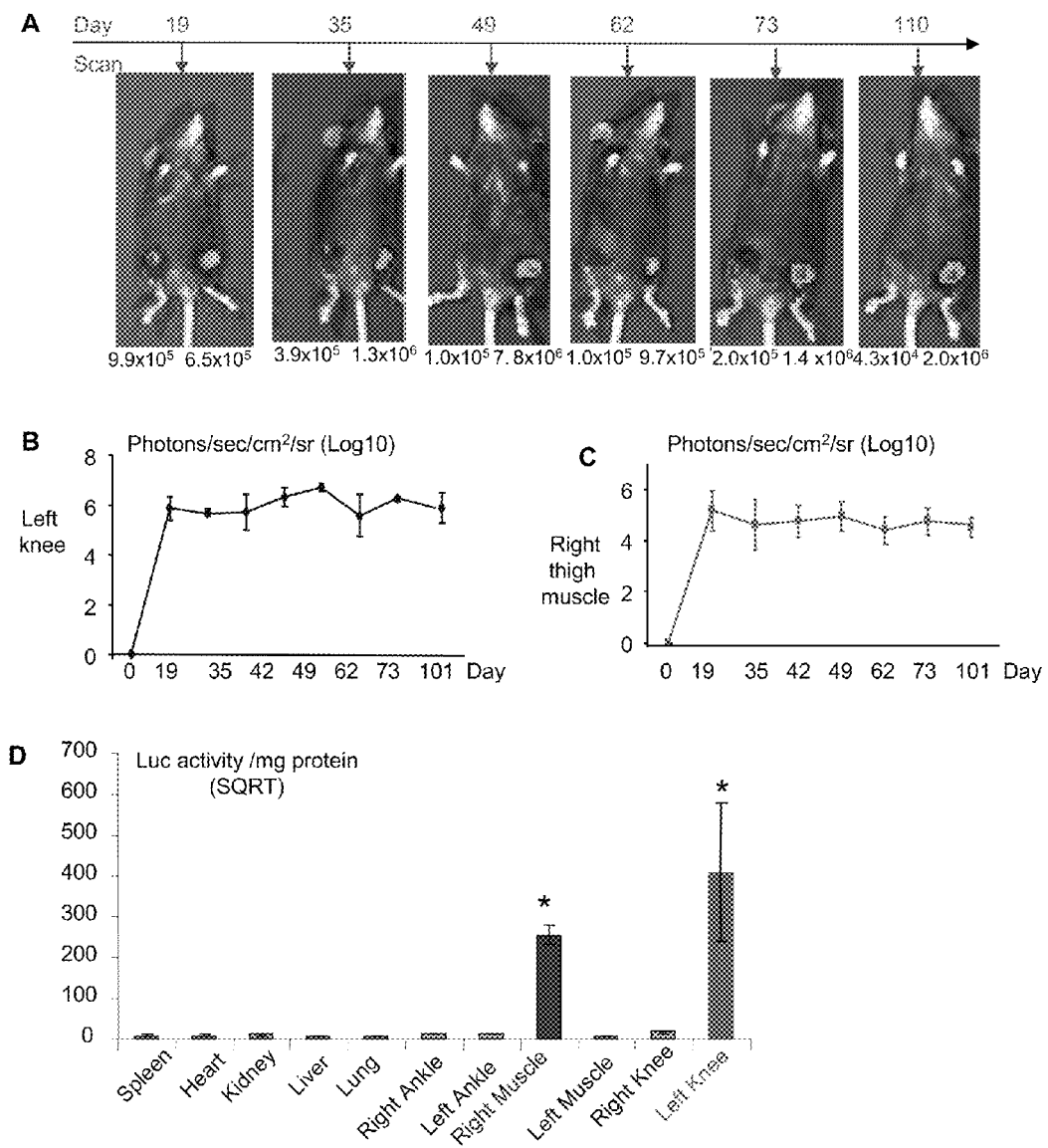
Figure 24A-D

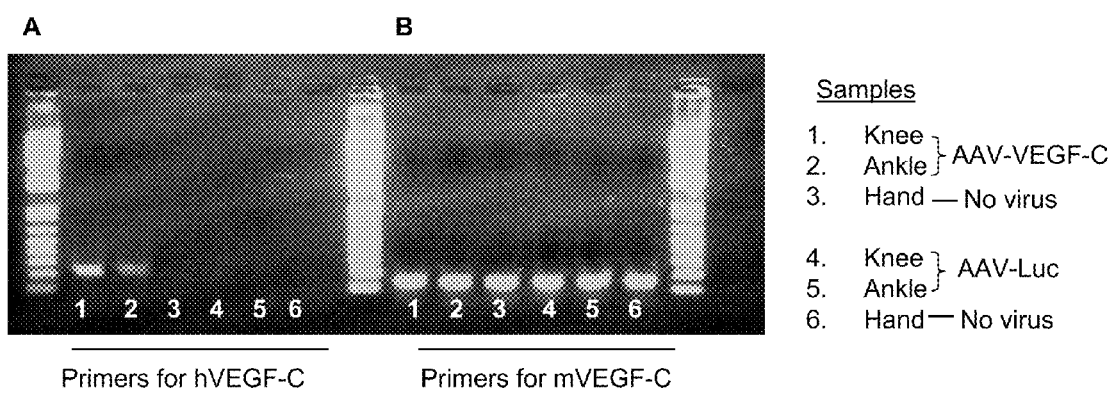
Figures 25A-B

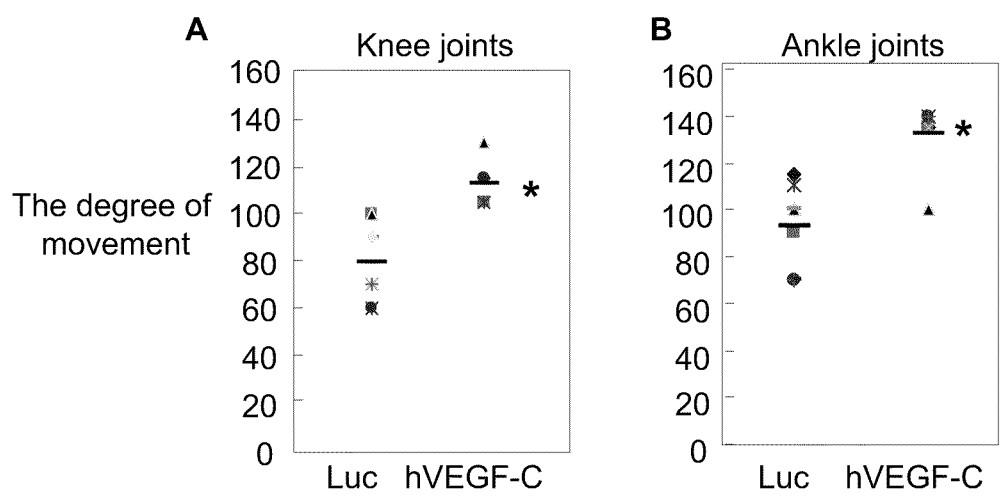
Figure 26A-B

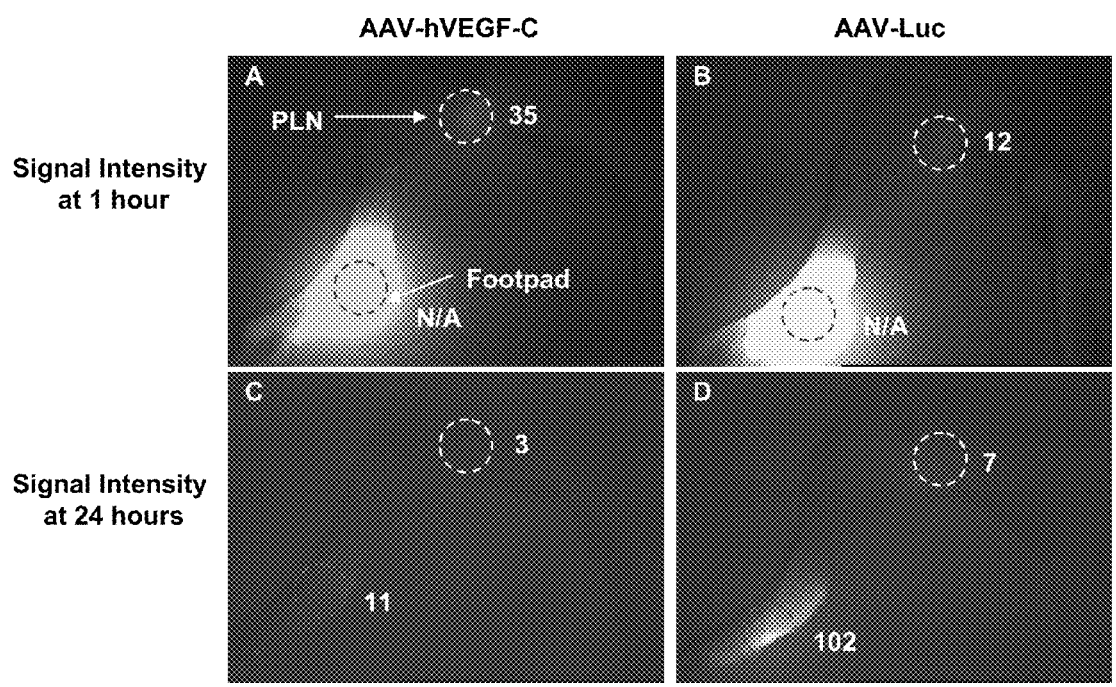
Figure 27A-D

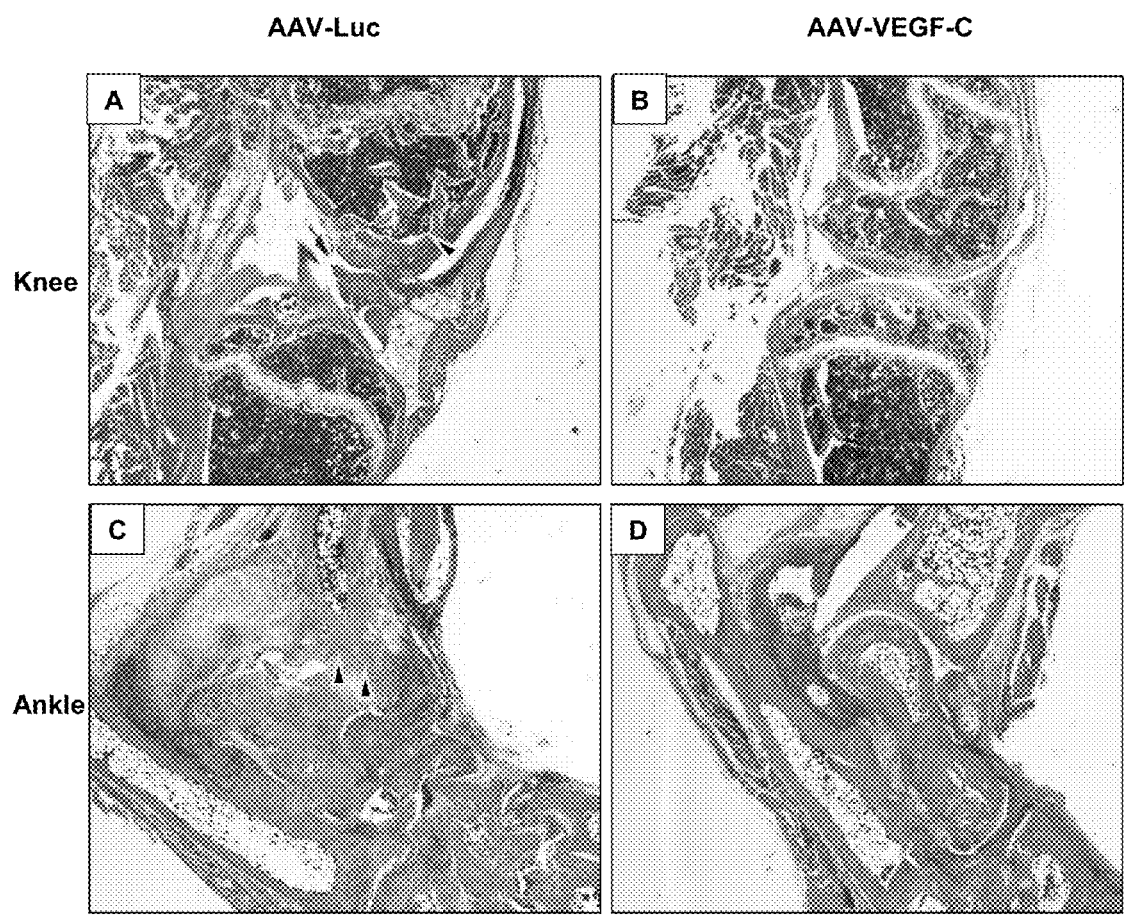
Figures 28A-D

SEQUENCE LISTING

<160> NUMBER OF SEQ ID NOS: 37

<210> SEQ ID NO 1
<211> LENGTH: 1260
<212> TYPE: DNA

<213> ORGANISM: Homo sapien

<400> SEQUENCE: 1

```
atgcacttgc tgggcttctt ctctgtggcg tgttctctgc tcgccgctgc gctgctcccg      60
ggtcctcgcg aggcgcccgc cgccgccgcc gccttcgagt ccggactcga cctctcggac     120
gcggagcccg acgcgggcga ggccacggct tatgcaagca agatctggag ggagcagtta     180
cggtctgtgt ccagtgtaga tgaactcatg actgtactct acccagaata ttggaaaatg     240
tacaagtgtc agctaaggaa aggaggctgg caacataaca gagaacaggc caacctcaac     300
tcaaggacag aagagactat aaaatttgct gcagcacatt ataatacaga gatcttgaaa     360
agtattgata atgagtggag aaagactcaa tgcatgccac gggaggtgtg tatagatgtg     420
gggaaggagt ttggagtcgc gacaaacacc ttctttaaac ctccatgtgt gtccgtctac     480
agatgtgggg gttgctgcaa tagtgagggg ctgcagtgca tgaacaccag cacgagctac     540
ctcagcaaga cgttatttga aattacagtg cctctctctc aaggccccaa accagtaaca     600
atcagttttg ccaatcacac ttcctgccga tgcatgtcta aactggatgt ttacagacaa     660
gttcattcca ttattagacg ttccctgcca gcaacactac cacagtgtca ggcagcgaac     720
aagacctgcc ccaccaatta catgtggaat aatcacatct gcagatgcct ggctcaggaa     780
gattttatgt tttcctcgga tgctggagat gactcaacag atggattcca tgacatctgt     840
ggaccaaaca aggagctgga tgaagagacc tgtcagtgtg tctgcagagc ggggcttcgg     900
cctgccagct gtggacccca caagaactga cagaaact catgccagtg tgtctgtaaa     960
aacaaactct tccccagcca atgtggggcc aaccgagaat tgatgaaaa cacatgccag    1020
tgtgtatgta aagaacctg ccccagaaat caaccccctaa atcctggaaa atgtgcctgt    1080
gaatgtacag aaagtccaca gaaatgcttg ttaaaaggaa agaagttcca ccaccaaaca    1140
tgcagctgtt acagacggcc atgtacgaac cgccagaagg cttgtgagcc aggattttca    1200
tatagtgaag aagtgtgtcg ttgtgtccct tcatattgga aaagaccaca aatgagctaa    1260
```

<210> SEQ ID NO 2
<211> LENGTH: 419
<212> TYPE: PRT
<213> ORGANISM: Homo sapien

<400> SEQUENCE: 2

```
Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140
```

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
            165                 170                 175

Ser Thr Ser Tyr Leu Ser Lys Thr Leu Phe Glu Ile Thr Val Pro Leu
        180                 185                 190

Ser Gln Gly Pro Lys Pro Val Thr Ile Ser Phe Ala Asn His Thr Ser
    195                 200                 205

Cys Arg Cys Met Ser Lys Leu Asp Val Tyr Arg Gln Val His Ser Ile
210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
            245                 250                 255

Leu Ala Gln Glu Asp Phe Met Phe Ser Ser Asp Ala Gly Asp Asp Ser
        260                 265                 270

Thr Asp Gly Phe His Asp Ile Cys Gly Pro Asn Lys Glu Leu Asp Glu
    275                 280                 285

Glu Thr Cys Gln Cys Val Cys Arg Ala Gly Leu Arg Pro Ala Ser Cys
290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
            325                 330                 335

Asn Thr Cys Gln Cys Val Cys Lys Arg Thr Cys Pro Arg Asn Gln Pro
        340                 345                 350

Leu Asn Pro Gly Lys Cys Ala Cys Glu Cys Thr Glu Ser Pro Gln Lys
    355                 360                 365

Cys Leu Leu Lys Gly Lys Lys Phe His His Gln Thr Cys Ser Cys Tyr
370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
            405                 410                 415

Gln Met Ser

<210> SEQ ID NO 3
<211> LENGTH: 1248
<212> TYPE: DNA
<213> ORGANISM: Mus musculus

<400> SEQUENCE: 3
atgcacttgc tgtgcttctt gtctctggcg tgttccctgc tcgccgctgc gctgatcccc     60
agtccgcgcg aggcgcccgc caccgtcgcc gccttcgagt cgggactggg cttctcggaa    120
gcggagcccg acgggggcga ggtcaaggct tttgaaggca agacctggag ggagcagttg    180
cggtctgtgt ccagcgtaga tgagctgatg tctgtcctgt acccagacta ctggaaaatg    240
tacaagtgcc agctgcggaa aggcggctgg cagcagccca ccctcaatac caggacaggg    300
gacagtgtaa atttgctgc tgcacattat aacacagaga tcctgaaaag tattgataat    360
gagtggagaa agactcaatg catgccacgt gaggtgtgta tagatgtggg gaaggagttt    420
ggagcagcca caaacacctt ctttaaacct ccatgtgtgt ccgtctacag atgtgggggt    480
tgctgcaaca gcgaggggct gcagtgcatg aacaccagca caggttaccc cagcaagacg    540

```
ttgtttgaaa ttacagtgcc tctctcacaa ggccccaaac cagtcacaat cagttttgcc    600
aatcacactt cctgccggtg catgtctaaa ctggatgttt acagacaagt tcattcaatt    660
attagacgtt ctctgccagc aacattacca cagtgtcagg cagctaacaa gacatgtcca    720
acaaactatg tgtggaataa ctacatgtgc cgatgcctgg ctcagcagga ttttatcttt    780
tattcaaatg ttgaagatga ctcaaccaat ggattccatg atgtctgtgg acccaacaag    840
gagctggatg aagacacctg tcagtgtgtc tgcaaggggg ggcttcggcc atctagttgt    900
ggaccccaca agaactaga tagagactca tgtcagtgtg tctgtaaaaa caaactttc     960 cctaattcat gtggagccaa cagggaattt gatgagaata catgtcagtg tgtatgtaaa    1020
agaacgtgtc caagaaatca gcccctgaat cctgggaaat gtgcctgtga atgtacagaa    1080
aacacacaga agtgcttcct taaagggaag aagttccacc atcaaacatg cagttgttac    1140
agaagaccgt gtgcgaatcg actgaagcat tgtgatccag gactgtcctt tagtgaagaa    1200
gtatgccgct gtgtcccatc gtattggaaa aggccacatc tgaactaa                 1248
```

<210> SEQ ID NO 4
<211> LENGTH: 415
<212> TYPE: PRT
<213> ORGANISM: Mus musculus

<400> SEQUENCE: 4

```
Met His Leu Leu Cys Phe Leu Ser Leu Ala Cys Ser Leu Leu Ala Ala
1               5                   10                  15

Ala Leu Ile Pro Ser Pro Arg Glu Ala Pro Ala Thr Val Ala Ala Phe
            20                  25                  30

Glu Ser Gly Leu Gly Phe Ser Glu Ala Glu Pro Asp Gly Gly Glu Val
        35                  40                  45

Lys Ala Phe Glu Gly Lys Asp Leu Glu Glu Gln Leu Arg Ser Val Ser
    50                  55                  60

Ser Val Asp Glu Leu Met Ser Val Leu Tyr Pro Asp Tyr Trp Lys Met
65                  70                  75                  80

Tyr Lys Cys Gln Leu Arg Lys Gly Gly Trp Gln Gln Pro Thr Leu Asn
                85                  90                  95

Thr Arg Thr Gly Asp Ser Val Lys Phe Ala Ala His Tyr Asn Thr
            100                 105                 110

Glu Ile Leu Lys Ser Ile Asp Asn Glu Trp Arg Lys Thr Gln Cys Met
        115                 120                 125

Pro Arg Glu Val Cys Ile Asp Val Gly Lys Glu Phe Gly Ala Ala Thr
    130                 135                 140

Asn Thr Phe Phe Lys Pro Pro Cys Val Ser Val Tyr Arg Cys Gly Gly
145                 150                 155                 160

Cys Cys Asn Ser Glu Gly Leu Gln Cys Met Asn Thr Ser Thr Gly Tyr
                165                 170                 175

Leu Ser Lys Thr Leu Phe Glu Ile Thr Val Pro Leu Ser Gln Gly Pro
            180                 185                 190

Lys Pro Val Thr Ile Ser Phe Ala Asn His Thr Ser Cys Arg Cys Met
        195                 200                 205

Ser Lys Leu Asp Val Tyr Arg Gln Val His Ser Ile Ile Arg Arg Ser
    210                 215                 220

Leu Pro Ala Thr Leu Pro Gln Cys Gln Ala Ala Asn Lys Thr Cys Pro
225                 230                 235                 240

Thr Asn Tyr Val Trp Asn Asn Tyr Met Cys Arg Cys Leu Ala Gln Gln
                245                 250                 255
```

```
Asp Phe Ile Phe Tyr Ser Asn Val Glu Asp Ser Thr Asn Gly Phe
                260                 265                 270

His Asp Val Cys Gly Pro Asn Lys Glu Leu Asp Glu Asp Thr Cys Gln
            275                 280                 285

Cys Val Cys Lys Gly Gly Leu Arg Pro Ser Ser Cys Gly Pro His Lys
290                 295                 300

Glu Leu Asp Arg Asp Ser Cys Gln Cys Val Cys Lys Asn Lys Leu Phe
305                 310                 315                 320

Pro Asn Ser Cys Gly Ala Asn Arg Glu Phe Asp Glu Asn Thr Cys Gln
                325                 330                 335

Cys Val Cys Lys Arg Thr Cys Pro Arg Asn Gln Pro Leu Asn Pro Gly
            340                 345                 350

Lys Cys Ala Cys Glu Cys Thr Glu Asn Thr Gln Lys Cys Phe Leu Lys
        355                 360                 365

Gly Lys Lys Phe His His Gln Thr Cys Ser Cys Tyr Arg Arg Pro Cys
    370                 375                 380

Ala Asn Arg Leu Lys His Cys Asp Pro Gly Leu Ser Phe Ser Glu Glu
385                 390                 395                 400

Val Cys Arg Cys Val Pro Ser Tyr Trp Lys Arg Pro His Leu Asn
                405                 410                 415

<210> SEQ ID NO 5
<211> LENGTH: 21
<212> TYPE: DNA
<213> ORGANISM: Artificial
<220> FEATURE:
<223> OTHER INFORMATION: primer for mouse VEGF-A

<400> SEQUENCE: 5
tttactgctg tacctccacc a                                                21

<210> SEQ ID NO 6
<211> LENGTH: 22
<212> TYPE: DNA
<213> ORGANISM: Artificial
<220> FEATURE:
<223> OTHER INFORMATION: primer for mouse VEGF-A

<400> SEQUENCE: 6
atctctccta tgtgctggct tt                                               22

<210> SEQ ID NO 7
<211> LENGTH: 20
<212> TYPE: DNA
<213> ORGANISM: Artificial
<220> FEATURE:
<223> OTHER INFORMATION: primer for mouse VEGF-B

<400> SEQUENCE: 7
cctggaagaa cacagccaat                                                  20

<210> SEQ ID NO 8
<211> LENGTH: 20
<212> TYPE: DNA
<213> ORGANISM: Artificial
<220> FEATURE:
<223> OTHER INFORMATION: primer for mouse VEGF-B

<400> SEQUENCE: 8
ggagtgggat ggatgatgtc                                                  20

<210> SEQ ID NO 9
```

```
<211> LENGTH: 20
<212> TYPE: DNA
<213> ORGANISM: Artificial
<220> FEATURE:
<223> OTHER INFORMATION: primer for mouse VEGF-C

<400> SEQUENCE: 9
gggaagaagt tccaccatca                                          20

<210> SEQ ID NO 10
<211> LENGTH: 20
<212> TYPE: DNA
<213> ORGANISM: Artificial
<220> FEATURE:
<223> OTHER INFORMATION: primer for mouse VEGF-C

<400> SEQUENCE: 10
atgtggcctt ttccaatacg                                          20

<210> SEQ ID NO 11
<211> LENGTH: 20
<212> TYPE: DNA
<213> ORGANISM: Artificial
<220> FEATURE:
<223> OTHER INFORMATION: primer for mouse VEGF-D

<400> SEQUENCE: 11
gctgtcactg ttgcccacta                                          20

<210> SEQ ID NO 12
<211> LENGTH: 20
<212> TYPE: DNA
<213> ORGANISM: Artificial
<220> FEATURE:
<223> OTHER INFORMATION: primer for mouse VEGF-D

<400> SEQUENCE: 12
cccttccttt ctgagtgctg                                          20

<210> SEQ ID NO 13
<211> LENGTH: 20
<212> TYPE: DNA
<213> ORGANISM: Artificial
<220> FEATURE:
<223> OTHER INFORMATION: primer for mouse PLGF

<400> SEQUENCE: 13
gggaagaagc aagacatgga                                          20

<210> SEQ ID NO 14
<211> LENGTH: 20
<212> TYPE: DNA
<213> ORGANISM: Artificial
<220> FEATURE:
<223> OTHER INFORMATION: primer for mouse PLGF

<400> SEQUENCE: 14
atgtcctgtc ccatctccag                                          20

<210> SEQ ID NO 15
<211> LENGTH: 20
<212> TYPE: DNA
<213> ORGANISM: Artificial
<220> FEATURE:
<223> OTHER INFORMATION: primer for mouse beta-actin

<400> SEQUENCE: 15
```

```
acccagatca tgtttgagac                                              20

<210> SEQ ID NO 16
<211> LENGTH: 22
<212> TYPE: DNA
<213> ORGANISM: Artificial
<220> FEATURE:
<223> OTHER INFORMATION: primer for mouse beta-actin

<400> SEQUENCE: 16
gtcaggatct tcatgaggta gt                                           22

<210> SEQ ID NO 17
<211> LENGTH: 22
<212> TYPE: DNA
<213> ORGANISM: Artificial
<220> FEATURE:
<223> OTHER INFORMATION: probe

<400> SEQUENCE: 17
gcccaggggg gtccccggga gg                                           22

<210> SEQ ID NO 18
<211> LENGTH: 22
<212> TYPE: DNA
<213> ORGANISM: Artificial
<220> FEATURE:
<223> OTHER INFORMATION: probe

<400> SEQUENCE: 18
gcccagggga ttctccggga gg                                           22

<210> SEQ ID NO 19
<211> LENGTH: 19
<212> TYPE: DNA
<213> ORGANISM: Artificial
<220> FEATURE:
<223> OTHER INFORMATION: probe

<400> SEQUENCE: 19
cgagccggcc ccgcccatc                                               19

<210> SEQ ID NO 20
<211> LENGTH: 20
<212> TYPE: DNA
<213> ORGANISM: Artificial
<220> FEATURE:
<223> OTHER INFORMATION: primer for mouse RANKL

<400> SEQUENCE: 20
ccaagatctc taacatgacg                                              20

<210> SEQ ID NO 21
<211> LENGTH: 20
<212> TYPE: DNA
<213> ORGANISM: Artificial
<220> FEATURE:
<223> OTHER INFORMATION: primer for mouse RANKL

<400> SEQUENCE: 21
caccatcagc tgaagatagt                                              20

<210> SEQ ID NO 22
<211> LENGTH: 24
<212> TYPE: DNA
<213> ORGANISM: Artificial
<220> FEATURE:
```

<223> OTHER INFORMATION: primer for mouse VEGF-A

<400> SEQUENCE: 22
attgagaccc tggtggacat cttc                                              24

<210> SEQ ID NO 23
<211> LENGTH: 24
<212> TYPE: DNA
<213> ORGANISM: Artificial
<220> FEATURE:
<223> OTHER INFORMATION: primer for mouse VEGF-A

<400> SEQUENCE: 23
ctcatctctc ctatgtgctg gctt                                              24

<210> SEQ ID NO 24
<211> LENGTH: 20
<212> TYPE: DNA
<213> ORGANISM: Artificial
<220> FEATURE:
<223> OTHER INFORMATION: primer for mouse VEGF-B

<400> SEQUENCE: 24
cctggaagaa cacagccaat                                                   20

<210> SEQ ID NO 25
<211> LENGTH: 20
<212> TYPE: DNA
<213> ORGANISM: Artificial
<220> FEATURE:
<223> OTHER INFORMATION: primer for mouse VEGF-B

<400> SEQUENCE: 25
ggagtgggat ggatgatgtc                                                   20

<210> SEQ ID NO 26
<211> LENGTH: 20
<212> TYPE: DNA
<213> ORGANISM: Artificial
<220> FEATURE:
<223> OTHER INFORMATION: primer for mouse VEGF-C

<400> SEQUENCE: 26
gggaagaagt tccaccatca                                                   20

<210> SEQ ID NO 27
<211> LENGTH: 20
<212> TYPE: DNA
<213> ORGANISM: Artificial
<220> FEATURE:
<223> OTHER INFORMATION: primer for mouse VEGF-C

<400> SEQUENCE: 27
atgtggcctt ttccaatacg                                                   20

<210> SEQ ID NO 28
<211> LENGTH: 20
<212> TYPE: DNA
<213> ORGANISM: Artificial
<220> FEATURE:
<223> OTHER INFORMATION: primer for mouse VEGF-D

<400> SEQUENCE: 28
gctgtcactg ttgcccacta                                                   20

<210> SEQ ID NO 29

```
<211> LENGTH: 20
<212> TYPE: DNA
<213> ORGANISM: Artificial
<220> FEATURE:
<223> OTHER INFORMATION: primer for mouse VEGF-D

<400> SEQUENCE: 29
cccttccttt ctgagtgctg                                          20

<210> SEQ ID NO 30
<211> LENGTH: 22
<212> TYPE: DNA
<213> ORGANISM: Artificial
<220> FEATURE:
<223> OTHER INFORMATION: primer for mouse TNF

<400> SEQUENCE: 30
cacactcaga tcatcttctc aa                                       22

<210> SEQ ID NO 31
<211> LENGTH: 22
<212> TYPE: DNA
<213> ORGANISM: Artificial
<220> FEATURE:
<223> OTHER INFORMATION: primer for mouse TNF

<400> SEQUENCE: 31
agtagacaag gtacaaccca tc                                       22

<210> SEQ ID NO 32
<211> LENGTH: 20
<212> TYPE: DNA
<213> ORGANISM: Artificial
<220> FEATURE:
<223> OTHER INFORMATION: primer for mouse CD11b

<400> SEQUENCE: 32
gactcagtga gccccatcat                                          20

<210> SEQ ID NO 33
<211> LENGTH: 20
<212> TYPE: DNA
<213> ORGANISM: Artificial
<220> FEATURE:
<223> OTHER INFORMATION: primer for mouse CD11b

<400> SEQUENCE: 33
agatcgtctt ggcagatgct                                          20

<210> SEQ ID NO 34
<211> LENGTH: 21
<212> TYPE: DNA
<213> ORGANISM: Artificial
<220> FEATURE:
<223> OTHER INFORMATION: primer for mouse IL-1

<400> SEQUENCE: 34
attagacaac tgcactacag g                                        21

<210> SEQ ID NO 35
<211> LENGTH: 22
<212> TYPE: DNA
<213> ORGANISM: Artificial
<220> FEATURE:
<223> OTHER INFORMATION: primer for mouse IL-1

<400> SEQUENCE: 35
```

-continued

```
ggagaatatc acttgttggt tg                                             22

<210> SEQ ID NO 36
<211> LENGTH: 20
<212> TYPE: DNA
<213> ORGANISM: Artificial
<220> FEATURE:
<223> OTHER INFORMATION: primer for mouse beta-actin

<400> SEQUENCE: 36
acccagatca tgtttgagac                                                20

<210> SEQ ID NO 37
<211> LENGTH: 22
<212> TYPE: DNA
<213> ORGANISM: Artificial
<220> FEATURE:
<223> OTHER INFORMATION: primer for mouse beta-actin

<400> SEQUENCE: 37
gtcaggatct tcatgaggta gt                                             22
```

METHODS AND COMPOSITIONS FOR TREATING INFLAMMATORY CONDITIONS

This application claims the benefit of U.S. Provisional Patent Application Ser. No. 61/029,799, filed Feb. 19, 2008, which is hereby incorporated by reference in its entirety.

This invention was made with government support under grant number R01 AR48697 awarded by the National Institutes of Health. The U.S. government has certain rights in this invention.

FIELD OF THE INVENTION

The present invention is directed to methods and compositions effective for the treatment of inflammatory conditions.

BACKGROUND OF THE INVENTION

Joint disease in rheumatoid arthritis (RA) is characterized by inflamed hyperplastic synovial tissue or 'pannus' formation (Firestein G. S., "Evolving Concepts of Rheumatoid Arthritis," *Nature* 423:356-361 (2003)). Pannus is composed of various cell types that produce a vast array of inflammatory mediators, including cytokines and chemokines that destroy the extracellular matrix in the joint by direct and indirect mechanisms. Pannus is extremely vascular, providing portals of entry for effector cells to enter the joint from the circulation and mediate joint destruction via autocrine and paracrine mechanisms. As a result of neovascularization, inflammatory cell infiltration, and concomitant synovial cell hyperplasia, the volumes of the synovium and synovial fluid increase, resulting in joint swelling and pain (Maruotti et al., "Angiogenesis in Rheumatoid Arthritis," *Histol Histopathol* 21:557-566 (2006)). Thus, inhibition of new blood vessel formation has been proposed as an important therapeutic approach for patients with inflammatory-erosive arthritis (De Bandt et al., "Blockade of Vascular Endothelial Growth Factor Receptor I (VEGF-RI), but not VEGF-RII, Suppresses Joint Destruction in the K/BxN Model of Rheumatoid Arthritis," *J Immunol* 171:4853-4859 (2003)).

The lymphatic circulation has been known for many years to be an important secondary vascular system to remove fluid, macromolecules, and cells from the interstitial spaces, and it functions as a 'compensatory' system for blood circulation. However, studies of the lymphatic system have been hampered until recently by the lack of markers that definitively distinguish blood from lymphatic vessels and a paucity of knowledge about growth factors specific to lymphatic endothelial cells. Gene array analysis comparing lymphatic endothelial cells and blood vascular endothelial cells has recently identified numerous previously unknown lineage-specific markers for blood and lymphatic vascular endothelium. Newly identified lymphatic endothelium-specific markers include lymphatic endothelial hyaluronan receptor 1 (LYVE-1), prospero-related homeobox 1, vascular endothelial growth factor receptor 3 (VEGFR-3), and the mucin-type transmembrane glycoprotein podoplanin (Podgrabinska et al., "Molecular Characterization of Lymphatic Endothelial Cells," *Proc Natl Acad Sci USA* 99:16069-16074 (2002); Kriehuber et al., "Isolation and Characterization of Dermal Lymphatic and Blood Endothelial Cells Reveal Stable and Functionally Specialized Cell Lineages," *J Exp Med* 194:797-808 (2001); Mäkinen et al., "Isolated Lymphatic Endothelial Cells Transduce Growth, Survival and Migratory Signals via the VEGF-C/D Receptor VEGFR-3," *EMBO J* 20:4762-4773 (2001); Hirakawa et al., "Identification of Vascular Lineage-Specific Genes by Transcriptional Profiling of Isolated Blood Vascular and Lymphatic Endothelial Cells," *Am J Pathol* 162:575-586 (2003)).

The role of inflammation-induced lymphangiogenesis in the pathogenesis of joint disease and arthritis is unknown. Early clinical studies proposed that inflammation-driven lymphangiogenesis induces the expansion of the lymphatic network in an exacerbated manner such that the lymphatic vessels may be dysfunctional, as reported in psoriasis and Crohn disease (Braverman et al., "Microcirculation in Psoriatic Skin," *J Invest Dermatol* 62:493-502 (1974); Ryan T J., "Microcirculation in Psoriasis: Blood Vessels, Lymphatics and Tissue Fluid," *Pharmacol Ther* 10:27-64 (1980); Kovi et al., "Ultrastructure of Intestinal Lymphatics in Crohn's Disease," *Am J Clin Pathol* 76:385-394 (1981), which are hereby incorporated by reference in their entirety). Recent studies have continued to focus on identifying and inhibiting signaling pathways that mediate lymphangiogenesis in several models of inflammation, including rheumatoid arthritis (see e.g. U.S. Patent Publication No. 20040120950 to Alitalo et al.). In general, however, the effects of manipulating lymphangiogenesis in these inflammatory conditions remain unclear. Therefore, a strategy for modulating the lymphatic system as a therapeutic approach for alleviating inflammation, particularly joint inflammation, is lacking.

The present invention is directed to overcoming this and other deficiencies in the art.

SUMMARY OF THE INVENTION

A first aspect of the present invention relates to a method of treating an inflammatory condition in a patient. This method includes providing a therapeutic agent that is a vascular endothelial growth factor receptor-3 (VEGFR-3) agonist or a nucleic acid molecule encoding a VEGFR-3 agonist and administering the therapeutic agent to the patient having the inflammatory condition. Administration of the therapeutic agent is effective to treat the inflammatory condition.

A second aspect of the present invention is directed to a pharmaceutical composition. The pharmaceutical composition contains a pharmaceutically acceptable carrier, a therapeutic agent that is a VEGFR-3 agonist or a nucleic molecule encoding a VEGFR-3 agonist, and one or more additional therapeutic agents.

A third aspect of the present invention relates to a therapeutic system for treating an anti-inflammatory condition. This therapeutic system includes a first pharmaceutical composition comprising a pharmaceutically acceptable carrier and a therapeutic agent that is a VEGFR-3 agonist or a nucleic molecule encoding a VEGFR-3 agonist. The therapeutic system also includes a second pharmaceutical composition comprising a pharmaceutically acceptable carrier and one or more additional therapeutic agents.

The additional therapeutic agent(s) for use in any aspect of the present invention includes, without limitation, a VEGFR-1 or 2 antagonist, an agent that interferes with VEGF/VEGFR-1 or -2 interaction, a Non-Steroidal Anti-Inflammatory drug ("NSAID"), an analgesic, a glucocorticoid, a disease-modifying anti-rheumatic drug, a dihydrofolate reductase inhibitor, a Tumor Necrosis Factor-α inhibitor, a biological response modifier, or any combination thereof.

Two major functions of the lymphatic system are removal of excess tissue fluid and transfer of cells to local lymph nodes ("LN"). Accumulation of interstitial fluid and cells are major features of synovitis in inflammatory-erosive arthritis. In the early phase of inflammatory arthritis, lymphangiogenesis is not coupled with vascular neoangiogenesis and results in edema. Therefore, stimulation of lymphangiogenesis alone or in combination with the inhibition of angiogenesis will reduce the severity of synovitis, bone destruction, and draining lymph node hyperplasia. The present invention is directed to methods and compositions for stimulating lymphangiogenesis while inhibiting angiogenesis in the early phase of rheumatoid arthritis ("RA") and other inflammatory diseases, particularly inflammatory joint diseases, to improve treatment and disease outcome.

BRIEF DESCRIPTION OF THE DRAWINGS

FIGS. 1A-B illustrate the differential expression of genes within the vascular endothelial growth factor (VEGF) and platelet-derived growth factor (PDGF) families in $CD11b^+$/$Gr-1^{-/lo}$ osteoclast precursors (OCPs) from tumor necrosis factor-transgenic (TNF-Tg) and wild-type (WT) mice. $CD11b^-$/$Gr-1^{-/lo}$ cells from peripheral blood (FIG. 1A) and bone marrow (FIG. 1B) from TNF-Tg (n=7) and WT (n=23) mice were pooled and purified by flow sorting. The RNA samples were subjected to microarray analysis using the GeneChip Mouse Genome 430A 2.0 array from Affymetrix. The array data on angiogenic gene expression was analyzed using GeneTraffic software. The expression ratio was calculated by dividing the mean value of the intensity of RNA signals from two separate arrays of TNF-Tg OCPs by that from WT cells.

FIGS. 2A-E show tumor necrosis factor (TNF) mediated increase in vascular endothelial growth factor-C (VEGF-C) expression in OCPs. Wild-type spleen cells were cultured with macrophage colony-stimulating factor (M-CSF) for 3 days to enrich for OCPs. OCPs were cultured in 10% serum with M-CSF and treated with phosphate-buffered saline (PBS) or TNF (10 ng/mL). FIG. 2A shows VEGF-C mRNA expression levels at various time points following TNF treatment as measured by real-time reverse transcription-polymerase chain reaction (RT-PCR). FIG. 2B is an immunoblot of VEGF-C and β-actin protein levels in control and TNF treated OCPs. FIG. 2C shows expression of VEGF-A, -B, -C, -D, and placental growth factor (PLGF) mRNA in OCPs treated with TNF or PBS for 24 hours. Values represent the mean of triplicate loadings plus standard deviation. FIG. 2D shows a dose-dependent effect of TNF treatment on VEGF-C mRNA expression after 24-hours of exposure. FIG. 2E shows the fold-induction of VEGF-C expression following 24-hour treatment with TNF (10 ng) alone or in combination with interleukin 1 (IL-1) (TNF and IL-1 10 ng/mL). Experiments were repeated twice with similar results.

FIGS. 3A-C demonstrate TNF mediated binding of nuclear proteins to the nuclear factor-kappa B (NF-κB) binding sequence of the VEGF-C promoter. Raw264.7 osteoclast/macrophage precursors were cultured in 0.5% bovine serum albumin overnight. Cells were treated with TNF for 30 to 60 minutes and nuclear extracts were isolated. FIG. 3A is an immunoblot of nuclear extracts probed with anti-NF-κB p65 and p50 antibodies. The nuclear extracts were also subjected to an electrophoretic mobility shift assay using a $^{32}P$-labeled probe consisting of the putative NF-κB binding sequence of the mouse VEGF-C promoter (FIG. 3B, SEQ ID NO: 17). The specificity of binding was confirmed by using 50-fold more unlabeled wild-type (WT) or mutated probe (SEQ ID NO: 18), in which the putative NF-κB binding sequence was mutated and did not bind NF-κB in a competition reaction. An SP-1 probe was used as a loading control. FIG. 3C shows a decrease in VEGF-C expression in WT osteoclast precursors that were treated with TNF± an NF-κB inhibitor for 24 hours.

Expression of VEGF-C mRNA was determined by real-time RT-PCR. Values represent the mean value of three experiments plus standard deviation. Experiments were repeated two times with similar results.

FIGS. 4A-K depict the high level of VEGF-C expression in cells derived from the joints of tumor necrosis factor-transgenic (TNF-Tg) mice. Ankle and wrist joints of TNF-Tg mice and WT littermates were subjected to collagenase digestion to isolate cells, which were stained with fluorescein isothiocyanate (FITC)-anti-CD11b and phycoerythrin-anti-Gr-1, and subjected to fluorescence-activated cell sorting analysis. FIG. 4A is a representative histogram of labeled cells from one pair of TNF-Tg and WT mice showing the percentage of $CD11b^+$/$Gr-1^{-/lo}$ cells in each. FIGS. 4B-I are immunofluorescent images of TNF-Tg (FIGS. 4B-E) and WT (FIGS. 4F-I) cells ($3\times10^5$) double-stained with FITC-anti-CD11b (FIGS. 4C, G) and rabbit anti-VEGF-C (FIGS. 4B, F) followed by anti-rabbit Alexa 546. TO-PRO-3 iodide was used as a DNA dye for nuclear staining (FIGS. 4D, H). Colocalization of VEGF-C, CD11b, and DNA staining is shown in FIGS. 4E and I. Pictures were taken under a confocal microscope at a power of ×20. The expression of VEGF-A, -C, and -D mRNA was measured by RT-PCR in WT and Tg-TNF cells that were cultured with M-CSF for 3 days. The fold increase in VEGF-A, -C, and -D expression in TNF-Tg over WT cells is shown in FIG. 4J. Values represent the mean of triplicate loadings plus standard deviation (SD). The expression levels of TNF and IL-1 mRNA in joint extracts from TNF-Tg mice and WT littermates were also determined by real-time RT-PCR and are shown in FIG. 4K. Experiments were repeated using four additional pairs of TNF-Tg and WT mice with similar results.

FIGS. 5A-F illustrate the observed enlargement of lymphatic vessels in the joints of TNF-Tg mice. Joint sections from TNF-Tg mice (FIGS. 5A-B) or WT littermates (FIGS. 5C-D) were immunostained with anti-LYVE-1 (FIG. 5A, C) or CD31 (FIGS. 5B, D) antibodies. Micrographs (×20) show increased numbers and diameters of $LYVE-1^+$ lymphatic vessels in the synovium of TNF-Tg mice (compare FIGS. 5A and C). The area (FIG. 5E) and number (FIG. 5F) of lymphatic vessels within the synovium were counted. Values are the means plus standard deviation of five TNF-Tg mice and six WT mice. *$p<0.05$ versus WT samples. LYVE-1, lymphatic endothelial hyaluronan receptor 1.

Figure 6G:
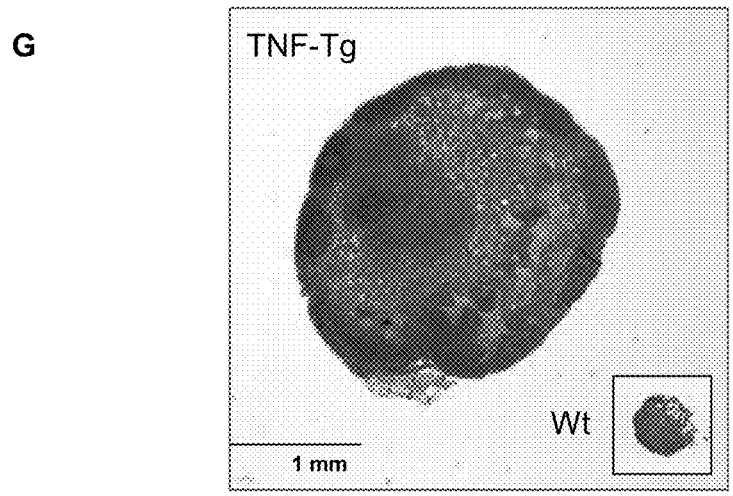

FIGS. 6A-G show the increased volume of popliteal lymph nodes (PLN) in TNF-Tg. Representative post-contrast magnetic resonance imaging sections from a TNF-Tg (FIG. 6A) and WT (FIG. 6C) mouse (5 months old) are shown. Using a semi-automated segmentation procedure in Amira software, the synovial and lymph node ("LN") volumes were quantified (FIGS. 6E-F) and visualized in TNF-Tg (FIG. 6B) and WT (FIG. 6D) mice. *$p<0.05$ versus WT samples (n=5). FIG. 6G are representative hematoxylin-and-eosin (H&E) stained sections (×4) from TNF-Tg and WT animals demonstrating the difference in LN size.

FIGS. 7A-E show increased lymphangiogenesis in joints of mice with serum-induced arthritis. Wild-type mice, receiving serum from K/BxN mice to induce arthritis, were sacrificed at 0, 14, and 35 days after serum injection (n=3 or 4 mice at each time point). Ankle joint sections were immunostained with anti-LYVE-1 antibody. FIGS. 7A-B are representative images showing inflamed pannus and large numbers of $LYVE-1^+$ lymphatic vessels (FIG. 7B, arrows) at day 35. FIG. 7A shows H&E staining. The area and number of lymphatic vessels within the pannus were determined by histomorphometric analysis (FIGS. 7C-D). The area of inflammation is shown in FIG. 7E. Data values represent the means plus standard deviation of 3 or 4 mice at each time point.

FIGS. 8A-C illustrate the effect of anti-TNF therapy on the lymphatic vasculature in joints of TNF-Tg mice. TNF-Tg mice (2.5 months old) received placebo or anti-TNF antibody (10 mg/kg per week×8 weeks). Ankle sections were immunostained with anti-LYVE-1 antibody. The area (FIG. 8A) and number (FIG. 8B) of LYVE-1$^+$ lymphatic vessels within the pannus and the area of inflammation (FIG. 8C) per ankle were assessed. Values are the means plus standard deviation of three placebo- or anti-TNF-treated mice. *p<0.05 anti-TNF-treated group compared with placebo group.

FIGS. 9A-G illustrate the differences in enhancement pattern in LNs between WT and TNF-Tg mice and the correlation with expanded LYVE-1 positive sinuses. CE-MRI image of a popliteal LN from a representative WT mouse (FIG. 9A) and corresponding microphotographs of LYVE-1 immuno-histochemistry at 4× (FIG. 9B) and 20× (FIG. 9C). CE-MRI (FIG. 9D) and histology (FIGS. 9E and F) of a representative TNF-Tg LN, with markedly increased size and CE compared to WT. Note that the CE is localized to the portion of the LN that corresponds to the LYVE-1$^+$ sinuses in both WT and TNF-Tg mice, opposed to the highly cellular regions that show a lower degree of enhancement. The area covered by LYVE-1$^+$ vessels/mm$^2$ was determined by point counting (FIG. 9G). Data are mean values from two TNF-Tg mice and two WT littermate controls and confirms a 3-fold increase in lymphatic vessel area in TNF-Tg vs. WT LNs.

FIGS. 10A-B are graphs displaying contrast enhancement versus time after intravenous injection in a WT mouse (FIG. 10A) and a TNF-Tg mouse (FIG. 10B) for muscle (diamonds), synovium (triangles), and LN (squares). Measurements were made every 12 seconds for the first ten minutes after injection and every minute from 10 to 20 minutes after injection. The WT mouse shows a modest increase in LN enhancement followed by a gradual decline of signal intensity with no concurrent decrease in synovium or muscle. The TNF-Tg mouse shows a much larger increase in Contrast Enhancement ("CE") in the LN and this high level of enhancement persists throughout the 20 minute study. The boxed regions highlight the time period for the high resolution post-contrast MRI scans. Note that there are no changes in muscle CE during this time period in both WT and TNF-Tg mice, indicating that this tissue may be used as a normalization tissue for quantifications of CE in the LN.

FIGS. 11A-D show quantitative measurements of LNs in WT and TNF-Tg mice. WT (n=6) and TNF-Tg (n=10) received CE-MRI at 5 months of age and 3D-MRI quantification revealed highly significant differences (*; p<0.01) in LN volume (FIG. 11A) and Normalized LN Contrast Enhancement ("NLCE") (FIG. 11B). A regression analysis (FIG. 11C) revealed a highly significant correlation between LN volume and CE ($R_2$=0.73, p<0.0001). A significant difference (*; p<0.01) in LNcap (LN volume×NLCE) was seen between WT and TNF-Tg animals, with a wide range of values in the transgenic animals (FIG. 11D).

FIGS. 12A-G depict the decrease in LN quantitative biomarkers after anti-TNF therapy and the persistence of LYVE-1 positive lymphatic vessels after therapy in LN and synovium. Eight TNF-Tg mice received CE-MRI and were entered into the study when a synovial threshold of 3 mm$^3$ was first measured. Four TNF-Tg mice received anti-TNF therapy and four received placebo, and each were followed with CE-MRI every two weeks for eight weeks. In addition, aged-matched WT mice (n=4) were scanned at baseline and 8 weeks. NLCE levels (FIG. 12A) showed a significant decrease with therapy (slope=−0.16, p=0.001), reaching WT levels after 4 weeks of treatment. Placebo mice demonstrated a significant increase in this value from baseline to 8 weeks (slope=0.12, p<0.01). Similar results were found with LN capacity measurements (FIG. 12B). Anti-TNF mice showed a significant decrease in LNcap (slope=−3.58, p<0.0001) approaching WT levels at 8 weeks. A significant increase in LNcap was found in placebo mice (slope=2.85, p=0.001). Representative CE-MRI images from an anti-TNF treated TNF-Tg mouse at baseline (FIG. 12C) and 8 weeks (FIG. 12D) visualize the decrease in both volume and contrast enhancement that occurs in response to therapy. Immunohistochemistry of LYVE-1$^+$ vessels in TNF-Tg LN 8-weeks after anti-TNF therapy (FIGS. 12E and G), and in placebo (FIG. 12F) treated synovium is shown at 20× (FIG. 12E) and 40× (FIGS. 12F-G) magnification. Note that while the number of LYVE-1$^+$ vessels are similar, the luminal area (arrows) of these vessels in the placebo treated animals is markedly larger than that of the anti-TNF treated group.

FIGS. 13A-G illustrate the relationship between LNcap and severity of joint swelling. The synovial volumes of the TNF-Tg mice shown in FIG. 10 were analyzed with a regression analysis vs. LNcap (FIG. 13A). One mouse was excluded from the analysis due to excessive pannus necrosis. There was a significant negative correlation found between synovial volume and LNcap. CE-MR images and 3D reconstruction from a representative TNF-Tg mouse with high LNcap (FIGS. 13B-D) display a corresponding low synovial volume, while a TNF-Tg mouse with low LNcap (FIG. 13E-G) is associated with greater synovial volume.

FIGS. 14A-G show the accelerated progression of knee arthritis in mice with low LNcap. Two mice with low LNcap (<35) and two mice with high LNcap (>50) received follow-up CE-MRI at 2 weeks and 4 weeks. Measurements of average knee synovial volumes (KSV) show a dramatic increase in low LNcap animals at 4 weeks (FIG. 14A). By contrast, mice with high LNcap demonstrated no increase in synovial volume at 2 or 4 weeks. Representative CE-MR images of the knee from a TNF-Tg mouse with low LNcap from the placebo group in FIG. 12 at 2.5 months (FIG. 14B), 3 months (FIG. 14C), 3.5 months (FIG. 14D), 4 months (FIG. 14E), 4.5 months (FIG. 14F), and 5 months (FIG. 14G) show a rapid progression of arthritis. Mild inflammation at 2.5 months progressed to severe edema at 3.5 to 4 months. Necrosis of pannus tissue resulting in a loss of vascularity (dark regions indicated by arrows) and concomitant decrease in synovial volume measurements was evident at 4.5 to 5 months.

Figure 15:
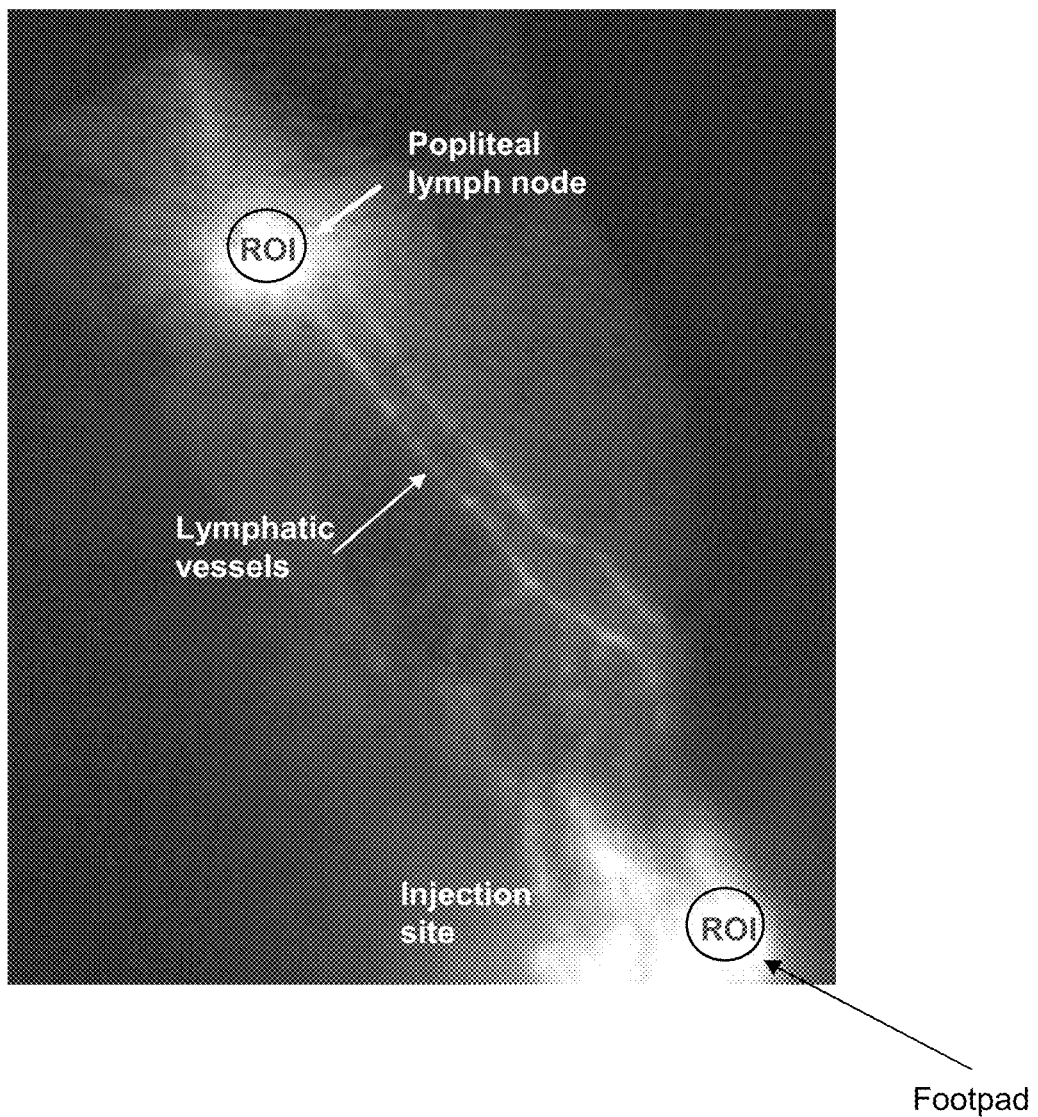

FIG. 15 is a composite near infrared ("NIR") image of the leg region in a WT mouse that received intra-dermal injection of indocyanine green (ICG) (1 µg in 10 µl) into the footpad. The migration of ICG to the PLN was imaged using a NIR camera in real time. The picture shows the path of ICG from the injection site to the PLN through draining lymphatic vessels. Quantification was performed from the video images by establishing regions of interest at the injection site and PLN from a NIR image frame.

FIGS. 16A-H depict the increase in lymphangiogenesis and lymphatic flow in draining PLNs of TNF-Tg mice and wildtype littermates (n=4; 4-6 mo. old). FITC-Dextran (10 µl) was injected intra-dermally into the hind footpads of mice, and PLNs were removed 1 hour later for confocal microscopy. Sixty to eighty sections (600-800 µm deep) were scanned from the surface of the nodes, and images 500 µm deep from representative WT (FIG. 16A) and TNF-Tg (FIG. 16B) mice are shown at 4× magnification. Representative H&E sections (4×) show extensive enlargement of TNF-Tg PLN vs. WT PLN (FIGS. 16C and D, respectively). ICG (10 µl) was injected intradermally into the hind footpads of WT and TNF-Tg mice, and PLNs were harvested 1 hour later. Parallel sections were observed with an infrared filter, and representative images (4×) show the distribution of ICG fluorescence in WT (FIG. 16E) and TNF-Tg (FIG. 16F). Afterwards, immunohistochemistry with anti-LYVE-1 antibodies was performed on the same sections, and fluorescent images of the positive LYVE-1 staining in WT and Tg-TNF are shown at 4× (FIGS. 16G-H, respectively). Co-localization of ICG and LYVE-1 signals are indicated by arrows.

Figure 17:
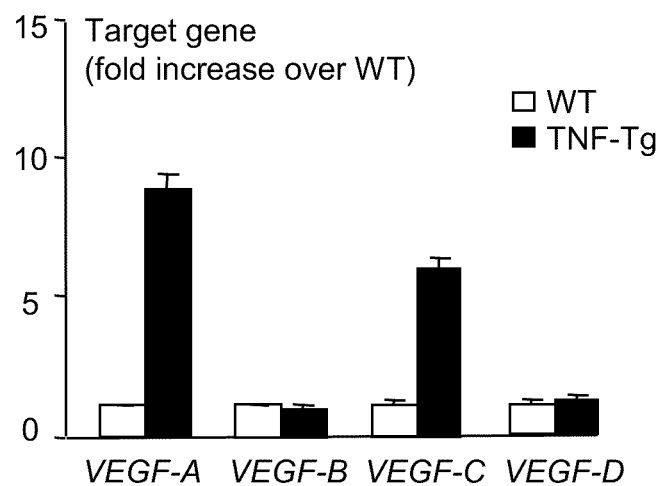

FIG. 17 is a graph showing the fold-increase in VEGF-A and VEGFC RNA expression in LNs of TNF-Tg mice compared to WT mice. Total RNA was extracted from pooled PLNs (n=3-4) obtained from 4-6-month-old TNF-Tg mice or WT littermates, and the mRNA expression levels were determined by real time RT-PCR standardized to a β-actin control. The data are presented as the mean fold-increase±SD vs. the mean WT expression levels (*$p<0.05$ vs. WT).

FIGS. 18A-P show inhibition of TNF-induced PLN enlargement and lymphatic vessel formation using VEGFR-2 and VEGFR-3 neutralizing antibodies. TNF-Tg mice (2.5-month-old, n=5 per treatment) received CE-MRI scans of PLNs, ankle, and knee joints to obtain baseline value of synovial and PLN volume, as described previously (Proulx et al., "MRI and Quantification of Draining Lymph Node Function in Inflammatory Arthritis," *Ann N Y Acad Sci* 1117:106-23 (2007); Proulx et al., "Longitudinal Assessment of Synovial, Lymph Node, and Bone Volumes in Inflammatory Arthritis in Mice by In Vivo Magnetic Resonance Imaging and Microfocal Computed Tomography," *Arthritis Rheum* 56(12):4024-37 (2007), which are hereby incorporated by reference in their entirety). Animals were then treated with VEGFR-2 or VEGFR-3 neutralizing antibodies (from Imclone Systems), or IgG placebo control (0.8 mg/mouse, i.p. twice a week) for 8 weeks. The post-treatment CE-MRI scans were performed one day before sacrifice. FIGS. 18A-F are representative 2D CE-MRI images showing a marked increase in IgG treated PLN volume over 8 weeks (FIGS. 18A-B), compared to the lack of changes observed in PLN from animals treated with anti-VEGFR-2 (FIGS. 18E-F) and anti-VEGFR-3 antibodies (FIGS. 18C-D). The percent change in PLN volume from baseline is shown in FIG. 18G. The data are presented as mean±SD for each treatment group (*$p<0.05$ vs. IgG). The PLN weights (FIG. 18H) after 8-weeks are presented as mean±SD for each treatment group (*$p<0.05$ vs. IgG). The treatment effects of IgG (FIGS. 18I-J), anti-VEGFR3 (FIGS. 18K-L), and anti-VEGFR2 (FIGS. 18M-N) on LN structure and lymphangiogenesis were examined by H&E staining (FIGS. 18I, K, M) or by immunostaining with anti-LYVE-1 antibody (FIG. 18J, L, N). Lymphatic vessel number (FIG. 18O) and lymphatic vessel area (FIG. 18P) were determined by histomorphometry of anti-LYVE-1 antibody-stained sections. The data are presented as mean±SD for each treatment group (*$p<0.05$ vs. IgG).

FIGS. 19A-F show the differential effects of VEGFR-2 and VEGFR-3 blockade on ankle synovial volume in TNF-Tg mice. The ankle synovial volumes of the mice were measured before and after treatment with IgG, anti-VEGFR3 antibody, or anti-VEGR2 antibody as described supra (FIG. 18) and are shown individually in FIG. 19A. FIG. 19B shows the mean±SD percentage change in synovial volume from baseline (*$p<0.05$ vs. IgG) in each treatment group. Representative H&E stained sections of ankle tissue from each treatment group are shown at 4× magnification in FIG. 18C. Note that the anti-VEGFR-3 treatment increases joint inflammation, while anti-VEGFR-2 treatment decreases synovitis, compared to IgG placebo control (see arrows in FIG. 19C). Histomorphometry of H&E stained ankle sections was performed to quantify the inflammation area (FIG. 19D). Values represent the mean±SD percentage of synovial area over the total tissue area (*$p<0.05$ vs. IgG placebo). Immunostaining on parallel tissue sections for LYVE-1$^+$ lymphatic vessels and CD31$^+$ blood vessels was performed as described in the accompanying Examples. The number of LYVE-1$^+$ vessels (FIG. 19E) and CD31$^+$ blood vessels (FIG. 19F) is presented as mean±SD for each treatment group (*$p<0.05$ vs. IgG).

FIGS. 20A-H show inhibition of lymph flow from the foot to draining PLN with VEGFR-3 blockade. TNF-Tg mice (2.5-month-old, n=4) were treated with VEGFR-3 neutralizing antibody or IgG placebo control as described supra in FIG. 18, and received an ICG intra-dermal injection in their hind footpads after 8 weeks of treatment. Five minutes after the ICG administration the injected hind legs were imaged for 1-2 hours until reaching the S-Max using a NIR camera, and this NIR imaging was repeated for 10 minutes 24 hours later. FIGS. 20A-D are representative ICG-NIR images obtained at S-max (FIG. 20A,C) and 24 hour after injection (FIGS. 20B, D) showing the gross difference in lymph drainage from the injection site in the footpad (ROI-Foot) to the PLN (ROI-PLN), in placebo (FIGS. 20A-B) and anti-VEGFR-3 (FIGS. 20C-D) treated mice. T-initial (FIG. 20E), T-max (FIG. 20F), S-max (FIG. 20G), and % Clearance (FIG. 20H) in the region of interest (indicated by arrows in 20A) were analyzed as described in the accompanying Examples, and are presented as the mean±SD (*$p<0.05$ vs. IgG placebo).

FIGS. 21A-J show a decreases in VEGF-C expressing CD11b$^+$ cells in LNs of TNF-Tg mice with VEGFR-3 blockade. PLNs from TNF-Tg mice (4-6-month-old; FIGS. 21A-C) and WT littermates (FIG. 21D-F) were double immunostained with PE-anti-CD11b (FIGS. 21B, E) and FITC-anti-VEGF-C (FIGS. 21A, D) antibodies. Representative pictures taken at 40× indicate the co-localization of CD11b and VEGF-C proteins (FIGS. 21C, F; TO-PRO-3-iodide DNA staining shown). Histomorphometry was performed to determine the percentage of CD11b$^+$ or VEGF-C$^+$ cells in the PLNs (FIG. 21G). The values are the mean±SD of 4 fields from 4 individual mice per genotype (*$p<0.05$ vs. WT). Total RNA was extracted from pooled (n=3-4) PLNs and the expression levels of TNF and IL-1 were determined by real-time RT-PCR standardized to a β-actin control (FIG. 21H). The data are presented as the mean fold-increase±SD vs. the mean WT expression (*$p<0.05$ vs. WT). PLNs from IgG- and VEGFR-3 neutralizing antibody-treated TNF-Tg mice were stained with anti-CD11b antibody, and the percentage of CD11b$^+$ cells was calculated by dividing the number of CD11b$^+$ cells by the total number of cells (FIG. 21I). The expression levels of CD11b mRNA in WT and IgG or VEGFR-3 antibody treated TNF-Tg were determined by real time RT-PCR (FIG. 21J). The data are presented as the mean fold-increase±SD vs. the mean IgG expression. *$p<0.05$ vs. IgG treated mice.

Figure 22:
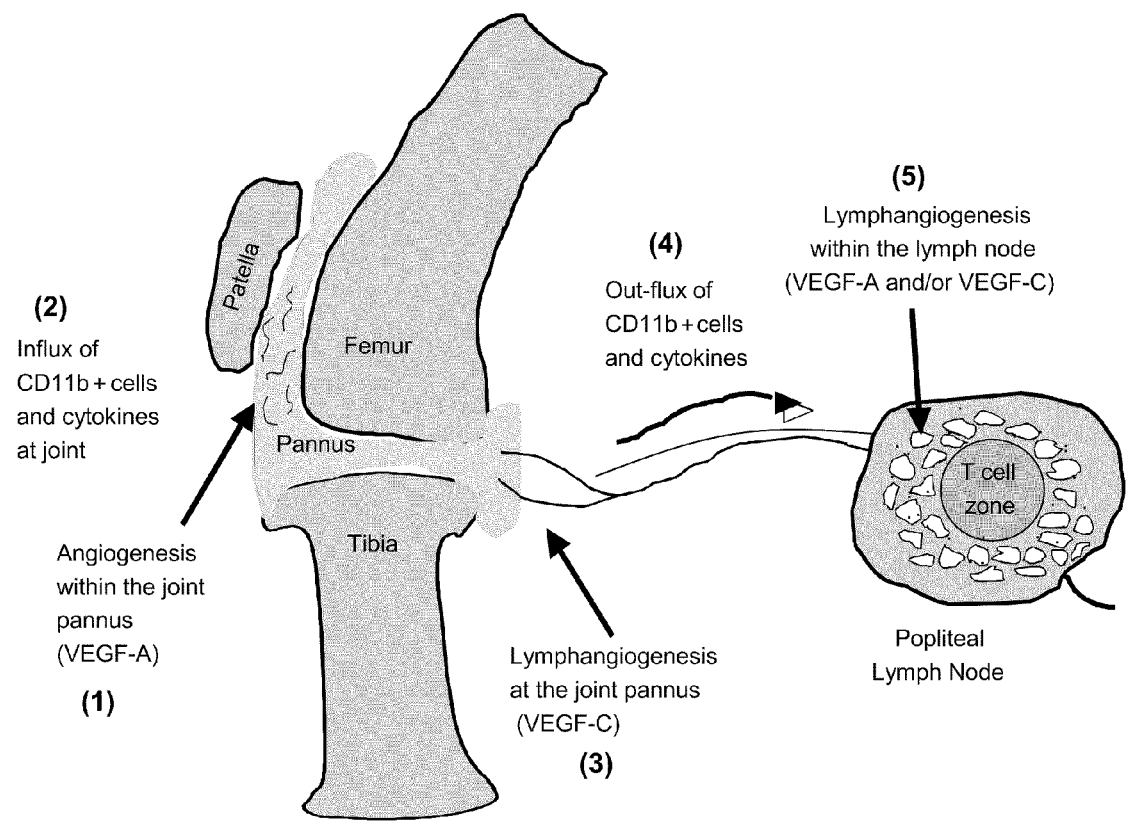

FIG. 22 represents a model for the role of lymphatic vasculature and drainage in the pathogenesis process of inflammatory arthritis. (1) TNF-induced angiogenesis through VEGFR-2 occurs at a very early stage and provides support for an expansion of the inflammatory pannus. (2) Increased inflammatory cytokines and chemokines recruit circulating CD11b$^+$ myeloid cells to joints. (3) CD11b$^+$ cells produce VEGF-C in response to inflammatory signals and stimulate the formation of lymphatic vessels through VEGFR-3 signaling. (4) These functional vessels transport inflammatory lymph carrying inflammatory cells, catabolic factors and cytokines to the draining popliteal LNs. (5) Within the LNs, cytokines stimulate CD11b$^+$ cells to produce VEGF-C and promote lymphangiogenesis, leading to an expansion of the LNs and dilation of lymphatic sinuses containing inflammatory cells.

FIGS. 23A-F depict the generation of recombinant adeno-associated virus (rAAV)-hVEGF-C. cDNA encoding human VEGF-C was cloned into a AAV expression vector to generate pAAV-hVEGF-C. The pAAV-hVEGF-C or a pAAV-Luc expression vector (control) were transiently transfected into PlatE cells (FIGS. 23A, B) or PlatE cells were infected with various amount of rAAV-hVEGF-C or rAAV-Luc virus (FIGS. 23C-F) for 48 hours. The expression of hVEGF-C mRNA in transiently transfected PlatE cells (FIG. 23A) or infected PlatE cells (FIG. 23C) was assessed by real time RT-PCR. hVEGF-C protein levels in whole cell lysate or conditioned medium from transiently transfected PlatE cells (FIG. 23B) or infected PlatE cells (FIG. 23D) was assessed by Western blot analysis. The expression of hVEGF-C protein in the conditioned medium of rAAV-VEGF-C infected PlatE cells was assessed by a ELISA kit (FIG. 23E shows the standard curve and FIG. 23F shows expression data).

FIGS. 24A-D show the long term expression of rAAV-luciferase after a single injection. TNF-Tg mice (2.5-month-old; n=3) received an intra-articular injection of $2 \times 10^{10}$ units of rAAV-Luc in the left knee and an intramuscular injection of $5 \times 10^9$ units of the same virus in the quadricep muscle of the right leg on day 0. Bioluminescent (BL) images were taken at different days thereafter. FIG. 24A is a series of BL images of a representative mouse at days 19, 35, 49, 62, 73 and 110 after injection. The numbers of light units in the left knee joint and right quadriceps muscle are listed underneath each image. FIGS. 24B and C are graphs showing the mean number of light units in the left knee (FIG. 24B) and right thigh muscle (FIG. 24C) plus standard error of mean (SEM) of 3 mice on the respective days after injection. FIG. 24D shows the levels of luciferase activity in various tissues harvested at day 110 after injection. Values represent the means plus SEM of 3 mice. $*p<0.05$ vs specimen from the contralateral limb.

FIGS. 25A-B show the detection of human VEGF-C mRNA expression in tissues 3-months post-AAV-hVEGF-C virus injection. Total RNA was extracted from soft tissues around the knee, ankle, and hand. Tissue RNA was subjected to RT-PCR using primers specific for human (FIG. 25A) and mouse (FIG. 25B) VEGF-C. hVEGF-C RNA expression was detected in knee and ankle tissue injected with AAV-VEGF-C, but not hand tissue or tissues injected with AAV-Luc.

FIGS. 26A-B show the improvement in joint flexibility in TNF-Tg mice following intra-articular injection of AAV-VEGF-C. TNF-Tg mice (1.5-month-old) received intra-articular injection of AAV-VEGF-C or AAV-Luc in the knee and ankle joints. Three months after virus injection, animals were anesthetized and the degree of movement of knee (FIG. 26A) and ankle (FIG. 26B) joints was measured using a double-armed goniometer. The degree of movement for each individual joint is plotted and the horizontal bars represent the mean of nine AAV-Luc-injected joints and seven AAV-VEGF-C-injected joints. $*p<0.05$ vs Luc-injected joints.

FIGS. 27A-D show the increase in lymphatic drainage from foot to local draining LNs after intra-articular injection of AAV-VEGF-C virus. Three months after AAV joint injection, TNF-Tg mice received ICG-NIR lymphatic imaging on legs. The intensity of ICG signal at 1 hour (FIGS. 27A-B) and 24 hours (FIGS. 27C-D) after ICG footpad injection in AAV-hVEGF-C (FIGS. 27A, C) and AAV-Luc (FIGS. 27B, D) treated animals are shown. VEGF-C treatment increases the amount of ICG draining from foot to the PLN (FIG. 27A) as well as draining away from the PLNs (FIG. 27C). N/A=the ICG signal reaches the saturation point.

FIGS. 28A-D show the reduction in inflammation and bone erosion observed following intra-articular injection of AAV-VEGF-C. TNF-Tg mice were sacrificed 3 months after AAV joint injection. H&E stained knee (FIGS. 28A-B) and ankle (FIGS. 28C-D) sections from AAV-hVEGF-C (FIGS. 28B, D) and AAV-Luc (FIGS. 28A, C) injected joints show serious inflammation (arrows) and bone destruction (arrow heads) in AAV-Luc control injected joints compared to AAV-hVEGF-C treated animals.

DETAILED DESCRIPTION OF THE INVENTION

A first aspect of the present invention relates to a method of treating an inflammatory condition in a patient. This method involves providing a therapeutic agent that is a vascular endothelial growth factor receptor-3 (VEGFR-3) agonist or a nucleic acid molecule encoding a VEGFR-3 agonist and administering the therapeutic agent to the patient having the inflammatory condition. Administration of the therapeutic agent is effective to treat the inflammatory condition.

As used herein, "patient" refers to any animal that exhibits an inflammatory condition, such as rheumatoid arthritis or any other condition described infra, which is amenable to treatment in accordance with the methods of the present invention. Preferably, the patient is a mammal. Exemplary mammalian patients include, without limitation, humans, non-human primates, dogs, cats, rodents (e.g., mouse, rat, guinea pig), horses, cattle and cows, sheep, and pigs.

The inflammatory condition to be treated using the methods of the present invention can be any inflammatory condition readily known in the art and diagnosable by a clinician. Examples of inflammatory conditions suitable for treatment using the methods of the present invention include, but are in no way limited to, rheumatoid arthritis (RA), insulin-dependent diabetes mellitus, multiple sclerosis, myasthenia gravis, Crohn's disease, autoimmune nephritis, primary biliary cirrhosis, psoriasis, acute pancreatitis, allograph rejection, allergic inflammation, inflammatory bowel disease, septic shock, osteoporosis, osteoarthritis, and cognitive deficits induced by neuronal inflammation. In a preferred embodiment of the present invention, the inflammatory condition is one that affects the joint, i.e., involves inflammation in or around the joint. Inflammatory conditions of the joint include rheumatoid arthritis, juvenile rheumatoid arthritis, systemic lupus erythematosus, gout, psoriatic arthritis, ankylosing spondylitis, Reiter's syndrome, adult Still's disease, viral arthritis, bacterial arthritis, and tuberculous arthritis. According to one embodiment, the inflammatory condition is not an inflammatory condition of the skin.

The therapeutic agent of the present invention is VEGFR-3 agonist. As described herein, a VEGFR-3 agonist is any compound that stimulates or activates the VEGFR-3 signaling pathway. In one embodiment of the present invention the VEGFR-3 agonist is a recombinant Vascular Endothelial Growth Factor C (VEGF-C) protein or an active peptide fragment or derivative thereof that binds to and activates the VEGFR-3. The VEGF-C protein or active peptide fragment corresponds to a naturally occurring protein (prepro-protein, partially-processed protein, or fully-processed mature protein) encoded by any allele of the human VEGF-C gene, or a polypeptide comprising a biologically active fragment of a naturally-occurring mature protein. The nucleotide sequences of VEGF-C, including the native human, non-human mammalian, and avian nucleotide sequences, as well as, nucleotide sequences of VEGF-C variants and analogs, are known in the art and have been described in detail in International Patent Publication No. WO 98/33917 to Alitalo et al.; Joukov et al., "A Recombinant Mutant Vascular Endothelial Growth Factor-C that Has Lost Vascular Endothelial Growth Factor Receptor-2 Binding, Activation, and Vascular Permeability Activities," *J. Biol. Chem.*, 273(12): 6599-6602 (1998); and in Joukov et al., "Proteolytic Processing Regulates Receptor Specificity and Activity of VEGF-C," *EMBO J.* 16(13): 3898-3911 (1997), all of which are incorporated herein by reference in their entirety.

Human VEGF-C is initially produced in human cells as a prepro-VEGF-C polypeptide of 419 amino acids. A cDNA and deduced amino acid sequence for human prepro-VEGF-C are set forth below in SEQ ID NOs: 1 and 2, respectively.

```
SEQ ID NO: 1 (Human VEGF-C cDNA)
atgcacttgc tgggcttctt ctctgtggcg tgttctctgc tcgccgctgc gctgctccg    60 ggtcctcgcg aggcgcccgc cgccgccgcc gccttcgagt ccggactcga cctctcggac   120
gcggagcccg acgcgggcga ggccacggct tatgcaagca agatctgga ggagcagtta    180 cggtctgtgt ccagtgtaga tgaactcatg actgtactct acccagaata ttggaaaatg   240
tacaagtgtc agctaaggaa aggaggctgg caacataaca gagaacaggc caacctcaac   300
tcaaggacag aagagactat aaaatttgct gcagcacatt ataatacaga gatcttgaaa   360
agtattgata atgagtggag aaagactcaa tgcatgccac gggaggtgtg tatagatgtg   420
gggaaggagt ttggagtcgc gacaaacacc ttctttaaac ctccatgtgt gtccgtctac   480
agatgtgggg gttgctgcaa tagtgagggg ctgcagtgca tgaacaccag cacgagctac   540
ctcagcaaga cgttatttga aattacagtg cctctctctc aaggcccaa accagtaaca    600 atcagttttg ccaatcacac ttcctgccga tgcatgtcta aactggatgt ttacagacaa   660
gttcattcca ttattagacg ttccctgcca gcaacactac cacagtgtca ggcagcgaac   720
aagacctgcc ccaccaatta catgtggaat aatcacatct gcagatgcct ggctcaggaa   780
gattttatgt tttcctcgga tgctggagat gactcaacag atggattcca tgacatctgt   840
ggaccaaaca aggagctgga tgaagagacc tgtcagtgtg tctgcagagc ggggcttcgg   900
cctgccagct gtggacccca caagaacta gacagaaact catgccagtg tgtctgtaaa    960
aacaaactct cccccagcca atgtggggcc aaccgagaat tgatgaaaa cacatgccag   1020 tgtgtatgta aagaacctg ccccagaaat caaccctaa atcctggaaa atgtgcctgt    1080
gaatgtacag aaagtccaca gaatgcttg ttaaaggaa agaagttcca ccaccaaaca     1140
tgcagctgtt acagacggcc atgtacgaac cgccagaagg cttgtgagcc aggattttca   1200
tatagtgaag aagtgtgtcg ttgtgtccct tcatattgga aaagaccaca atgagctaa   1260

SEQ ID NO: 2 (Human VEGF-C)
Met His Leu Leu Gly Phe Phe Ser Val Ala Cys Ser Leu Leu Ala Ala
1               5                  10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
        50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160
```

```
-continued
Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser
```

VEGF-C sequences from other species also have been reported. See, for example, Genbank Accession Nos. MMU73620 (*Mus musculus*) and CCY15837 (*Coturnix coturnix*), which are hereby incorporated by reference in their entirety. The cDNA and deduced amino acid sequence for mouse prepro-VEGF-C are set forth below in SEQ ID NOs: 3 and 4, respectively.

```
SEQ ID NO: 3 (Mouse VEGF-C)
atgcacttgc tgtgcttctt gtctctggcg tgttccctgc tcgccgctgc gctgatcccc      60
agtccgcgcg aggcgcccgc caccgtcgcc gccttcgagt cgggactggg cttctcggaa     120
gcggagcccg acggggggcga ggtcaaggct tttgaaggca aagacctgga ggagcagttg     180
cggtctgtgt ccagcgtaga tgagctgatg tctgtcctgt acccagacta ctggaaaatg     240
tacaagtgcc agctgcggaa aggcggctgg cagcagccca ccctcaatac caggacaggg     300
gacagtgtaa aatttgctgc tgcacattat aacacagaga tcctgaaaag tattgataat     360
gagtggagaa agactcaatg catgccacgt gaggtgtgta tagatgtggg aaggagttt      420 ggagcagcca caaacacctt ctttaaacct ccatgtgtgt ccgtctacag atgtgggggt     480
tgctgcaaca gcgaggggct gcagtgcatg aacaccagca caggttacct cagcaagacg     540
ttgtttgaaa ttacagtgcc tctctcacaa ggccccaaac cagtcacaat cagttttgcc     600
aatcacactt cctgccggtg catgtctaaa ctggatgttt acagacaagt tcattcaatt     660
```

-continued

```
attagacgtt ctctgccagc aacattacca cagtgtcagg cagctaacaa gacatgtcca    720
acaaactatg tgtggaataa ctacatgtgc cgatgcctgg ctcagcagga ttttatcttt    780
tattcaaatg ttgaagatga ctcaaccaat ggattccatg atgtctgtgg acccaacaag    840
gagctggatg aagacacctg tcagtgtgtc tgcaaggggg ggcttcggcc atctagttgt    900
ggaccccaca agaactaga tagagactca tgtcagtgtg tctgtaaaaa caaactttc    960 cctaattcat gtggagccaa cagggaattt gatgagaata catgtcagtg tgtatgtaaa    1020
agaacgtgtc aagaaatca gcccctgaat cctgggaaat gtgcctgtga atgtacagaa    1080
aacacacaga agtgcttcct taaagggaag aagttccacc atcaaacatg atgtacagaa    1140
agaagaccgt gtgcgaatcg actgaagcat tgtgatccag gactgtcctt tagtgaagaa    1200
gtatgccgct gtgtcccatc gtattggaaa aggccacatc tgaactaa    1248
```

SEQ ID NO: 4 (Mouse VEGF-C)

```
Met His Leu Leu Cys Phe Leu Ser Leu Ala Cys Ser Leu Leu Ala
1               5                   10                  15

Ala Leu Ile Pro Ser Pro Arg Glu Ala Pro Ala Thr Val Ala Ala Phe
                20                  25                  30

Glu Ser Gly Leu Gly Phe Ser Glu Ala Glu Pro Asp Gly Gly Glu Val
            35                  40                  45

Lys Ala Phe Glu Gly Lys Asp Leu Glu Glu Gln Leu Arg Ser Val Ser
        50                  55                  60

Ser Val Asp Glu Leu Met Ser Val Leu Tyr Pro Asp Tyr Trp Lys Met
65                  70                  75                  80

Tyr Lys Cys Gln Leu Arg Lys Gly Gly Trp Gln Gln Pro Thr Leu Asn
                85                  90                  95

Thr Arg Thr Gly Asp Ser Val Lys Phe Ala Ala Ala His Tyr Asn Thr
            100                 105                 110

Glu Ile Leu Lys Ser Ile Asp Asn Glu Trp Arg Lys Thr Gln Cys Met
        115                 120                 125

Pro Arg Glu Val Cys Ile Asp Val Gly Lys Glu Phe Gly Ala Ala Thr
    130                 135                 140

Asn Thr Phe Phe Lys Pro Pro Cys Val Ser Val Tyr Arg Cys Gly Gly
145                 150                 155                 160

Cys Cys Asn Ser Glu Gly Leu Gln Cys Met Asn Thr Ser Thr Gly Tyr
                165                 170                 175

Ley Ser Lys Thr Leu Phe Glu Ile Thr Val Pro Leu Ser Gln Gly Pro
            180                 185                 190

Lys Pro Val Thr Ile Ser Phe Ala Asn His Thr Ser Cys Arg Cys Met
        195                 200                 205

Ser Lys Leu Asp Val Tyr Arg Gln Val His Ser Ile Ile Arg Arg Ser
    210                 215                 220

Leu Pro Ala Thr Leu Pro Gln Cys Gln Ala Ala Asn Lys Thr Cys Pro
225                 230                 235                 240

Thr Asn Tyr Val Trp Asn Asn Tyr Met Cys Arg Cys Leu Ala Gln Gln
                245                 250                 255

Asp Phe Ile Phe Tyr Ser Asn Val Glu Asp Asp Ser Thr Asn Gly Phe
            260                 265                 270

His Asp Val Cys Gly Pro Asn Lys Glu Leu Asp Glu Asp Thr Cys Gln
        275                 280                 285

Cys Val Cys Lys Gly Gly Leu Arg Pro Ser Ser Cys Gly Pro His Lys
    290                 295                 300

Glu Leu Asp Arg Asp Ser Cys Gln Cys Val Cys Lys Asn Lys Leu Phe
305                 310                 315                 320
```

```
                                     -continued
Pro Asn Ser Cys Gly Ala Asn Arg Glu Phe Asp Glu Asn Thr Cys Gln
                325                 330                 335

Cys Val Cys Lys Arg Thr Cys Pro Arg Asn Gln Pro Leu Asn Pro Gly
            340             345                 350

Lys Cys Ala Cys Glu Cys Thr Glu Asn Thr Gln Lys Cys Phe Leu Lys
        355             360                 365

Gly Lys Lys Phe His His Gln Thr Cys Ser Cys Tyr Arg Arg Pro Cys
    370             375             380

Ala Asn Arg Leu Lys His Cys Asp Pro Gly Leu Ser Phe Ser Glu Glu
385             390             395                 400

Val Cys Arg Cys Val Pro Ser Tyr Trp Lys Arg Pro His Leu Asn
                405             410             415
```

The prepro-VEGF-C polypeptide is processed in multiple stages to produce a mature and most active VEGF-C polypeptide of about 21-23 kD (as assessed by SDS-PAGE under reducing conditions). Such processing includes cleavage of a signal peptide (residues 1-31 of SEQ ID NOS: 2 and 4); cleavage of a carboxyl-terminal peptide (corresponding approximately to amino acids 228-419 of SEQ ID NO: 2, amino acids 228-415 of SEQ ID NO: 4) to produce a partially-processed form of about 29 kD; and cleavage (apparently extracellularly) of an amino-terminal peptide (corresponding approximately to amino acids 32-103 of SEQ ID NO: 2) to produced a fully-processed mature form of about 21-23 kD. Experimental evidence demonstrates that partially-processed forms of VEGF-C (e.g., the 29 kD form) are able to bind VEGFR-3 (also referred to as Flt4 receptor), whereas high affinity binding to VEGFR-2 occurs only with the fully processed forms of VEGF-C. Thus, the 29 kD form is a selective VEGFR-3 agonist. It appears that VEGF-C polypeptides naturally associate as non-disulfide linked dimers.

In a preferred embodiment of the present invention, the recombinant VEGF-C protein or active peptide fragment or derivative thereof is an agonist to VEGFR-3 but not an agonist to VEGFR-2. For example, as set forth above, a recombinant VEGF-C protein or peptide comprising the partially processed form (e.g., the 29 kD form) will preferentially bind the VEGF3R, but will not bind to or activate the VEGFR-2.

Alternatively, recombinant VEGF-C protein or active peptide fragment mutants or variants, which preferentially bind to the VEGFR-3, but not the VEGFR-2 are also useful for carrying out the methods of the present invention. Exemplary VEGF-C mutants or variants include those recombinant proteins or peptide fragments having a cysteine to serine substitution at amino acid position 156 (C156S) of SEQ ID NO:2 (Joukov et al., "A Recombinant Mutant Vascular Endothelial Growth Factor-C that has Lost Vascular Endothelial Growth Factor Receptor-2 Binding, Activation, and Vascular Permeability Activities," *J. Biol. Chem.* 273(12): 6599-6602 (1998), which is hereby incorporated by reference in its entirety) or position 162 (C162S) of SEQ ID NO: 2. Alternatively, the recombinant VEGF-C protein or peptide fragment may have a cysteine to serine substitution at amino acid position 152 (C152S) of SEQ ID NO:4 (Suzuki et al., "Roles of Vascular Endothelial Growth Factor Receptor-3 Signaling in Differentiation of Mouse Embryonic Stem Cell-Derived Vascular Progenitor Cells into Endothelial Cells," *Blood* 105(6):2372-2379 (2005), which is hereby incorporated by reference in its entirety) or position 158 (C158S) of SEQ ID NO: 4. Additional VEGF-C mutants and variants useful in the methods of the present invention are described in International Patent Publication No. WO 98/33917 to Alitalo et al., which is hereby incorporated by reference in its entirety.

In an alternative embodiment of the present invention, the therapeutic agent is a nucleic acid molecule encoding a VEGF3R agonist. Preferably, the nucleic acid molecule encodes a VEGF-C protein or active fragment or derivative thereof. More preferably, the nucleic acid molecule encodes a VEGF-C protein or active fragment or derivative thereof that preferentially binds the VEGFR3 and does not bind to or activate the VEGFR2. An exemplary nucleic acid encoding a VEGFR-3 agonist molecule is one which encodes only a partial sequence of the VEGF-C protein corresponding to the partially processed form of VEGF-C (i.e. the 29 kD form described supra) which does not bind VEGFR-2. Alternatively, the nucleic acid encoding the VEGFR-3 agonist molecule encodes the C156S VEGF-C mutant protein or active peptide fragment or derivative, or the C152S VEGF-C mutant protein or active peptide fragment or derivative.

The nucleic acid encoding the VEGFR3 agonist molecules of the invention can be incorporated into a gene therapy or recombinant expression vector. Such vectors, when delivered to the specific target cells and/or tissue will facilitate production of agonist polypeptides to stimulate the activity of VEGFR-3 and will provide useful therapy for inflammatory conditions of the joint, such as rheumatoid arthritis. Delivery of a functional gene encoding polypeptides of the invention to appropriate cells can be achieved ex vivo, in situ, or in vivo by use of vectors, including viral vectors (e.g., adenovirus, adeno-associated virus, or a retrovirus), or ex vivo by use of physical DNA transfer methods (e.g., liposomes or chemical treatments). To facilitate in vivo delivery and expression of the nucleic acid molecules of the invention, the nucleic acid can further include a promoter that is operable in mammalian cells. This promoter can be a constitutively active promoter or a promoter having tissue specific expression. Promoters having tissue specific expression are particularly suitable for targeting the expression of the nucleic acid molecule to only the tissue and cells associated with the inflammatory condition. In a preferred embodiment, the nucleic acid molecules of the present invention contain a promoter specific for cytokine or metalloproteinase production, a macrophage specific promoter (e.g., CD14 or CD68), or a fibroblast specific promoter, allowing enhanced targeting to activated synoviocytes and leave normal resting cells unaffected. For additional reviews of gene therapy technology see Anderson et al., "Human Gene Therapy," *Nature, S*392 (6679):25-20 (1998); Friedmann et al., "Progress Toward Human Gene Therapy," *Science* 244:1275-1281 (1989); Verma et al., "Gene Therapy," *Scientific American* 263:68-72, 81-84 (1990); and Miller et al., "Human Gene Therapy Comes of Age," *Nature* 357:455-460 (1992), which are all hereby incorporated by reference in their entirety.

Introduction of any one of the nucleotides encoding a VEGFR-3 agonist of the present invention can also be accomplished with extrachromosomal substrates (transient expression) or artificial chromosomes (stable expression). Cells may also be cultured ex vivo in the presence of VEGF-C or VEGFR3 agonists of the present invention to induce the desired effect on cells. In another embodiment, cells comprising vectors expressing VEGFR-3 agonist polynucleotides or polypeptides of the invention may be cultured ex vivo and administered to an individual in need of treatment for chronic rheumatoid arthritis or other inflammatory conditions. Cells treated with VEGFR-3 agonist polypeptides, or proliferating cells carrying VEGFR-3 agonist expression vectors can then be introduced in vivo for therapeutic purposes.

Further contemplated are recombinant expression vectors comprising at least a fragment of the nucleic acid molecules, particularly those encoding VEGF-C protein or active fragments as set forth above, and host cells or organisms transformed with these expression vectors. Useful vectors include plasmids, cosmids, lambda phage derivatives, phagemids, and infective transformation vectors that are well known in the art. Accordingly, the invention also provides a vector including the nucleic acid molecules of the invention and a host cell containing the nucleic acid molecules. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

Any suitable viral or infective transformation vector can be used to deliver a nucleotide encoding a VEGFR-3 agonist of the present invention. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α1-Antitrypsin Gene to the Lung Epithelium in vivo," *Science* 252:431-434 (1991); International Patent Publication No. WO 1993/007283 to Curiel et al.; International Patent Publication No. WO 1993/006223 to Perricaudet et al.; and International Patent Publication No. WO1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid. The use of adeno-associated viral gene delivery vehicles in vitro is described infra and in Chatterjee et al., "Dual-Target Inhibition of HIV-1 in vitro by Means of an Adeno-associated Virus Antisense Vector," *Science* 258:1485-8 (1992); Walsh et al., "Regulated High Level Expression of a Human γ-Globin Gene Introduced into Erythroid Cells by an Adeno-associated Virus Vector," *Proc. Nat'l Acad. Sci. USA* 89:7257-61 (1992); Walsh et al., "Phenotypic Correction of Fanconi Anemia in Human Hematopoietic Cells with a Recombinant Adeno-associated Virus Vector," *J. Clin. Invest.* 94:1440-8 (1994); Flotte et al., "Expression of the Cystic Fibrosis Transmembrane Conductance Regulator from a Novel Adeno-associated Virus Promoter," *J. Biol. Chem.* 268:3781-90 (1993); Ponnazhagan et al., "Suppression of Human α-Globin Gene Expression Mediated by the Recombinant Adeno-associated Virus 2-based Antisense Vectors," *J. Exp. Med.* 179:733-8 (1994); Miller et al., "Recombinant Adeno-associated Virus (rAAV)-mediated Expression of a Human γ-Globin Gene in Human Progenitor-derived Erythroid Cells," *Proc. Nat'l Acad. Sci. USA* 91:10183-7 (1994); Einerhand et al., "Regulated High-level Human β-Globin Gene Expression in Erythroid Cells Following Recombinant Adeno-associated Virus-mediated Gene Transfer," *Gene Ther.* 2:336-43 (1995); Luo et al., "Adeno-associated Virus 2-mediated Gene Transfer and Functional Expression of the Human Granulocyte-macrophage Colony-stimulating Factor," *Exp. Hematol.* 23:1261-7 (1995); and Zhou et al., "Adeno-associated Virus 2-mediated Transduction and Erythroid Cell-specific Expression of a Human β-Globin Gene," *Gene Ther.* 3:223-9 (1996), which are hereby incorporated by reference in their entirety. In vivo use of these vehicles is described infra and in Flotte et al., "Stable in Vivo Expression of the Cystic Fibrosis Transmembrane Conductance Regulator with an Adeno-associated Virus Vector," *Proc. Nat'l Acad. Sci. USA* 90:10613-7 (1993), and Kaplitt et al., "Long-term Gene Expression and Phenotypic Correction Using Adeno-associated Virus Vectors in the Mammalian Brain," *Nat. Genet.* 8:148-54 (1994), which are hereby incorporated by reference in their entirety.

Retroviral vectors which have been modified to form infective transformation systems can also be used to deliver a recombinant gene encoding the VEGF-C nucleic acid product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

In another embodiment, the therapeutic agent of the present invention is a small molecule VEGFR-3 agonist. Small molecules of the present invention are entities having carbon and hydrogen atoms, as well as heteroatoms, which include, but are not limited to, nitrogen, sulfur, oxygen, and phosphorus. Atoms in a small molecule are linked together via covalent and ionic bonds; the former is typical for small organic compounds and the latter is typical of small inorganic compounds. The arrangement of atoms in a small organic molecule can represent a chain, e.g., a carbon-carbon chain or carbon-heteroatom chain, or ring containing carbon atoms, e.g., benzene, or a combination of carbon and heteroatoms, i.e., heterocycles, for example, a pyrimidine or quinazoline. A combination of one or more chains in a small organic molecule attached to a ring system constitutes a substituted ring system and fusion of two rings constitutes a fused policyclic system, which can be referred to as simply a policyclic system. Small molecules include both compounds found in nature, such as hormones, neurotransmitters, nucleotides, amino acids, sugars, lipids and their derivatives, and those compounds made synthetically, either by traditional organic synthesis, bio-mediated synthesis, or a combination thereof. See, e.g., Ganesan et al., "Recent Developments in Combinatorial Organic Synthesis," *Drug Discov. Today* 7(1): 47-55 (2002); Lou et al., "Novel Strategies for Solid-Phase Construction of Small-Molecule Combinatorial Libraries," *Drug Discov. Today* 6(24): 1288-1294 (2001). Furthermore, small molecules include, for example, lipids and polymers of polysaccharides, as well as derivatives thereof, such as, e.g., lipopolysaccharides. Any suitable small molecule that activates the VEGFR3 can be used in the context of the present invention.

In accordance with the methods of the present invention, the VEGFR-3 agonist can be administered to a patient suffering from an inflammatory condition in combination with an agent that inhibits VEGF or an agent that antagonizes the VEGF/VEGFR-1 or VEGFR2 interaction and/or signaling pathway.

Agents which inhibit VEGF directly or interfere with its signaling through VEGFR1 or R2 are well known in the art. For example antibodies directed to VEGF, VEGFR1, VEGFR2, or the VEGF-VEGFR1 or VEGF-VEGFR2 complex are described in U.S. Patent Publication No. 20020032313 to Ferrara et al., which is hereby incorporated by reference in its entirety. Such antibodies can be monoclonal or polyclonal antibodies. Antibodies can also be variant antibodies, such as chimeric (including "humanized") antibodies and hybrid antibodies comprising immunoglobulin chains capable of binding VEGF, VEGFR1 or VEGR2, or the VEGF-VEGFR complexes, and a non-VEGF epitope. The antibodies herein include all species of origin, however, it is preferably that the antibody is a humanized antibody recognizing antigenic components of the human VEGF protein or human VEGFR1 or VEGFR2 proteins. The antibodies include all immunoglobulin classes (e.g., IgA, IgD, IgE, IgG, and IgM) and subclasses, as well as antibody fragments, so long as they are capable of binding VEGF, VEGFR1 or R2, or the VEGF-VEGFR1 or R2 complex, and are capable of antagonizing a biological activity of VEGF.

Antibody fragments comprise only a portion of an intact antibody, generally including an antigen binding site of the intact antibody and thus retaining the ability to bind antigen. Examples of antibody fragments encompassed by the present invention include: the Fab fragment, having a light chain variable domain (VL), light chain constant domain (CL), heavy chain variable domain (VH), and heavy chain constant domain (CH1); the Fab' fragment, which is a Fab fragment having one or more cysteine residues at the C-terminus of the CH1 domain; the Fd fragment having VH and CH1 domains; the Fd' fragment having VH and CH1 domains and one or more cysteine residues at the C-terminus of the CH1 domain; the Fv fragment having the VL and VH domains of a single arm of an antibody; the dAb fragment (Ward et al., "Binding Activities of a Repertoire of Single Immunoglobulin Variable Domains Secreted from *Escherichia coli*," *Nature* 341:544-546 (1989), which is hereby incorporated by reference in its entirety) which consists of a VH domain; isolated CDR regions; F(ab')$_2$ fragments, a bivalent fragment including two Fab' fragments linked by a disulphide bridge at the hinge region; single chain antibody molecules (Bird et al., "Single-Chain Antigen Binding Proteins," *Science* 242:423-426 (1988); and Huston et al., "Protein Engineering of Antibody Binding Sites: Recovery of Specific Activity in an Anti-Digoxin Single-Chain Fv Analogue Produced in *Escherichia coli*," *PNAS* 85:5879-5883 (1988), which are hereby incorporated by reference in their entirety); diabodies with two antigen binding sites, comprising a VH domain connected to a VL domain in the same polypeptide chain (see, e.g., WO 93/11161 to Whitlow et al. and Hollinger et al., "Diabodies: Small Bivalent and Bispecific Antibody Fragments," *PNAS* 90:6444-6448 (1993), which are hereby incorporated by reference in their entirety); and linear antibodies comprising a pair of tandem Fd segments (VH-CH1-VH-CH1) which, together with complementary light chain polypeptides, form a pair of antigen binding regions (Zapata et al., "Engineering Linear F(ab')2 Fragments for Efficient Production in *Escherichia coli* and Enhanced Antiproliferative Activity," *Protein Eng.* 8(10): 1057-1062 (1995); and U.S. Pat. No. 5,641,870 to Rinderknecht et al., which are hereby incorporated by reference in their entirety).

VEGF inhibitors of the present invention also include inhibitory proteins or polypeptide fragments. One exemplary class of VEGF inhibitor proteins include proteins or polypeptides comprising a soluble VEGFR-1 or VEGFR-2 fragment (e.g., an extracellular domain fragment), wherein the fragment and the polypeptide are capable of binding to VEGF thereby preventing its endogenous binding to its respective receptor. Examples of such soluble VEGFR1 and R2 are set forth in U.S. Patent Publication No. 20030120038 to Kendall et al., which is hereby incorporated by reference in its entirety.

An alternative class of VEGF/VEGFR inhibitor proteins include polypeptides comprising an antigen binding fragment of an anti-VEGF or anti-VEGFR1 or R2 antibody. Also contemplated are polypeptides comprising a fragment or analog of a mammalian VEGF polypeptide, wherein the polypeptide, fragment or analog bind, but fail to activate, the VEGFR-1 or VEGFR-2 expressed on native host cells (i.e., cells of the organism that express the native VEGFR1 or R2 protein on their surface). Exemplary inhibitory VEGF variant proteins are described in U.S. Patent Publication Nos. 20060286636 to Shima et al. and 20050154187 to Shou et al., which are hereby incorporated by reference in their entirety. Inhibitory fusion proteins directed to VEGF and VEGFR molecules as described in U.S. Patent Publication No. 20070253952 to Alvarez Vallina et al., which is hereby incorporated by reference in its entirety, are also useful agents for antagonizing the VEGF signaling pathway for purposes of the present invention.

VEGF signaling inhibitors can also include nucleic acid molecules, such as a VEGF, VEGFR1 or VEGFR2 antisense polynucleotide or siRNA. Alternatively, the nucleic acid molecule inhibitor of the present invention can encode the inhibitory antibody, protein or polypeptide inhibitor described supra. Suitable therapeutic nucleic acid molecules also include aptamers.

Aptamers are single-stranded, partially single-stranded, partially double-stranded, or double-stranded nucleotide sequences, advantageously a replicatable nucleotide sequence, capable of specifically recognizing a selected nonoligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence. A suitable VEGF aptamer for use in the present invention is pegaptanib, an RNA aptamer directed against VEGF-165 (Ng et al., "Pegaptanib, A Targeted Anti-VEGF Aptamer for Ocular Vascular Disease," *Nat Rev Drug Discov* 5(2): 123-32 (2006), which is hereby incorporated by reference in its entirety).

Small molecule inhibitors of VEGF, VEGFR1, or VEGFR2 are also useful in the methods of the present invention. Such inhibitors are readily identifiable by standard in vitro screening assays, e.g., using VEGF and recombinantly expressed VEGFR1 or R2. Suitable VEGF inhibitors include CP-547, 632 (Pfizer Inc., NY, USA), AG13736 (Pfizer Inc.), ZD-6474 (AstraZeneca), AEE788 (Novartis), AZD-2171), VEGF Trap (Regeneron/Aventis), Vatalanib (also known as PTK-787, ZK-222584: Novartis & Schering AG), IM862 (Cytran Inc. of Kirkland, Wash., USA); and angiozyme, a synthetic ribozyme from Ribozyme (Boulder, Colo.) and Chiron (Emeryville, Calif.). Additional VEGF inhibitors suitable for use in the present invention are disclosed in U.S. Pat. No. 6,534,524 to Kania et al., and U.S. Pat. No. 6,235,764 to Larson et al., which are hereby incorporated by reference in their entirety. Examples of small molecule VEGFR1 and R2 antagonists are also described by U.S. Patent Publication No. 20070135489 to Huth et al., which is hereby incorporated by reference in its entirety.

The therapeutic VEGFR3 agonist of the present invention can also be administered to the patient in combination with a traditional anti-inflammatory medication, an inhibitor of TNFα, or a combination thereof. This can be in addition to, or as an alternative to, the combination of the VEGFR3 agonist with the VEGF, VEGFR1, or VEGFR2 antagonist.

Exemplary anti-inflammatory medications include, but are not limited to, non-steroidal anti-inflammatory drugs (NSAID), analgesics, glucocorticoids, disease-modifying anti-rheumatic drugs, dihydrofolate reductase inhibitors (e.g., methotrexate), biologic response modifiers, and any combination thereof.

When the therapeutic VEGF-C agonist agent of the present invention is administered in combination with an NSAID, the NSAID is preferably a selective cyclooxygenase-2 (COX-2) inhibitor. Exemplary COX-2 inhibitors include, without limitation, nimesulide, 4-hydroxynimesulide, flosulide, meloxicam, celecoxib, and Rofecoxib (Vioxx). Alternatively, a non-selective NSAID inhibitor is administered in combination with the VEGF-C agonist agent of the present invention. Exemplary non-selective NSAIDS inhibitors include, without limitation, diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac and tolmetin.

When the therapeutic VEGF-C agonist agent of the present invention is administered in combination with an analgesic, preferred analgesics include, without limitation, acetaminophen, oxycodone, tramadol, and propoxyphene hydrochloride.

When administering the therapeutic VEGF-C agonist agent of the present invention in combination with a glucocorticoid, preferred glucocorticoids include, without limitation, cortisone, dexamethosone, hydrocortisone, methylpredisolone, prednisolone, and prednisone.

When administering the therapeutic VEGF-C agonist agent of the present invention in combination with a biological response modifier, that modifier may be a B-cell inhibitor, such as Rituximab, or a T cell activation inhibitor. Common T-cell activation inhibitors include, without limitation, Leflunomide, Etanercept (Enbrel), or Infliximab (Remicade).

When administering the therapeutic VEGF-C agonist agent of the present invention in combination with a TNFα inhibitor, the inhibitor can be a TNF-α antibody, a matrix metalloproteinase inhibitor, a corticosteroid, a tetracycline TNF-α antagonist, a fluoroquinolone TNF-α antagonist, and a quinolone TNF-α antagonist. Exemplary TNF-α antagonist antibodies include, without limitation, infliximab, etanercept, CytoFAb, AGT-1, afelimomab, PassTNF, and CDP-870. Exemplary corticosteroids include, without limitation, mometasone, fluticasone, ciclesonide, budesonide, beclomethasone, beconase, flunisolide, deflazacort, betamethasone, methyl-prednisolone, dexamethasone, prednisolone, hydrocortisone, cortisol, triamcinolone, cortisone, corticosterone, dihydroxycortisone, beclomethasone dipropionate, and prednisone. Exemplary tetracycline TNF-α antagonists include, without limitation, doxycycline, minocycline, oxytetracycline, tetracycline, lymecycline, and 4-hydroxy-4-dimethylaminotetracycline.

Exemplary fluoroquinolone TNF-α antagonists include, without limitation, norfloxacin, ofloxacin, ciprofloxacin, lomefloxacin, gatifloxacin, perfloxacin, and temafloxacin. Exemplary quinolone TNF-α antagonists include, without limitation, vesnarinone and amrinone. Other TNF-α antagonists include, without limitation, thalidomide, Onercept, Pegsunercept, interferon-gamma, interleukin-1, pentoxyphylline, pimobeddan, lactoferrin, melatonin, nitrogen oxide, napthopyridine, a lazaroid, hydrazine sulfate, ketotifen, tenidap, a cyclosporin, peptide T, sulfasalazine, thorazine, glycyrrhizin, and L-carnitine The therapeutic agents of the present invention may be administered in any suitable or medically-accepted means for introducing a therapeutic directly or indirectly into a mammalian subject, including but not limited to orally, subcutaneously, intravenously, intramuscularly, parenterally, intrasynovially, intra-articularly, intraperitoneally, topically, transdermally, or by application to a mucosal surface. In a preferred embodiment of the present invention, the therapeutic agent is administered intrasynovially. The therapeutic composition may be delivered to the patient at multiple sites. The multiple administrations may be rendered simultaneously or over a period of several hours. In certain cases it may be beneficial to provide a continuous flow of the therapeutic composition. Additional therapy may be administered on a period basis, for example, daily, weekly or monthly.

The therapeutic proteins, peptides, nucleic acid molecules, or small molecules for administration may be formulated with uptake or absorption enhancers to increase their efficacy. Such enhancer include for example, salicylate, glycocholate/linoleate, glycholate, aprotinin, bacitracin, SDS caprate and the like (see e.g., Fix et al., "Strategies for Delivery of Peptides Utilizing Absorption-Enhancing Agents," *J. Pharm. Sci.*, 85:1282-1285 (1996); and Oliyai and Stella, "Prodrugs of Peptides and Proteins for Improved Formulation and Delivery," *Ann. Rev. Pharmacol. Toxicol.* 33:521-544 (1993), which are hereby incorporated by reference in their entirety).

The amount of peptides in a given dosage will vary according to the size of the individual to whom the therapy is being administered as well as the characteristics of the disorder being treated. In exemplary treatments, it may be necessary to administer about 50 mg/day, 75 mg/day, 100 mg/day, 150 mg/day, 200 mg/day, 250 mg/day. These concentrations may be administered as a single dosage form or as multiple doses. Standard dose-response studies, first in animal models and then in clinical testing, will reveal optimal dosages for particular disease states and patient populations.

It will also be apparent that dosing should be modified if the VEGFR3 agonist is administered in combination with either the VEGF, VEGFR1, or VEGFR2 antagonist and/or with traditional inflammatory medications, such as those described supra.

In one embodiment of the present invention, suitable dosing and/or the effectiveness of therapy can be monitored in an individual subject by measuring lymph node capacity (LNcap). As described in the examples below, LNcap can be used as a surrogate marker for lymphatic drainage. Enhanced lymphatic drainage, i.e. increased LNcap, can be indicative of a suitable dosing regimen and an effective therapeutic response.

Another aspect of the present invention is directed to a pharmaceutical composition. This pharmaceutical composition includes a pharmaceutically acceptable carrier along with a therapeutic agent that is a VEGFR-3 agonist or a nucleic molecule encoding a VEGFR-3 agonist and one or more additional therapeutic agents.

The individual components of the pharmaceutical composition of the present invention, i.e., the VEGFR3 agonist, the VEGF, VEGFR1 or VEGFR2 antagonist, and the additional therapeutic agents can be any of those described supra.

The pharmaceutical composition of the present invention also contains a carrier. Acceptable pharmaceutical carriers include solutions, suspensions, emulsions, excipients, powders, or stabilizers. The carrier should be suitable for the desired mode of delivery, discussed infra.

Pharmaceutical compositions suitable for injectable use (e.g., intravenous, intrasynovial, intra-arterial, intramuscular, etc.) may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable carriers and/or excipients, include, but are not limited to sterile liquids, such as water and oils, with or without the addition of a surfactant and other pharmaceutically and physiologically acceptable carrier. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

Oral dosage formulations of the pharmaceutical composition of the present invention can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

As is known in the art, because orally administered agents need to survive the digestive system before cellular uptake, it is possible to administer the therapeutic agents of the present invention with any of a variety of stabilizing reagent that inhibits destruction thereof. One such type of stabilizing reagent is a mammalian colostrum, whether produced as a hyperimmune colostrum for antibody-based therapeutics or as an in vitro mixture of the therapeutic agent and colostrum.

An additional aspect of the present invention relates to a therapeutic system for treating an anti-inflammatory condition. This therapeutic system includes a first pharmaceutical composition comprising a pharmaceutically acceptable carrier and a therapeutic agent that is a VEGFR-3 agonist or a nucleic molecule encoding a VEGFR-3 agonist. The therapeutic system also includes a second pharmaceutical composition comprising a pharmaceutically acceptable carrier and one or more additional therapeutic agents. The additional therapeutic agents can include a VEGF, VEGFR-1 or VEGFR-2 antagonist, an agent that interferes with VEGF/VEGFR-1 or 2 interaction, an NSAID, an analgesic, a glucocorticoid, a disease-modifying anti-rheumatic drug, a dihydrofolate reductase inhibitor (e.g., methotrexate), a biological response modifier, or any combination thereof.

The first and second pharmaceutical compositions of the therapeutic system can be any of those described supra.

In one preferred embodiment, the pharmaceutical composition or therapeutic system includes a VEGFR-3 agonist or nucleic acid molecule encoding a VEGFR-3 agonist in combination with a VEGF, VEGFR-1, or VEGFR-2 antagonist or an agent that interferes with VEGF/VEGFR-1 or 2 interaction as described above.

In another preferred embodiment, the pharmaceutical composition or therapeutic system includes a VEGFR-3 agonist or nucleic acid molecule encoding a VEGFR-3 agonist in combination with an NSAID (preferably one of those described above).

In an alternative embodiment, the pharmaceutical composition or the therapeutic system includes a VEGFR-3 agonist or nucleic acid molecule encoding a VEGFR-3 agonist in combination with a biological response modifier, including the B-cell inhibitors and T cell activation inhibitors as described above.

In an alternative embodiment, the pharmaceutical composition or the therapeutic system includes a VEGFR-3 agonist or nucleic acid molecule encoding a VEGFR-3 agonist in combination with a TNF-α inhibitor, including any of the TNF-α inhibitors described above As described supra, the pharmaceutical composition or the therapeutic system of the present invention are suitable for administering orally, subcutaneously, intravenously, intramuscularly, parenterally, intrasynovially, intra-articularly, intraperitoneally, topically, transdermally, or by application to a mucosal surface as described above.

EXAMPLES

The following examples are provided to illustrate embodiments of the present invention but they are by no means intended to limit its scope.

Materials and Methods for Examples 1-5

Animals. TNF-Tg mice (Tg 3647 line) in a CBA×C57BL/6 background were originally obtained from George Kollias (The Biomedical Sciences Research Center, Greece). These mice were backcrossed with C57BL6 mice for seven generations (Li et al., "Systemic Tumor Necrosis Factor Alpha Mediates an Increase in Peripheral CD11b-high Osteoclast Precursors in Tumor Necrosis Factor Alpha-Transgenic Mice," *Arthritis Rheum* 50:265-276 (2004), which is hereby incorporated by reference in its entirety). All TNF-Tg mice used in Examples 1-5 were 4 to 8 months old with severe joint synovitis and bone and cartilage destruction. Wildtype (WT) littermates were used as controls. TNF-Tg mice were identified by tail polymerase chain reaction (PCR) genotyping and paw deformation. KRN-TCR-Tg mice were obtained from Drs. Diane Mathis and Christophe Benoist (Harvard University, Cambridge, Mass., USA) (Kouskoff et al., "Organ-Specific Disease Provoked by Systemic Autoimmunity," Cell 87:811-822 (1996), which is hereby incorporated by reference in its entirety). K/BxN mice were generated by breeding male KRN-TCR-Tg mice with female non-obese diabetic mice (The Jackson Laboratory, Bar Harbor, Me., USA). Serum was collected from 6- to 12-week-old K/BxN arthritic mice, pooled, and stored at −80° C. To generate mice with serum-induced arthritis (SIA), 4- to 5-week-old BALB/c mice were injected with K/BxN serum intraperitoneally (10 µL/gram body weight) on day 1 and day 3. Paw swelling and redness usually occurred the day after the first injection, peaked at 7 to 14 days, and declined thereafter. The Institutional Animal Care and Use Committee of the University of Rochester (Rochester, N.Y., USA) approved all studies.

Reagents. Recombinant murine TNF-α was purchased from R&D Systems, Inc. (Minneapolis, Minn., USA). Allophycocyanin-, fluorescein isothiocyanate (FITC)-, and phycoerythrin-anti-mouse CD11b (M1/70) were purchased from eBiosciences (San Diego, Calif., USA); FITC-anti-mouse Gr-1 (RB6-8C5) from BD Pharmingen (San Diego, Calif., USA); rabbit polyclonal antibody to VEGF-C (H-190) from Santa Cruz Biotechnology, Inc. (Santa Cruz, Calif., USA); rabbit polyclonal antibody to LYVE-1 from Abcam (Cambridge, Mass., USA); mouse monoclonal antibody to CD31 (Mec13.3) from Biocare Medical LLC (Concord, Calif., USA); Alexa Fluor 488 goat anti-hamster immunoglobulin G (IgG) from Molecular Probes Inc. (now part of Invitrogen Corporation, Carlsbad, Calif., USA); and Alexa Fluor 546 F(ab')$_2$ fragment of goat anti-rabbit IgG (H+L) and TO-PRO-3 iodide (642/661) were purchased from Invitrogen Corporation.

Generation of Osteoclast Precursors (OCPs). OCPs were generated from splenocytes of 8- to 12-week-old C57/B6 WT mice. Splenocytes were extracted through a fine wire mesh, and red blood cells were lysed with $NH_4Cl$ (StemCell Technologies, Vancouver, BC, Canada) on ice for 10 minutes. The cells were washed twice with medium and cultured with conditioned medium from a macrophage colony-stimulating factor (M-CSF)-producing cell line (1:20 dilution) (Takeshita et al., "Identification and Characterization of the New Osteoclast Progenitor with Macrophage Phenotypes Being Able to Differentiate into Mature Osteoclasts," J Bone Miner Res 15:1477-1488 (2000), which is hereby incorporated by reference in its entirety) for 3 days to enrich for OCPs, as described previously (Zhang et al., "Tumor Necrosis Factor Prevents Alendronate-Induced Osteoclast Apoptosis in vivo by Stimulating Bcl-xL Expression Through Ets-2," Arthritis Rheum 52:2708-2718 (2005), which is hereby incorporated by reference in its entirety). OCPs from ankle and wrist joints were isolated from TNF-Tg mice and WT littermates according to published protocols (Brühl et al., "Dual Role of CCR2 During Initiation and Progression of Collagen-Induced Arthritis: Evidence for Regulatory Activity of CCR2+ T Cells," J Immunol 172:890-898 (2004); Kamata et al., "Involvement of TNF-like Weak Inducer of Apoptosis in the Pathogenesis of Collagen-Induced Arthritis," J Immunol 177:6433-6439 (2006), which are hereby incorporated by reference in their entirety) with minor modifications. In brief, mice were sacrificed and skin and muscle were removed from their limbs. Long bones together with a front or rear paw were cut from the limbs. Forceps were used to loosen the joints. The joints were cut open and digested with 1 mg/mL of collagenase (Sigma-Aldrich, St. Louis, Mo., USA) at 37° C. for 3 hours with rotation. Cells were then filtered and used for cultures or FACS analysis.

Affymetrix Gene Chip Analysis. $CD11b^+/Gr-1^{-/lo}$ OCPs were purified by flow sorting from peripheral blood and bone marrow of TNF-Tg mice and age-matched WT mice by a FACSVantage SE Turbo sorter (Becton, Dickinson and Company, Franklin Lakes, N.J., USA), as described previously (Li et al., "Systemic Tumor Necrosis Factor Alpha Mediates an Increase in Peripheral CD11b-high Osteoclast Precursors in Tumor Necrosis Factor Alpha-Transgenic Mice," Arthritis Rheum 50:265-276 (2004); Yao et al., "Tumor Necrosis Factor-α Increases Circulating Osteoclast Precursor Numbers by Promoting Their Proliferation and Differentiation in the Bone Marrow through Up-Regulation of c-Fms Expression," J Biol Chem 281:11846-11855 (2006), which are hereby incorporated by reference in their entirety). To obtain enough RNA from samples, bone marrow OCPs were pooled from 7 TNF-Tg mice or 11 WT mice and peripheral blood OCPs were from pooled from 7 TNF-Tg mice or 23 WT mice. Two completely independent experiments were performed. Total RNA was prepared using TRIzol (Invitrogen Corporation), processed, and hybridized to MG-U74Av2 gene chips according to Affymetrix protocols (Affymetrix, Santa Clara, Calif., USA). Chips were scanned and analyzed using the GeneTraffic (version 3.2) microarray data analysis software (Lobion Informatics, La Jolla, Calif., USA). In each group, WT samples were set as the baseline. Data were presented as the fold increase of samples from TNF-Tg mice over WT samples (baseline sample).

Real-Time Quantitative Reverse Transcription-Polymerase Chain Reaction. Total RNA was extracted using TRIzol reagent, and cDNA was synthesized by an RNA PCR Core Kit (Applied Biosystems, Foster City, Calif., USA). Quantitative PCR amplification was performed with gene-specific primers using an iCycler iQ Multiple-Color Real-Time PCR Detection System (Bio-Rad Laboratories, Inc., Hercules, Calif., USA), as described previously (Zhang et al., "Tumor Necrosis Factor Prevents Alendronate-Induced Osteoclast Apoptosis in vivo by Stimulating Bcl-xL Expression Through Ets-2," Arthritis Rheum 52:2708-2718 (2005); Yao et al., "Tumor Necrosis Factor-α Increases Circulating Osteoclast Precursor Numbers by Promoting Their Proliferation and Differentiation in the Bone Marrow through Up-Regulation of c-Fms Expression," J Biol Chem 281:11846-11855 (2006), which are hereby incorporated by reference in their entirety). The primer sequences are listed in Table 1. Expression levels were normalized relative to β-actin in the same sample. Relative fold expression for each sample was calculated using the Comparative $C_T$ method as described in Applied Biosystems User Bulletin #2 for the ABI Prism 7700

TABLE 1

Sequences of Primers used in the Real-Time RT PCR

| Genes | Sequences of primers | Product sizes (bp) | SEQ ID NO |
|---|---|---|---|
| VEGF-A | F: 5' TTTACTGCTGTACCTCCACCA 3'<br>R: 5' ATCTCTCCTATGTGCTGGCTTT 3' | 298 | 5<br>6 |

TABLE 1-continued

Sequences of Primers used in the Real-Time RT PCR

| Genes | Sequences of primers | Product sizes (bp) | SEQ ID NO |
|---|---|---|---|
| VEGF-B | F: 5' CCTGGAAGAACACAGCCAAT 3'<br>R: 5' GGAGTGGGATGGATGATGTC 3' | 165 | 7<br>8 |
| VEGF-C | F: 5' GGGAAGAAGTTCCACCATCA 3'<br>R: 5' ATGTGGCCTTTTCCAATACG 3' | 135 | 9<br>10 |
| VEGF-D | F: 5' GCTGTCACTGTTGCCCACTA 3'<br>R: 5' CCCTTCCTTTCTGAGTGCTG 3 | 189 | 11<br>12 |
| PLGF | F: 5' GGGAAGAAGCAAGACATGGA 3'<br>R: 5' ATGTCCTGTCCCATCTCCAG 3' | 207 | 13<br>14 |
| β-actin | F: 5' ACCCAGATCATGTTTGAGAC 3'<br>R: 5' GTCAGGATCTTCATGAGGTAGT 3' | 224 | 15<br>16 |

F: forward primer, R: reverse primer
Primer target site and gene accession number for each gene is as follows:
VEGFA-nucleotides 125-423 of Accession No. M95200; VEGEB-nucleotides 537-701 of Accession No. NM_011697 VEGFC-nucleotides 1258-1392 of Accession No. NM_009506; VEGED-nucleotides 1423-1611 of Accession No. NM_010216; PLGF-nucleotides 1055-1261 of Accession No. NM_008827; Beta-Actin-nucleotides 280-503 of Accession No. X03765

Sequence Detection System (updated October, 2001), which is hereby incorporated by reference in its entirety.

Immunofluorescence Staining and Imaging Cytometry. Cells were cytospun on glass slides and fixed by cold methanol at −20° C. for 10 minutes. After washing with PBS, cells were incubated in 0.1% Triton and blocked with 1% bovine serum albumin/PBS for 30 minutes at room temperature. The fixed cells were stained with a mixture of FITC-anti-CD11b and anti-VEGF-C antibody followed by Alexa Fluor 546 F(ab')$_2$ fragment of goat anti-rabbit IgG (H+L). TO-PRO-3 iodide was used for nuclear staining.

Immunohistomorphometry of Lymphatic Vessels. Joint tissue sections from TNF-Tg and WT mice were fixed in 4.5% phosphate-buffered formalin, decalcified in 14% ethylenediaminetetraacetic acid (EDTA), and embedded in paraffin wax. Deparaffinized sections were quenched with 3% hydrogen peroxide and treated for antigen retrieval for 30 minutes. Adjacent serial sections were stained with anti-LYVE-1 (lymphatic vessel endothelial hyaluronan receptor) or anti-CD31 antibodies. Lymphatic vessels were quantified by a point-counting method, as described previously (Boyce B. F., "Bone Biopsy and Histomorphometry in Metabolic Bone Disease," In New Techniques in Metabolic Bone Disease pp. 110-131 (J C Stevens ed., 1990), which is hereby incorporated by reference in its entirety). For each mouse, the area and size of LYVE-1$^+$ lymphatic vessels were measured within the synovial tissue of serial sections (250 μm). The size and area of lymphatic vessels were expressed per square millimeter of synovium.

Electrophoretic Mobility Shift Assay. Raw 264.7 osteoclast/macrophage precursor cells were serum-starved overnight and then treated with 10 ng/mL of TNF for 30 and 60 minutes. Nuclear extract preparation and electrophoretic mobility shift assay (EMSA) were performed as described previously (Feng et al., "NF-KappaB Specifically Activates BMP-2 Gene Expression in Growth Plate Chondrocytes In Vivo and in a Chondrocyte Cell Line In Vitro," *J Biol Chem* 278:29130-29135 (2003), which is hereby incorporated by reference in its entirety). The following double-stranded oligonucleotides were used in this study according to the published mouse VEGF-C promoter sequence (Chilov et al., "Genomic Organization of Human and Mouse Genes for Vascular Endothelial Growth Factor-C," *J Biol Chem* 272: 25176-25183 (1997), which is hereby incorporated by reference in its entirety) (only the top strands are shown in FIG. 3B): VEGF-C nuclear factor-kappa B (NF-κB)-like sequence (WT), 5'-GCCCAGGGGGGTCCCCGGGAGG-3' (SEQ ID NO: 17); mutated VEGF-C NF-κB-like sequence (mutation italicized), 5'-GCCCAGGGGATTCTCCGGGAGG-3' (SEQ ID NO:18); and SP-1-binding sequence (control; Invitrogen Corporation), 5'-CGAGCCGGCCCCGCCCATC-3' (SEQ ID NO: 19). For competition assays, binding reactions were pre-incubated with unlabeled oligonucleotides for 15 minutes at room temperature.

In vivo Contrast-Enhanced Magnetic Resonance Imaging. A detailed methodology of this technique is described by (Proulx et al., "Longitudinal Assessment of Synovial, Lymph Node, and Bone Volumes in Inflammatory Arthritis in Mice using In Vivo MRI and Micro-CT," *Arthritis Rheum* 56(12): 4024-37 (2007), which is hereby incorporated by reference in its entirety). Briefly, mice were positioned with the right leg in a custom-designed murine knee coil and scanned in a Siemens 3 Tesla clinical magnet (Siemens AG, Munich, Germany). A high-resolution fat-suppressed T1-weighted sequence (Sagittal T1-weighted FLASH [fast low-angle shot], repetition time=45 ms, echo time=9.03 ms, 192×192 pixels, 20 mm×20 mm field of view, 32 slices of 0.16-mm slice thickness, flip angle=25°, 1 signal average, time: 8:28) was then initiated. An intravenous injection of Gd-DTPA contrast agent (Omniscan; Amersham Health, now part of GE Healthcare, Little Chalfont, Buckinghamshire, UK) was given, and a post-contrast high-resolution scan (same parameters) was collected. Analysis was performed with Amira 3.1 (TGS; Mercury Computer Systems, Inc., Chelmsford, Mass., USA). An image registration and subtraction algorithm on the pre- and post-contrast images in Amira generated an image of the voxels of contrast enhancement. From this image, a three-dimensional (3D) region of interest of muscle tissue was used as a measure of delivered contrast agent, and a threshold of enhancing synovial tissue was generated from this value. Lymph nodes were traced manually and thresholded to define the margin between the node and surrounding fat. Tissue volumes (3D) were reconstructed using a surface generation module in Amira.

Statistics. Data are presented as mean±standard deviation of three culture dishes, and all experiments were performed at least twice. Statistical analyses were performed with Statview statistical software (SAS Institute Inc., Cary, N.C., USA). Differences among more than two groups were compared using one-way analysis of variance followed by the Mann-Whitney U-test. P-values of less than 0.05 were considered statistically significant. Each experiment was repeated at least twice with similar results.

Example 1

VEGF-C Expression is Upregulated in CD11b$^+$/Gr-1$^{-/lo}$ Osteoclast Precursors from Tumor Necrosis Factor-Transgenic Mice Previous studies demonstrated an increase in circulating OCPs in patients (Ritchlin et al., "Mechanisms of TNF-Alpha- and RANKL-Mediated Osteoclastogenesis and Bone Resorption in Psoriatic Arthritis," *J Clin Invest* 111:821-831 (2003), which is hereby incorporated by reference in its entirety) and animals (Li et al., "Systemic Tumor Necrosis Factor Alpha Mediates an Increase in Peripheral CD11b-high Osteoclast Precursors in Tumor Necrosis Factor Alpha-Transgenic Mice," *Arthritis Rheum* 50:265-276 (2004), which is hereby incorporated by reference in its entirety) with arthritis, and that OCP frequency is reduced in response to anti-TNF therapy, suggesting that OCPs may play important roles in the pathogenesis of arthritis (Xing et al., "Circulating Osteoclast Precursors: A Mechanism and a Marker of Erosive Arthritis," *Curr Rheumatol Rev* 1:21-28 (2005), which is hereby incorporated by reference in its entirety). To screen for novel genes that are differentially expressed by OCPs between arthritic and normal mice, microarray analysis was performed on RNA isolated from CD11b$^+$/Gr-1$^{-/lo}$ OCPs from peripheral blood mononuclear cells and bone marrow pooled from TNF-Tg and WT mice. The purity of CD11b$^+$/Gr-1$^{-/lo}$ cells was confirmed by FACS. In the initial bioinformatic screen, the focus was on genes encoding angiogenic factors because they are critical for development of inflammation and bone erosion in arthritic joints. Among more than 50 known angiogenic factors (including matrix metalloproteinases, adhesion molecules, enzymes, and growth factors), expression levels of PDGF-B, PDGF receptor β, and VEGF-C were found significantly increased in circulating OCPs of TNF-Tg mice (approximately six-fold in TNF-Tg over WT OCPs) (FIG. 1A). Expression levels of these genes were also increased in bone marrow OCPs but to a lesser extent (FIG. 1B). Since TNF is known to induce PDGF signaling (Battegay et al., "TNF-Alpha Stimulation of Fibroblast Proliferation. Dependence on Platelet-Derived Growth Factor (PDGF) Secretion and Alteration of PDGF Receptor Expression," *J Immunol* 154:6040-6047 (1995), which is hereby incorporated by reference in its entirety), the possibility that VEGF-C has a novel role in inflammatory arthritis similar to its role in metastatic cancer was explored (Su et al., "The VEGF-C/Flt-4 Axis Promotes Invasion and Metastasis of Cancer Cells. *Cancer Cell* 9:209-223 (2006); Roy et al., "Biology of Vascular Endothelial Growth Factors," *FEBS Lett* 580:2879-2887 (2006), which are hereby incorporated by reference in their entirety).

Example 2

Tumor Necrosis Factor Stimulates Osteoclast Precursors to Produce VEGF-C

To determine whether TNF directly upregulates expression of VEGF-C by OCPs, WT spleen cells were cultured with M-CSF for 3 days to generate OCPs, as described above. The rationale for using spleen cells rather than bone marrow cells is that spleen-derived OCPs are closer to circulating OCPs than bone marrow OCPs in terms of their osteoclast-forming potency (Yao et al., "Osteoclast Precursors Induce their Differentiation to Osteoclasts by Interacting with Bone Matrix and Secreting Cytokines," *JBMR* 21(Suppl. 2):S262 (2006), which is hereby incorporated by reference in its entirety) and the increased VEGF-C expression level in circulating OCPs is more than three times higher than in bone marrow OCPs (FIGS. 1A-B). TNF treatment increased VEGF-C mRNA levels by three- to four-fold in a time-dependent manner, beginning at between 4 and 8 hours, suggesting transcriptional regulation (FIG. 2A). It also increased VEGF-C protein expression at 24 hours (FIG. 2B). TNF did not significantly affect expression of other VEGF members (FIG. 2C). Dose-response experiments demonstrated that a low dose of TNF (0.5 ng/mL) is sufficient to stimulate VEGF-C protein expression supporting an in vivo role for TNF to induce VEGF-C expression (FIG. 2D).

Whether IL-1, another cytokine whose expression levels are increased significantly in joints of TNF-Tg mice, affects VEGF-C levels in OCPs was also examined. Similar to TNF, IL-1 treatment (by 24 hours) also increased VEGF-C mRNA by two- to three-fold, but IL-1 plus TNF did not have an additive effect (FIG. 2E). This indicates that TNF and IL-1 may use a similar signaling pathway to regulate VEGF-C expression.

Example 3

Nuclear Factor-Kappa B Mediates Tumor Necrosis Factor-Induced VEGF-C Expression

Figure 3C:
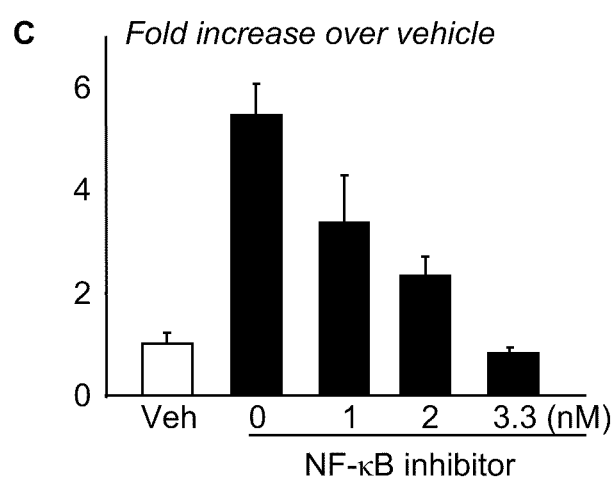

NF-κB is a transcription factor that mediates induction of genes by TNF in many cell types, including OCPs (Zhang et al., "Tumor Necrosis Factor-Alpha (TNF) Stimulates RANKL-Induced Osteoclastogenesis via Coupling of TNF Type 1 Receptor and RANK Signaling Pathways," *J Biol Chem* 276:563-568 (2001), which is hereby incorporated by reference in its entirety). NF-κB also mediates heregulin-beta-1-induced VEGF-C expression in human breast cancer cells (Tsai et al., "Up-Regulation of Vascular Endothelial Growth Factor-C in Breast Cancer Cells by Heregulin-Beta 1. A Critical Role of p38/Nuclear Factor-Kappa B Signaling Pathway," *J Biol Chem* 278:5750-5759 (2003), which is hereby incorporated by reference in its entirety). There is a putative NF-κB-binding element, GGGGTCCC (nucleotides 8-18 of SEQ ID NO:17, FIG. 3B), at the −108/−99 region of the mouse VEGF-C promoter, which is at a location similar to that in the human promoter (Chilov et al., "Genomic Organization of Human and Mouse Genes for Vascular Endothelial Growth Factor-C," *J Biol Chem* 272:25176-25183 (1997), which is hereby incorporated by reference in its entirety). Thus, to determine whether TNF stimulates binding of NF-κB proteins to this element in OCPs, Raw 264.7 cells were treated with TNF for 30 and 60 minutes and Western blot analysis and EMSA were performed on nuclear extracts from the cells. TNF treatment for 30 minutes increased nuclear translocation of NF-κB p65 and p50 proteins (FIG. 3A) and specific binding of NF-κB to the VEGF-C DNA probe (FIG. 3B). To further confirm the involvement of NF-κB in TNF-induced VEGF-C expression, WT OCPs were treated with an NF-κB inhibitor (Calbiochem, now part of EMD Biosciences, Inc., San Diego, Calif., USA) which inhibited TNF-induced VEGF-C expression in a dose-dependent manner (FIG. 3C). These data support TNF induction of VEGF-C expression by activation of NF-κB.

Example 4

CD11b$^+$/Gr-1$^{-/lo}$ Cells Isolated from Joints of Tumor Necrosis Factor-Transgenic Mice Express High Levels of VEGF-C To examine whether OCPs at the site of inflammation express VEGF-C, cells from joints of TNF-Tg mice and WT littermates were isolated using a sequential enzyme digestion method (Brühl et al., "Dual Role of CCR2 During Initiation and Progression of Collagen-Induced Arthritis: Evidence for Regulatory Activity of CCR2$^+$ T Cells," *J Immunol* 172:890-898 (2004); Kamata et al., "Involvement of TNF-like Weak Inducer of Apoptosis in the Pathogenesis of Collagen-Induced Arthritis," *J Immunol* 177:6433-6439 (2006), which are hereby incorporated by reference in their entirety). On average, a total of $1.5 \times 10^6$ cells from the four paws of a TNF-Tg mouse were obtained. FACS analysis revealed that approximately 60% of joint cells from TNF-Tg mice are CD11b$^+$ and almost all of them are Gr-1$^-$ (FIG. 4A). Thus, in subsequent experiments, only CD11b was used as a marker for OCPs. To determine whether CD11b$^+$ cells express VEGF-C, double immunofluorescence staining was performed using anti-CD11b and VEGF-C antibodies in a cytospin preparation of these cells. There was a much greater number of CD11b and VEGF-C double-stained cells in the joints of TNF-Tg mice than in WT mice (compare FIGS. 4E and I). Most of the VEGF-C$^+$ cells are CD11b$^+$, whereas no CD11b$^-$ cells are VEGF-C$^-$, indicating that VEGF-C is produced in arthritic joints by OCPs. To examine whether these joint CD11b$^+$ cells specifically produce more VEGF-C than other VEGFs, they were cultured with M-CSF for 3 days, adherent cells were harvested, and RT-PCR was performed to assess the expression level of VEGF-A, VEGF-C, and VEGF-D. The rationale for using these M-CSF-dependent adherent cells is that they are composed mainly of OCPs and monocytes, as described previously (Zhang et al., "Tumor Necrosis Factor Prevents Alendronate-Induced Osteoclast Apoptosis in vivo by Stimulating Bcl-xL Expression Through Ets-2," *Arthritis Rheum* 52:2708-2718 (2005), which is hereby incorporated by reference in its entirety). M-CSF-dependent cells that were derived from joints of TNF-Tg mice expressed much higher levels of VEGF-C compared with those of WT mice (FIG. 4J), whereas VEGF-A and VEGF-D levels were similar, indicating that OCPs/monocytes are the major source of VEGF-C in arthritic joints of TNF-Tg mice. To confirm that there is elevated TNF or IL-1 expression in the joints of TNF-Tg mice, the expression levels of TNF and IL-1 mRNA were measured. TNF and IL-1 levels were remarkably increased compared to the levels in WT joints (FIG. 4K), which supports the hypothesis that local increased cytokines stimulate VEGF-C production.

Example 5

Increased Lymphangiogenesis in Joints of Tumor Necrosis Factor-Transgenic Mice Since VEGF-C is a specific lymphatic growth factor (Tammela et al., "The Biology of Vascular Endothelial Growth Factors," *Cardiovasc Res* 65:550-563 (2005), which is hereby incorporated by reference in its entirety) and VEGF-C expression is increased in OCPs, whether there was increased lymphangiogenesis in joints of TNF-Tg mice compared to WT mice was determined immunohistochemically using the LYVE-1 antibody which is a lymphatic endothelial cell marker. Because of the increase in blood vessels in TNF-Tg versus WT joints, CD31 staining of endothelial cells was used as a positive control (Yin et al., "Endostatin Gene Transfer Inhibits Joint Angiogenesis and Pannus Formation in Inflammatory Arthritis," *Mol Ther* 5(5 Pt 1):547-554 (2002), which is hereby incorporated by reference in its entirety). The results demonstrate the presence of large LYVE-1$^+$ lymphatic vessels in the pannus of TNF-Tg mice compared to WT (compare FIGS. 5A and C). Histomorphometric quantitation of the area and number of these lymphatic vessels confirmed a significant increase in TNF-Tg versus WT joints (FIGS. 5E-F). To assess the functional significance of this increased lymphangiogenesis, in vivo MRI technology was used to determine whether the draining popliteal lymph nodes from the knee and ankle joints of TNF-Tg mice with synovitis are increased versus WT littermates. FIGS. 6A-D demonstrate the remarkable differences in 2D MRI (FIGS. 6A, C) and 3D reconstructed images (FIGS. 6B, D) of the synovium and popliteal lymph nodes of TNF-Tg versus WT mice. Volumetric analyses confirmed that TNF-Tg mice have significantly larger synovial and popliteal lymph node volumes compared with WT mice (FIGS. 6E-F) and these were confirmed by histology (FIG. 6G).

To demonstrate that increased lymphangiogenesis is not limited to arthritis in TNF-Tg mice and to determine the association between joint inflammation and lymphatic vessel formation during the course of arthritis induction, mice with K/BxN serum-induced arthritis (SIA) were used. This SIA model has clearly distinguishable phases of disease progression and uniform severity of joint lesions among animals compared with TNF-Tg mice. The SIA mice were sacrificed at 0, 14, and 35 days after serum injection, and joint samples were subjected to histology and LYVE-1 immunostaining. FIGS. 7A and B show H&E and LYVE-1 staining, respectively, in joint tissue sections at day 35 after serum injection. At day 14 after serum injection, mice developed severe joint inflammation with pannus formation and inflammatory cell infiltration, which is accompanied with increased lymphatic vessel area and number (FIGS. 7C-E). By day 35, the inflammation declined (FIG. 7E), but the lymphatic vessel formation had increased further (FIG. 7C-D) to a degree similar to that seen in TNF-Tg mice (FIG. 5). These data suggest that increased lymphangiogenesis is a common phenotype of inflammatory-erosive arthritis.

Discussion of Examples 1-5

Patients with rheumatoid arthritis (RA) often have enlarged draining lymph nodes (Olszewski et al., "Lymph Draining from Foot Joints in Rheumatoid Arthritis Provides Insight into Local Cytokine and Chemokine Production and Transport to Lymph Nodes," *Arthritis Rheum* 44:541-549 (2001), which is hereby incorporated by reference in its entirety) and increased lymph flow rates (Huh et al., "The Role of Popliteal Lymph Nodes in Differentiating Rheumatoid Arthritis from Osteoarthritis by Using CE 3D FSPGR MR Imaging: Relationship of the Inflamed Synovial Volume," *Korean J Radiol* 6:117-124 (2005), which is hereby incorporated by reference in its entirety) in affected limbs, which are correlated with inflamed synovial volume. However, a cellular and molecular mechanism to explain these changes has yet to be postulated. As demonstrated in the examples above, CD11b$^+$/Gr-1$^{-/lo}$ OCPs from joints of TNF-Tg mice produce high levels of the lymphatic growth factor, VEGF-C, and joints from mice in two models of RA have increased numbers of lymphatic vessels and enlargement of draining popliteal lymph nodes. Thus, lymphangiogenesis is significantly increased in joints of mice with inflammatory arthritis. To date, most studies of inflammation-induced lymphangiogenesis studies have been performed in tissues like the cornea, lung, and skin (Maruyama et al., "Inflammation-Induced Lymphangiogenesis in the Cornea Arises from CD11b-Positive Macrophages," *J Clin Invest* 115:2363-2372 (2005); Baluk et al., "Pathogenesis of Persistent Lymphatic Vessel Hyperplasia in Chronic Airway Inflammation," *J Clin Invest* 115:247-257 (2005); Wauke et al., "Expression and Localization of Vascular Endothelial Growth Factor-C in Rheumatoid Arthritis Synovial Tissue," *J Rheumatol* 29:34-38 (2002), which are hereby incorporated by reference in their entirety), because frozen sections from these tissues can readily be prepared for immunostaining to identify lymphatic vessels and because dye injection can be used to examine the lymphatic drainage. It is difficult to apply these methods to joints. A combination of microarrays, FACS, immunohistochemistry, and a novel in vivo contrast-enhanced-MRI technique was utilized to demonstrate that the lymphatic vasculature in inflamed joints and draining lymph nodes are significantly increased in TNF-Tg mice or mice with SIA. These findings are consistent with those in clinical studies demonstrating increased VEGF-C expression in RA joints (Wauke et al., "Expression and Localization of Vascular Endothelial Growth Factor-C in Rheumatoid Arthritis Synovial Tissue," *J Rheumatol* 29:34-38 (2002); Cha et al., "Tumor Necrosis Factor-Alpha Induces Vascular Endothelial Growth Factor-C Expression in Rheumatoid Synoviocytes," *J Rheumatol* 34:16-19 (2007), which are hereby incorporated by reference in their entirety) and increased lymph nodel size (Huh et al., "The Role of Popliteal Lymph Nodes in Differentiating Rheumatoid Arthritis from Osteoarthritis by Using CE 3D FSPGR MR Imaging: Relationship of the Inflamed Synovial Volume," *Korean J Radiol* 6:117-124 (2005), which is hereby incorporated by reference in its entirety). Furthermore, based on increased volume of collected lymph (Olszewski et al., "Lymph Draining from Foot Joints in Rheumatoid Arthritis Provides Insight into Local Cytokine and Chemokine Production and Transport to Lymph Nodes," *Arthritis Rheum* 44:541-549 (2001), which is hereby incorporated by reference in its entirety) and the demonstration of increased VEGF-C production by joint OCPs, it is feasible that the development of large lymphatic vessels in the pannus results from proliferation of lymphatic endothelial cells and their distention by increased amounts of lymph.

While the origin of lymphatic endothelial cells remains an area of active research, several studies on inflamed corneas, skin, and lung have reported the presence of CD11b$^+$ myeloid cells expressing VEGF-C in these tissues (Maruyama et al., "Inflammation-Induced Lymphangiogenesis in the Cornea Arises from CD11b-Positive Macrophages," *J Clin Invest* 115:2363-2372 (2005); Kerjaschki D., "Lymphatic Neoangiogenesis in Renal Transplants: A Driving Force of Chronic Rejection?" *J Nephrol* 19:403-406 (2006), which are hereby incorporated by reference in their entirety). These studies speculate that inflammatory cytokines stimulate VEGF-C production by these CD11b$^+$ cells. Here, it has been demonstrated that TNF and IL-1 upregulate VEGF-C expression in CD11b$^+$ OCPs. Preliminary evidence indicates that this response is mediated by NF-κB-dependent transcription. Since other signal transduction pathways could also be involved and TNF could be acting indirectly through prostaglandins (Tammali et al., "Aldose Reductase Regulates TNF-Alpha-Induced PGE$_2$ Production in Human Colon Cancer Cells," *Cancer Lett* 252:299-306 (2007), which is hereby incorporated by reference in its entirety), which also mediate VEGF-C transcription in cancer cells (Timoshenko et al., "COX-2-Mediated Stimulation of the Lymphangiogenic Factor VEGF-C in Human Breast Cancer," *Br J Cancer* 94:1154-1163 (2006), which is hereby incorporated by reference in its entirety), future studies are needed to elucidate the mechanisms of inflammation-induced VEGF-C expression in OCPs.

Considering the cellular heterogeneity of joint pannus, it is important to determine the primary source of VEGF-C in arthritic joints. While these studies focused on OCPs, others have shown that TNF and/or IL-1 stimulates VEGF-C expression by human lung fibroblasts, blood vascular endothelial cells, and synovial cells (Ristimäki et al., "Proinflammatory Cytokines Regulate Expression of the Lymphatic Endothelial Mitogen Vascular Endothelial Growth Factor-C," *J Biol Chem* 273:8413-8418 (1998); Cha et al., "Tumor Necrosis Factor-Alpha Induces Vascular Endothelial Growth Factor-C Expression in Rheumatoid Synoviocytes," *J Rheumatol* 34:16-19 (2007), which are hereby incorporated by reference in their entirety). TNF also stimulates VEGF-C expression in NIH3T3 and C2C12 fibroblast cell lines, in which case fibroblast-like cells in synovium could perhaps be another source of VEGF-C in arthritic pannus. However, these results were obtained from in vitro treatment of cells with cytokines and may not precisely reflect the in vivo situation, particularly in the joint local microenvironment. The immunocytochemical studies using cells freshly isolated from joints demonstrated that most of the VEGF-C-expressing cells are CD11b$^+$ (FIG. 4E). One potential concern with this approach is that primary joint cells are composed of a mixture of cell types. To address this limitation, these cells were cultured with M-CSF and only adherent cells were used for further study. Under these culture conditions, more than 90% of adherent cells are CD11b$^+$/Gr-1$^{-/lo}$ OCPs. These M-CSF-dependent joint cells express much higher levels of VEGF-C than cells treated in vitro (20- to 30-fold increase in joint cells in FIG. 4J versus 3- to 5-fold increase in TNF-treated cells in FIG. 2A). Thus, although other cell types may also be VEGF-C-producing cells, CD11b$^+$/Gr-1$^{-/lo}$ OCPs likely are one of the major sources of VEGF-C in joint pannus.

The present findings demonstrate that increased lymphangiogenesis is associated with the progression of joint inflammation, which occurs not only in dysregulated TNF-induced arthritis (FIGS. 5A-F) but also in mice with SIA (FIGS. 7A-E). A recent study reported that, in joint sections of collagen-induced arthritis, the number of LYVE-1$^+$ lymphatic vessels is increased (Silverman et al., "The Role of Vascular Cell Adhesion Molecule 1/Very Late Activation Antigen 4 in Endothelial Progenitor Cell Recruitment to Rheumatoid Arthritis Synovium," *Arthritis Rheum* 56:1817-1826 (2007), which is hereby incorporated by reference in its entirety). Thus, elevated lymphangiogenesis likely is a common feature of inflammatory arthritis. Inflammation-induced lymphangiogenesis in joints appears to be a slow process, taking 2 to 3 weeks (FIG. 7). A likely explanation is that OCPs or other VEGF-C-producing cells may need to migrate to the inflamed joints first and then respond to elevated cytokine levels to produce VEGF-C, which then stimulates formation of lymphatic endothelial cells.

Interestingly, increased lymphatic vasculature persists even after serum-induced inflammation has resolved (FIG. 7C-E). This is consistent with the observation of no change in lymphatic vessel area or number in TNF-Tg mice, with a significant reduction in their joint inflammation after anti-TNF therapy treatment (see FIGS. 8A-C). Persistent lymphangiogenesis was also reported in a mouse model of chronic respiratory tract infection in which inflammation has been cured by antibiotics (Baluk et al., "Pathogenesis of Persistent Lymphatic Vessel Hyperplasia in Chronic Airway Inflammation," *J Clin Invest* 115:247-257 (2005), which is hereby incorporated by reference in its entirety). Currently, there is no explanation why these lymphatic vessels do not disappear along with the reduction in inflammation. One speculation is that lymphatic enlargement makes affected tissues more susceptible to later inflammation by facilitating the accumulation of immune cells at the site of injury or infection (Bashyam H., "Vessel-Widening by VEGF," *J Exp Med* 204:1240 (2007), which is hereby incorporated by reference in its entirety). However, it is also possible that an increased lymphatic network will prime tissues to respond to acute inflammation.

Materials and Methods for Examples 6-11

Animals and Anti-TNF Treatment. Experiments were performed with sex matched TNF-transgenic 3647 mice (TNF-Tg) and wildtype (WT) littermate controls. An initial comparison between TNF-Tg (n=10, average age=5.10±0.94 months) and wild type mice (n=6, average age=4.91±0.20 months) was performed. Each mouse received a CE-MRI scan and two mice of each group also received dynamic CE-MRI scans. Four TNF-Tg mice received two further MRI scans at 2 weeks and 4 weeks after the initial scan. After their final MR scan the mice were sacrificed and LNs were harvested for immunohistochemistry.

In the anti-TNF therapy study, mice received either murine monoclonal anti-human TNF IgG1 antibody or an irrelevant murine IgG1 placebo control (Centocor R&D Inc., Radnor, Pa., USA) at a dose of 10 mg/kg/week intraperitoneal (i.p.) as previously described (Shealy et al., "Anti-TNF-Alpha Antibody Allows Healing of Joint Damage in Polyarthritic Transgenic Mice," *Arthritis Res* 4: R7 (2002), which is hereby incorporated by reference in its entirety). The study contained two groups each containing four female TNF-Tg mice and one group of four WT mice. The TNF-Tg mice were scanned every 2 weeks starting at 3 months of age and entered into the study when it was determined that inflammatory arthritis had initiated (knee synovial volumes >3 $mm^3$ as measured by Amira analysis). Average age at initiation of treatment was 3.88±0.79 months. One group received weekly anti-TNF injections, while the second group was given placebo, as above. MRI scans were performed at baseline and every 2 weeks for 8 weeks. Age-matched WT mice were scanned at baseline and 8 weeks. At 8 weeks, mice were sacrificed and ankle joints and popliteal LNs were harvested for histology.

Magnetic Resonance Imaging. For dynamic imaging, mice were positioned and localization scans were performed as described supra. Localization scans were used to ensure that all three tissues of interest (popliteal LN, knee synovium, and muscle) are clearly visualized. Then, three short-duration T1-weighted scans were performed as baseline scans (Sagittal T1-weighted FLASH, TR=96 ms, TE=10 ms, 128×128 pixels, 30 mm×30 mm FOV, 6 slices of 1.1 mm slice thickness, flip angle=25°, 1 signal average, time: 12 sec). Gd-DTPA was injected via the retroortibal venous plexus. Immediately subsequent to this injection (~6 sec), a series of dynamic scans with the same parameters as above were initiated. One hundred measurements of 12-sec duration each were made for 20 min after contrast injection.

MR Data Analysis. Amira 3.1 (TGS, Mercury Computer Systems, Inc., San Diego, Calif., USA) was used for analysis of high resolution CE-MRI data. Detailed methods of this analysis for synovial and LN volume computations have recently been described (Proulx et al. "3D-MRI Quantification of the Progression and Amelioration of Inflammatory Arthritis in Mice," *Arthritis Rheumatism* 54:S621 (2006), which is hereby incorporated by reference in its entirety).

Briefly, the 3D stacks of images for the precontrast and postcontrast scans are loaded into the software. An automatic registration and subtraction procedure is performed resulting in a 3D stack of images of contrast enhancement. For segmentation of the LN, Regions of Interest (ROIs) are manually drawn on postcontrast images and thresholded based on signal intensity ≥1500 arbitrary units (AU) to define the boundary between the LN and the fat pad surrounding the node. These labels are then copied onto the subtracted image stack. Next, a section (>15 $mm^3$) of muscle tissue is labeled on the subtracted image stack. The Tissue Statistics module is used to determine the CE of the muscle as an estimate of the delivered dosage of Gd-DTPA. Tissue Statistics module is used to quantify the volume of the LN and the value of CE of this tissue. Normalized LN contrast enhancement (NLCE) is defined as the LN contrast enhancement divided by muscle contrast enhancement. LN capacity (LNCap) is defined as LN volume multiplied by NLCE. Total time for image analysis is around 20 minutes per mouse for an experienced operator.

Amira 3.1 software (TGS/Mercury Computer Systems, San Diego, Calif.) was used for CE-MRI image analysis. The baseline series of scans and the postcontrast series of scans were loaded side by side. ROI were drawn on one stack of the postcontrast series of scans in the following tissues: synovium, popliteal LN, and gastrocnemius muscle. These ROIs were then propagated throughout the series of scans. Mean values of the signal intensity in each tissue were recorded for each baseline and each 12-sec scan for the first 10 min postcontrast and then every fifth scan for the second 10 min post-contrast. Values for signal intensity for each tissue were normalized by subtracting the average baseline values to determine CE values.

Statistical Analyses. Linear mixed-effects regression models, with mouse as a random effect and time (treated as a continuous covariate) as a fixed effect, were used to assess changes over time based on longitudinal data. All slopes were reported as changes per week. Correlations between measures were estimated using Pearson's correlation coefficient and tested for significance using a two-sided t-test. Two-sided t-tests assuming unequal variances were used to make comparisons with CE-MRI data between groups at the same time point or age. All underlying assumptions of the parametric methods were checked, and no serious violations were detected. P-values less than 0.05 were considered significant and P-values less than 0.01 were considered highly significant.

Example 6

Lymph Node Enhancement Patterns Between TNF-Tg and WT Mice

The use of a custom surface coil to quantify the volume of popliteal LNs and knee synovium in WT and TNF-Tg mice by MRI has been previously described (Proulx et al. "3D-MRI Quantification of the Progression and Amelioration of Inflammatory Arthritis in Mice," *Arthritis Rheumatism* 54:S621 (2006), which is hereby incorporated by reference in its entirety). To use this approach to assess LN function, the pattern of LN enhancement versus histology in TNF-Tg and WT mice was investigated. A remarkable differences in size and signal intensity of LNs after CE was observed in TNF-Tg (FIG. 9D) compared to WT (FIG. 9A). At the histologic level, TNF-Tg mice (FIGS. 9E-F) have remarkable expanded LNs and increased LYVE-1$^+$ lymphatic vessels compared to WT mice (FIGS. 9B-C). Furthermore, immunohistochemistry of corresponding sections demonstrated that regions of high intensity in MR images correlate with LYVE-1⁺ sinuses in LNs, while areas of dense parenchymal tissue in LNs (T cell zone and B cell follicles) do not enhance to the same degree. These sinuses are featured with dilated lumen that contains numerous LYVE-1⁺ macrophage-like cells. Quantifications of LYVE-1⁺ regions in entire LNs confirmed that LNs from the TNF-Tg mice have threefold more LYVE-1⁺ lymphatic vessels (FIG. 9G).

Example 7

Dynamic Contrast Enhancement MR Imaging of TNF-Tg Versus WT Mice

To investigate the behavior of CE in popliteal LNs in further detail, dynamic CE-MRI was performed to assess the uptake of intravenous (i.v.)-injected Gd-DTPA into LN, synovium, and adjacent muscle tissue over time in WT and TNF-Tg mice. Representative data from dynamic CE-MRI are shown for WT (FIG. 10A) and TNF-Tg (FIG. 10B) mice, which allowed three conclusions. First, the degree of CE is much greater in the TNF-Tg versus WT LNs, while the CE of other tissues in TNF-Tg versus WT is similar. Second, muscle signal intensity in both animals stayed at constant levels after reaching maximum enhancement at approximately 2 min throughout the length of the scan. This finding is consistent with previous results demonstrating dose-dependent muscle CE in TNF-Tg and WT mice (Proulx et al. "3D-MRI Quantification of the Progression and Amelioration of Inflammatory Arthritis in Mice," *Arthritis Rheumatism* 54:S621 (2006), which is hereby incorporated by reference in its entirety). Since it can be seen from these plots that levels of muscle signal intensity does not change during the length of a high resolution postcontrast scan (boxed areas in FIGS. 10A-B), the CE of adjacent muscle can be used as a normalization for quantifications of LN CE. Third, Gd-DTPA cannot be used to study the rate of enhancement. This is likely due to its small size (571 Da) and ability to rapidly and freely permeate from both normal and leaky blood vessels into the extracellular space (van Dijke et al., "MR Imaging of the Arthritic Rabbit Knee Joint Using Albumin-(Gd-DTPA)30 with Correlation to Histopathology," *Magn Reson Imaging* 17:237-245 (1999), which is hereby incorporated by reference in its entirety). Therefore, it is not possible to estimate the rate of drainage in lymphatic vessels with this contrast agent by measuring the rate of enhancement of the draining LN. However, differences in clearance of contrast agent from the LN between TNF-Tg and WT mice can be detected from the slope of signal intensity over time after the peak of CE. Using this method, WT mice show a rapidly decreasing level of signal intensity immediately after maximum enhancement is reached (slope=−12.4 AU/min from 2 to 20 min, $R^2$=0.881). Since both muscle and synovium do not show similar declining enhancement patterns, this indicates that efferent lymphatic vessels are removing Gd-DTPA contrast agent in the LN, with little to no Gd-DTPA entering the LNs through afferent vessels. However, in the case of the TNF-Tg mouse, the high level of CE persists in the LN; that is, no trend in signal intensity over time is seen (slope=0.2 AU/min from 2 to 20 min, $R^2$=0.002). This indicates that increased lymphatic drainage from inflamed joints is occurring in the TNF-Tg mice.

Example 8

Quantitative Biomarkers of Lymph Nodes from High Resolution CE-MRI

The findings that skeletal muscle CE is Gd-DTPA dose-dependent (Proulx et al. "3D-MRI Quantification of the Progression and Amelioration of Inflammatory Arthritis in Mice," *Arthritis Rheumatism* 54:S621 (2006), which is hereby incorporated by reference in its entirety), and that this tissue stays enhanced at a constant level during a postcontrast scan (FIGS. 10A-B), allows for the use of this tissue for normalization in quantitative longitudinal studies of adjacent tissue. Thus, this quantitative analysis was performed by dividing the calculated mean CE value for a segmented volume of LN by that of the adjacent muscle, which was termed Normalized LN Contrast Enhancement (NLCE). By combining this measurement with 3D-MRI, highly significant differences were observed in both LN volume (FIG. 11A) and NLCE (FIG. 11B) in TNF-Tg versus WT littermates at 5 months of age. For LN volume, there was an approximate eightfold increase in TNF-Tg mice compared to WT (FIG. 11A; 10.42±4.18 vs. 1.26±0.28, P<0.0001). An 1.8-fold increase in NLCE was seen in TNF-Tg mice compared to WT (FIG. 11B; 3.94±1.01 vs. 2.22±0.30, P<0.001). A highly significant correlation (FIG. 11C, $R^2$=0.73, P<0.0001) was found between LN volume and NLCE. Therefore, it can be concluded that increases in LN volume are closely related to increased uptake of contrast agent. Since contrast agent patterns from MRI correlate with the location of dilated LYVE-1⁺ sinuses (FIG. 9), increases in LN volume in early arthritic TNF-Tg animals are mainly due to increased sinus spaces in LNs rather than cellular proliferation. With this in mind, a quantification termed LN capacity (LNcap) was developed, which is the LN volume multiplied by NLCE. This measure can be thought of as a surrogate marker of lymphatic drainage. FIG. 11D demonstrates the differences in LNcap between WT and TNF-Tg mice. While the mean LNcap for the six WT mice was very low (2.83+/−0.91), the average value for TNF-Tg mice (43.70±25.95) demonstrates a highly significant 15-fold increase (P<0.001). As can been seen in FIG. 11D, there was great variability in LNcap between mice in the TNF-Tg group, where increases over WT ranged from 5-fold to 33-fold.

Example 9

Effect of Anti-TNF Therapy on LN Quantitative Biomarkers

To assess the potential of these quantitative LN biomarkers to track longitudinal changes in LNs and to show response to a proven therapeutic intervention, TNF-Tg mice were subjected to weekly administration of either anti-TNF therapy or placebo for 8 weeks. High-resolution CE-MRI scans were performed at baseline and every 2 weeks. In addition, WT mice were scanned at baseline and 8 weeks as a control. A regression analysis of the slopes was used to determine if the biomarkers showed significant changes versus time.

As shown in FIG. 12A, mice receiving anti-TNF therapy demonstrated a significant decrease in NLCE values (slope=− 0.16, P=0.001). NLCE values after therapy were nearly identical to WT mice (2.30±0.27 versus 2.20±0.39, P=0.70). In contrast, placebo mice showed a significant increase in NLCE values (slope=0.12, P<0.01) during the 8-week study. These results demonstrate a highly significant treatment effect (difference in slopes between anti-TNF and placebo groups=0.28, P<0.0001).

Longitudinal assessment of LNcap values between anti-TNF and placebo groups is seen in FIG. 12B. Mice receiving therapy exhibited highly significant decreases in LNcap (slope=−3.58, P<0.0001). LNcap values in the anti-TNF group approached, but never reached WT levels. After 8 weeks, LNcap values of anti-TNF mice were 6.40±1.53. Age-matched WT mice had values of 2.93±1.06. This represents a significant difference between anti-TNF mice and WT (P<0.05). As there was no difference in NLCE enhancement at this time, these differences are due to the highly significant difference in volumes that persists after therapy (anti-TNF: 2.77±0.48 mm$^3$, WT: 1.31+/−0.29 mm$^3$, P<0.01). Mice receiving placebo demonstrated a significant increase in LNcap values during the 8 weeks (slope=2.85, P=0.001). There was a highly significant treatment effect of anti-TNF shown with LNcap values (difference in slopes=6.43, P<0.0001). A representative example visualizing the decrease in LNcap values that occurs with anti-TNF is shown in FIG. 12C at baseline and FIG. 12D at 8 weeks.

Example 10

Persistence of LYVE-1 Positive Lymphatic Vessels after Anti-TNF Therapy in LNs and Joints The finding that anti-TNF treatment of TNF-Tg mice reduces the NLCE to WT levels without normalizing LN volume and LNcap, begged the investigation of anti-TNF effects on lymphatic vessels in LN and synovium. Immunohistochemical analysis found that in contrast to WT LN that have small numbers LYVE-1$^+$ vessels (FIG. 9C), anti-TNF-treated TNF-Tg mice still have large numbers of LYVE$^+$ vessels throughout their LN (FIG. 12E), at similar levels to that observed before therapy (FIG. 9F). Moreover, the number of LYVE$^+$ vessels in the inflamed synovium of TNF-Tg mice treated with anti-TNF or placebo were not markedly different (FIG. 12F-G). However, the vessel diameter in both tissues of anti-TNF-treated mice was markedly smaller than placebo (FIGS. 12F-G). These narrower lymphatic vessels may reflect a reduction in the lymphatic transfer from joints to local draining LNs after anti-TNF treatment due to decreased inflammation. These results are consistent with findings in other inflammation models (Baluk et al., "Pathogenesis of Persistent Lymphatic Vessel Hyperplasia in Chronic Airway Inflammation," *J Clin. Invest* 115:247-257 (2005), which is hereby incorporated by reference in its entirety), and demonstrate that lymphatic vessels persist long after an inflammatory insult is removed.

Example 11

Accelerated Progression to Severe Arthritis in TNF-Tg Mice with Low LNcap

As seen in FIG. 11D, there is tremendous variability in LNcap values in TNF-Tg mice at similar ages. As high variability in knee synovial volumes is also a feature of this model (Proulx et al. "3D-MRI Quantification of the Progression and Amelioration of Inflammatory Arthritis in Mice," *Arthritis Rheumatism* 54:S621 (2006), which is hereby incorporated by reference in its entirety), it was determined whether there was a relationship between these two MRI measures with the hypothesis that increased LNcap values would prevent swelling in the joints. In support of this, a significant negative correlation was found (FIG. 13A; $R^2$=0.63, P=0.010) between LNcap and synovial volume in TNF-Tg mice. Further illustrative of this inverse relationship are CE-MR images of a representative TNF-Tg mouse with a high LNcap (FIG. 13B-D), which show that larger LNs with greater CE are associated with smaller synovial volumes. In contrast, smaller LNs with lower CE are associated with synovitis (FIG. 13E-G). Setting a threshold for low LNcap at <35, and for high LNcap at >50, two mice in each group were followed for 4 weeks with further CE-MRI (FIG. 14A). The two mice with low LNcap showed dramatic increases in synovial volume from 0 weeks to 4 weeks (+90% and +163%). By comparison, the two mice with high LNcap were protected from increases in synovial volume (+12% and −24%). To better demonstrate the rapid progression of knee arthritis in TNF-Tg mice with a low LNcap phenotype over time, a longitudinal series of CE-MRI scans from a representative mouse is shown (FIG. 14B-G). The mild inflammation at 2.5 months (FIG. 14B), markedly increases over the next 1.5 months as demonstrated by severe edema (FIG. 14C-E). However, as a result of uncontrolled inflammation and joint destruction over time, necrotic tissue changes occur, as evidenced by the regions of low CE, leading to a decreased measurement of synovial volumes with CE-MRI (FIG. 14F-G).

Discussion of Examples 6-11

Assessments of draining LNs are emerging as important biomarkers of inflammatory diseases. However, even though LNs can be readily imaged in humans, their longitudinal assessment in animal models has been prohibitive. As a result, an understanding of the clinical information and its prognostic value has been limited. Here CE-MRI of TNF-Tg mice was used to demonstrate the potential of draining LN function to predict the outcome of inflammatory arthritis. These studies show that inflammatory arthritis initially leads to lymphangiogenesis in the synovium and draining LN (FIG. 9), which significantly increases LNcap (FIG. 11).

One enigma of RA and animal models of inflammatory arthritis is the well-known variability in synovitis that occurs between individuals, as well as interjoint variability within the same individual. By quantifying LNcap longitudinally in TNF-Tg mice, it was found that synovitis in an arthritic joint inversely correlates with draining LN function (FIG. 13A), and may be predictive of the progression of inflammatory-erosive arthritis (FIG. 14). One interpretation of these results is that lymphangiogenesis, in response to the initiation of arthritis, is responsible for increasing the exudation of inflammatory cells and factors out of the inflamed synovium before they can cause joint destruction. If inflammation subsides or is sustained at a level within the capacity of the draining LN, the joint will be protected from synovitis, tissue necrosis, and focal bone loss. However, if LNcap is exceeded, or breaks down over time, a critical mass of inflammatory mediators and catabolic factors in the joint cannot be held in check. This theory is supported by studies that showed the importance of VEGF-C-mediated lymphangiogenesis for control of UVB-induced skin edema (Kajiya et al., "An Important Role of Lymphatic Vessels in the Control of UVB-Induced Edema Formation and Inflammation," *J Invest Dermatol* 126:919-921 (2006), which is hereby incorporated by reference in its entirety), and chronic airway inflammation (Baluk et al., "Pathogenesis of Persistent Lymphatic Vessel Hyperplasia in Chronic Airway Inflammation," *J Clin. Invest* 115:247-257 (2005), which is hereby incorporated by reference in its entirety). Additionally, the lymphoid neogenesis that is a hallmark of end-stage autoimmune diseases, including RA, has been proposed to be caused by insufficient lymph outflow (Thaunat et al., "Is Defective Lymphatic Drainage a Trigger for Lymphoid Neogenesis?" *Trends Immunol* 27:441-445 (2006), which is hereby incorporated by reference in its entirety). Thus, the stage is set for future studies aimed at elucidating the cause and effect of draining LN impairment on arthritis progression.

Another important finding in this study is the persistence of lymphatic vessels in the synovium and draining LN after effective anti-TNF therapy (FIG. 12). In contrast to blood vessels that rapidly degenerate following removal of inflammatory signals, lymphatic vessels remain long after the pathogenic stimuli is cleared (Baluk et al., "Pathogenesis of Persistent Lymphatic Vessel Hyperplasia in Chronic Airway Inflammation," *J Clin. Invest* 115:247-257 (2005), which is hereby incorporated by reference in its entirety). The implied significance of this may be that the joint is now primed to respond to acute inflammation or flare, and that effective therapy may not need to be immunosuppressive to the point of complete inhibition of inflammatory responses. Rather, a new target could be enhancing LNcap, potentially via local delivery of VEGF-C (Yoon et al., "VEGF-C Gene Therapy Augments Postnatal Lymphangiogenesis and Ameliorates Secondary Lymphedema," *J Clin Invest* 111:717-725 (2003), which is hereby incorporated by reference in its entirety).

While this pioneering study into the use of CE-MRI to assess LN function has identified several useful outcomes, it also has presented several limitations. First, image saturation due to dense accumulation of Gd-DTPA contrast agent occurred in some mice with higher LNcap. Therefore, NLCE and LNcap measures are actually underestimated in these TNF-Tg mice, but this did not prevent significant results from being found. Further adjustments to MRI sequences and/or lower doses of Gd-DTPA will reveal the true extent of increases of LNcap in TNF-Tg mice. Second, no direct measures of lymphatic drainage were performed. This is not possible in dynamic CE-MRI with Gd-DTPA due to its small size (van Dijke et al., "MR Imaging of the Arthritic Rabbit Knee Joint Using Albumin-(Gd-DTPA)30 with Correlation to Histopathology," *Magn Reson Imaging* 17:237-245 (1999), which is hereby incorporated by reference in its entirety). An MRI contrast agent macromolecule that stays confined in the lymphatic vasculature is necessary for these studies (Herborn et al., "Interstitial MR Lymphography with MS-325: Characterization of Normal and Tumor-Invaded Lymph Nodes in a Rabbit Model," *AJR Am J Roentgenol* 179:1567-1572 (2002); Kobayashi et al., "Lymphatic Drainage Imaging of Breast Cancer in Mice by Micro-Magnetic Resonance Lymphangiography Using a Nano-Size Paramagnetic Contrast Agent," *J Natl Cancer Inst* 96:703-708 (2004), which are hereby incorporated by reference in their entirety). However, the LNcap measure is an accurate estimation of the drainage potential of a lymph node. This approach also has the advantages of being performed using the same scans that assess synovial inflammation, with a shorter time to maximum enhancement, and allows the use of enhancing muscle as a normalization for quantification. Third, concurrent measurements of ankle inflammation were not made. As the popliteal lymph node drains both the knee and the ankle joints (Tilney N. L., "Patterns of Lymphatic Drainage in the Adult Laboratory Rat," *J Anat* 109:369-383 (1971), which is hereby incorporated by reference in its entirety), it is certain that ankle inflammation, which occurs earlier in the disease process in mice, has an important role in LN expansion. Ankle inflammation, however, has less variability in this model, so it is likely that the effects of low LNcap on ankle inflammation are not as dramatic as they are at the knee.

In summary, draining LN is a dynamic and functionally significant biomarker of joint inflammation. Future studies designed to determine its diagnostic potential and whether or not lymphangiogenesis is targetable in patients with RA are warranted.

Material and Methods for Examples 12-14

Animal experiments. TNF-Tg mice (2.5-months-old) were treated with anti-mouse VEGFR-2 (DC101) or anti-mouse VEGFR-3 (mF4-31C1) neutralizing antibody (ImClone, New York, N.Y.) at the dose of 0.8 mg/mouse, twice a week by intra-peritoneal injection for 8 weeks or with rat IgG (Innovative, Southield, Mich.) as a control. DC101 blocks the binding of VEGF-A to the VEGFR-2 and inhibits tumor growth in mice through an anti-angiogenic mechanism (Witte et al., "Monoclonal Antibodies Targeting the VEGF Receptor-2 (Flk1/KDR) as an Anti-Angiogenic Therapeutic Strategy," *Cancer Metastasis Rev* 17(2): 155-61 (1998), which is hereby incorporated by reference in its entirety). mF4-31C1 is a rat monoclonal antibody which specifically antagonizes the binding of VEGF-C to VEGFR-3 and completely blocks both VEGF-C-enhanced physiological and tumor-induced lymphangiogenesis in an adult murine tail skin lymphatic generation model (Pytowski et al., "Complete and Specific Inhibition of Adult Lymphatic Regeneration by a Novel VEGFR-3 Neutralizing Antibody," *J Natl Cancer Inst* 97(1): 14-21 (2005), which is hereby incorporated by reference in its entirety).

FITC-Dextran Footpad Injection and PLN Confocal Microscopy. TNF-Tg mice (4-6-months-old) and WT littermates were anesthetized, and 10 µl (10 mg/ml) of FITC-Dextran (molecular weight, 2,000K, Sigma) were injected to the footpad intra-dermally with a 30 G needle linked to a 0.5 ml syringe. The size of Dextran used is too large to enter the blood stream and is routinely used in lymphatic studies (Leu et al., "Absence of Functional Lymphatics Within a Murine Sarcoma: A Molecular and Functional Evaluation," *Cancer Res* 60(16):4324-7 (2000); Leu et al., "Flow Velocity in the Superficial Lymphatic Network of the Mouse Tail," *Am J Physiol* 267(4 Pt 2):H1507-13 (1994), which are hereby incorporated by reference in their entirety). The animals were sacrificed 1 hour later and popliteal lymph nodes (PLNs) were placed on a glass slide. Entire PLNs were scanned under a Leica TCS SP Spectral Confocal microscope (Leica Microsystems Inc., Bannockburn, Ill.). A total of 100 slices about 600~800 µm deep were taken for each node, and a total of 4 nodes from TNF-Tg mice or WT littermates was examined.

In vivo CE-MRI The CE-MRI was performed before and after the antibody treatment. Mice were positioned with a hind leg in a newly developed custom-designed murine dual RF receiver coil (one coil encompassing the ankle joint and another for the knee joint and PLN). MRI and data analysis were performed as described in Examples 1-5 above.

Indocyanine Green Near Infrared (ICG-NIR) Lymphatic Imaging. To examine the status of lymphatic draining function in legs of TNF-Tg mice, a protocol using ICG-NIR imaging technology was established according to published literature (Sevick-Muraca et al., "Imaging of Lymph Flow in Breast Cancer Patients After Microdose Administration of a Near-Infrared Fluorophore: Feasibility Study," *Radiology* 246(3):734-41 (2008); Kwon et al., "Noninvasive Quantitative Imaging of Lymph Function in Mice," *Lymphat Res Biol* 5(4):219-31 (2007), which are hereby incorporated by reference in their entirety) and past experience with large animals and human subjects. In brief, on the first day, ICG solution was injected into the footpads intra-dermally and 5 minutes later the dynamics of ICG contrast agent fluorescence over the entire leg region, including PLNs and paws, was visualized under an infrared laser and recorded. A series of still images was collected from a video camera for 1-2 hours until the maximum ICG signal intensity was reached in the PLNs. The NIR imaging is repeated for 10 minutes 24 hours post ICG injection (See FIG. 15 for a representative image). These images were read into the Image J software. The regions of interest defining the PLNs, draining lymphatic channels, and injection site were identified, yielding four outcome measures of lymphatic function: 1) T-initial (Ti), which is the time that it takes for the ICG to be detected in the draining PLN; 2) S-max, which is the maximum ICG signal intensity (SI) observed in the PLN during the first day imaging session; 3) T-max, which is the time it takes for a PLN to achieve maximal SI; and 4) % Clearance, which is an assessment of ICG contrast agent wash out that is quantified as the percent difference of signal intensity from two NIR scans at S-max and 24 hours after injection from region of interest of the PLNs or footpad.

To observe the ICG distribution within the lymphatic network of PLNs, ICG was injected intra-dermally into footpads, and PLNs were harvested 1 hour later. Frozen sections (10 μm) were observed under a microscope with an infrared filter (ICG filter cube 41030 in-CYGR Chroma Technology Corp.; excitation: 775±50 nm and emission: 845±55 nm). After taking pictures to record the distribution of ICG fluorescence, the same section was stained with rabbit anti-LYVE-1 antibody (Abcam Inc. Cambridge. MA) followed by Alexa Fluor 488 F(ab')$_2$ fragment goat anti-rabbit IgG (H+L).

Immunostaining and Histomorphometric Analysis. PLN, ankle, and knee specimens were fixed in 4.5% phosphate-buffered formalin and embedded in paraffin wax. For immuno-fluorescence staining and data analysis, sections were stained with a mixture of PE-anti-CD11b or PE-anti-CD11c and anti-VEGF-C antibody followed by Alexa Fluor 488 F(ab')$_2$ fragment goat anti-rabbit IgG (H+L) and TO-PRO-3 iodide. Three pictures are taken from each section (×40) for different fields using an Olympus AH-2 confocal microscope. The analysis was performed by counting the TO-PRO-3 iodide$^+$ cells as the total cell number in each field, and the numbers of CD11b$^+$ and VEGF-C$^+$ cell were counted in the same field. The data were presented as the percentage of CD11b$^+$ or VEGF-C$^+$ cells over the total cell number. For immunohistochemistry staining, adjacent serial sections were stained with anti-LYVE-1 or anti-CD31 antibodies. Lymphatic vessels were quantified by a point-counting method. The percent of inflammatory area was measured as follows: photographs (×10 objective lens) were taken of H&E-stained joint sections and opened into Adobe Photoshop software. The inflammatory area and total tissue area were selected using the magic wand tool and the pixel number for the selected area was obtained by the graph tool. The percentage of inflammatory area was calculated by dividing the pixel number of inflammatory area by those of the whole tissue area. The data are presented as the mean from 3 levels of each ankle joint.

Quantitative Real Time RT-PCR. The murine primer sequences are shown in Table 2 below. The relative standard curve method was used to quantitate RNA expression levels (Johnson et al., "Quantitation of Dihydropyrimidine Dehydrogenase Expression by Real-Time Reverse Transcription Polymerase Chain Reaction," *Anal Biochem* 278(2):175-84 (2000), which is hereby incorporated by reference in its entirety). Standards and samples were run in triplicate.

TABLE 2

Primers Sequences for Real-Time PCR

| Genes | Sequences of Primers | Product sizes (bp) | SEQ ID NO: |
|---|---|---|---|
| RANKL | F: 5' CCAAGATCTCTAACATGACG 3' | 140 | 20 |
|  | R: 5' CACCATCAGCTGAAGATAGT 3' |  | 21 |
| VEGF-A | F: 5' ATTGAGACCCTGGTGGACATCTTC 3' | 200 | 22 |
|  | R: 5' CTCATCTCTCCTATGTGCTGGCTT 3' |  | 23 |
| VEGF-B | F: 5' CCTGGAAGAACACAGCCAAT 3' | 175 | 24 |
|  | R: 5' GGAGTGGGATGGATGATGTC 3' |  | 25 |
| VEGF-C | F: 5' GGGAAGAAGTTCCACCATCA3' | 135 | 26 |
|  | R: 5' ATGTGGCCTTTTCCAATACG 3' |  | 27 |
| VEGF-D | F: 5' GCTGTCACTGTTGCCCACTA 3' | 189 | 28 |
|  | R: 5' CCCTTCCTTTCTGAGTGCTG 3' |  | 29 |
| TNF | F: 5' CACACTCAGATCATCTTCTCAA 3' | 182 | 30 |
|  | R: 5' AGTAGACAAGGTACAACCCATC 3' |  | 31 |
| CD11b | F: 5' GACTCAGTGAGCCCCATCAT 3' | 170 | 32 |
|  | R: 5' AGATCGTCTTGGCAGATGCT 3' |  | 33 |
| IL-1 | F: 5' ATTAGACAACTGCACTACAGG 3' | 122 | 34 |
|  | R: 5' GGAGAATATCACTTGTTGGTTG 3' |  | 35 |
| β-actin | F: 5' ACCCAGATCATGTTTGAGAC 3' | 224 | 36 |
|  | R: 5' GTCAGGATCTTCATGAGGTAGT 3' |  | 37 |

F: forward primer, R: reverse primer.
Primer target site and gene accession number for each gene is as follows: RANKL-nucleotides 635-774 of Accession No. BC125603; VEGFA-nucleotides 246-445 of Accession No. M95200; VEGFB-nucleotides 537-701 of Accession No. NM_011697; VEGFC-nucleotides 1352-1486 of Accession No. NM_009506; VEGFD-nucleotides 1236-1424 of Accession No. B89628; TNF-nucleotides 390-571 of Accession No. X02611; CD11b-nucleotides 2276-2445 of Accession No. NM_001082960; IL-1-nucleotides 426-547 of Accession No. NM_00836; Beta-Actin-nucleotides 280-503 of Accession No. X03765

Statistics. Data are presented as means±standard deviation, and all experiments were performed at least twice with similar results. Statistical analyses were performed with Statview statistical software (SAS, Cary, N.C.). Differences between two groups were compared using un-paired Student t-test and more than two groups were compared using one-way ANOVA, followed by a Bonferroni/Dunnet test p-values less than 0.05 were considered to be statistically significant.

Example 12

Increased Lymphatic Drainage in Draining Lymph Nodes of TNF-Tg Mice

Example 6-11 above show 4-6-month-old TNF-Tg mice have increased lymphangiogenesis in their PLNs, as evidenced by numerous dilated LYVE-1$^+$ vessels. These large lymphatic vessels are associated with severe ankle arthritis and variable knee synovitis in all mice at this age. To determine if these dilated LYVE-1+ sinuses in the PLNs are functional and capable of draining afferent lymph, FITC-dextran was intra-dermally injected as a lymphatic tracer into the footpads of 4-6-month-old TNF-Tg mice and wild type (WT) littermate controls. The distribution of FITC fluorescence within the PLNs was observed by scanning confocal microscope. In WT mice, a thin layer of the FITC fluorescence was visualized primarily in marginal sinuses, which receives lymph from the afferent lymphatic vessels (FIG. 16A). The majority of the FITC fluorescence was concentrated at the medullary region, from which lymph exits through efferent lymphatic vessels. In contrast, the FITC signals were broadly distributed throughout the TNF-Tg PLNs (FIG. 16B). TNF-Tg PLNs were markedly expanded and displayed a disorganized T and B cell zones compared to WT (FIGS. 16C-D). The distribution pattern of actively draining lymph was corroborated by ICG-NIR imaging, as intra-dermal injection of ICG, another lymphatic tracer, into the footpad generated the same results as FITC-dextran (FIGS. 16E-F). To confirm that the ICG was within lymphatic vessels, LYVE-1 immunostaining was performed in adjacent sections (FIGS. 16G-H), which demonstrated that ICG was contained within numerous dilated lymphatic sinuses. These findings indicate that chronic inflammation in the lower extremities of TNF-Tg mice leads to significantly increased lymphangiogenesis and functional dilation of lymphatic sinuses in the PLNs, which actively drain fluid from the foot.

Example 13

Blockade of VEGFR-3 Signal Pathway Prevents Increased Lymph Node Enlargement and Lymphangiogenesis but Increases the Severity of Joint Synovitis in TNF-Tg Mice Inflammation-induced lymphangiogenesis in various animal models has been demonstrated to be mediated by TNF and IL-1 induced VEGF-A and/or VEGF-C signaling pathways (Angeli et al., "B cell-Driven Lymphangiogenesis in Inflamed Lymph Nodes Enhances Dendritic Cell Mobilization," *Immunity* 24(2):203-15 (2006); Baluk et al., "Pathogenesis of Persistent Lymphatic Vessel Hyperplasia in Chronic Airway Inflammation," *J Clin Invest* 115(2):247-57 (2005); Ji R C., "Lymphatic Endothelial Cells, Inflammatory Lymphangiogenesis, and Prospective Players," *Curr Med Chem* 14(22):2359-68 (2007), which are hereby incorporated by reference in their entirety). To investigate the involvement of these cytokines in this model, quantitative RT-PCR on mRNA isolated from WT and TNF-Tg PLNs was performed (FIG. 17). Consistent with these other models, TNF, IL-1, VEGF-A and VEGF-C expression levels were significantly increased in TNF-Tg PLNs compared to WT nodes, while VEGF-B and VEGF-D levels were unchanged.

To further elucidate the roles of VEGF-A and VEGF-C signaling in TNF-induced inflammation and lymphangiogenesis during chronic arthritis, VEGFR blockade experiments using neutralizing antibodies were performed. It was hypothesized that blockade of VEGFR-2 would inhibit both inflammation and lymphangiogenesis by preventing the initiation of arthritis as has been show for VEGF-A antagonism (Angeli et al., "B cell-Driven Lymphangiogenesis in Inflamed Lymph Nodes Enhances Dendritic Cell Mobilization," *Immunity* 24(2):203-15 (2006), which is hereby incorporated by reference in its entirety), while interruption of VEGF-C/VEGFR-3 signaling specifically blocks lymphangiogenesis, but not angiogenesis or inflammation (Pytowski et al., "Complete and Specific Inhibition of Adult Lymphatic Regeneration by a Novel VEGFR-3 Neutralizing Antibody," *J Natl Cancer Inst* 97(1): 14-21 (2005), which is hereby incorporated by reference in its entirety). To test this hypothesis 2.5 month-old TNF-Tg mice were treated with anti-VEGFR-2, anti-VEGFR-3, or irrelevant IgG control antibodies for 8 weeks. The treatment effects on PLN volume and perfusion were assessed via CE-MRI obtained before and after therapy.

Compared to the baseline values, the PLN volume in placebo treated mice increased by more than 100% (FIGS. 18A-B, G), while they were unchanged or slightly decreased in VEGFR-2 (FIGS. 18E-F, G) and VEGFR-3 (FIGS. 18C-D, G) antibody-treated mice. Accordingly, the PLNs in anti-VEGFR treated mice weighed significantly less than those of IgG-treated animals (FIG. 18H). LYVE-1 immunostaining and histomorphormetric analysis of the PLN sections revealed that VEGFR-2 & 3 antibody significantly reduced the size, number, and area of LYVE-1+ lymphatic capillaries compared to placebo controls (FIGS. 18I-P).

Having demonstrated the effects of VEGFR blockade on lymphangiogenesis in PLNs, its effects on joint inflammation to establish the direct relationship between lymphatic vessel formation and synovitis was examined. 3D analyses of the CE-MRI data revealed dramatic difference in the change in volume of ankle synovitis between all three treatment groups (FIGS. 19A-B). The synovial volumes of the placebo group demonstrated an insignificant change, the anti-VEGFR-3 group was significantly increased, and the anti-VEGFR-2 group was significantly decreased (FIG. 19A). The mean percent changes also reflected this, with a 45% increase in the anti-VEGFR-3 group and a 35% decrease in the anti-VEGFR-2 group (FIG. 19B). Volumetric assessment of knee synovitis also demonstrated that anti-VEGFR-3 treatment exacerbated inflammatory arthritis, as a significant increase in anti-VEGFR-3 treated group (76.7+/−28.1%) compared to placebo controls (36.5+/−21.0%; p<0.05) was observed. These findings were corroborated by histomorphometry of the inflammatory tissue in the ankle joints of hematoxylin and eosin (H&E) stained histology sections, which also demonstrated a significant increase and decrease in ankle inflammation in the VEGFR-3 vs. VEGFR-2 groups, respectively (FIGS. 19C-D).

As these results support the hypothesis regarding the differential effects of VEGFR-2 vs. VEGFR-3 blockade during chronic arthritis, changes in the vasculature within joints via immunohistochemistry was investigated. Consistent with the PLN data, both VEGFR-2 and VEGFR-3 antibody-treated mice had fewer LYVE-1+ lymphatic vessels compared to placebo treated controls (FIG. 19E). In contrast, only the anti-VEGFR-2 treatment reduced the number of CD31-positive blood vessels (FIG. 19F), indicating that this treatment prevents the initiation of inflammatory arthritis. Collectively, these findings indicate that VEGFR-2 induced lymphangiogenesis is secondary to its direct effects on angiogenesis and recruitment of VEGF-C producing inflammatory cells to the joint, which triggers VEGFR-3 signals to stimulate lymphangiogenesis in the synovium and draining lymph nodes.

Example 14

Exacerbation of Inflammatory Arthritis by VEGFR-3 Blockade is Associated with Decreased Afferent Lymph Flow to Draining Nodes To test the hypothesis that VEGFR-3 signals are responsible for increased lymphatic drainage of inflamed joints during arthritis progression, ICG-NIR imaging on the legs of TNF-Tg mice treated with anti-VEGFR-3 or placebo was performed. FIG. 20 demonstrates the dramatic differences after 8-weeks of therapy. Placebo PLNs displayed a bright fluorescent signal at S-max (FIG. 20A) that was cleared 24 hours later (FIG. 20B), while the S-max signal in anti-VEGFR-3 treated PLNs was scant (FIG. 20C), and fluorescent signal in the foot remained strong the day after ICG injection (FIG. 20D). Quantitative analysis of the ICG-NIR images confirmed the significant increases in T-initial and T-max (FIGS. 20E-F), and significant decreases in S-max and ICG clearance in anti-VEGFR-3 vs. placebo treated mice (FIGS. 20G-H). Thus, these results demonstrate for the first time that VEGFR-3 induced lymphangiogenesis protects joints from accelerated arthritis by increasing the afferent flow of lymph from the inflamed tissues.

Example 15

VEGFR-3 Blockade Decreases VEGF-C Expressing CD11b$^+$ Cells in Draining Lymph Nodes of TNF-Tg Mice Since it is known that CD11b$^+$ macrophages and dendritic cells are the primary infiltrating cells that produce VEGF-C in inflammatory tissues (Baluk et al., "Pathogenesis of Persistent Lymphatic Vessel Hyperplasia in Chronic Airway Inflammation," *J Clin Invest* 115(2):247-57 (2005); Xing et al., "Circulating Osteoclast Precursors: A Mechanism and a Marker of Erosive Arthritis," *Curr Rheumatol Rev* 1:21-28 (2005), which are hereby incorporated by reference in their entirety), this cell population in PLNs of TNF-Tg mice with inflammatory arthritis vs. WT controls was investigated using two color immunofluorescence microscopy. The results demonstrated that the number of CD11b$^+$ and VEGF-C$^+$ cells is significantly increased in TNF-Tg PLNs (FIGS. 21A-B) vs. WT (FIGS. 21D-E), and many of these cells are CD11b/VEGF-C double positive (FIGS. 21C, F). The expression of TNF and IL-1 is increased in TNF-Tg PLNs (FIG. 21H). Interestingly, this CD11b$^+$ population was markedly reduced in PLNs of anti-VEGFR-3 treated TNF-Tg mice as evidenced by significant decrease in immunoreactive cells and cd11b transcript levels (FIGS. 2I and J). These data indicate that increased expression of inflammatory cytokines and presence of myeloid cells in draining lymph nodes may contribute to lymph node lymphangiogenesis in TNF-Tg mice through a VEGF-C/VEGFR-3 mediated event.

Discussion of Examples 12-15

Increased lymphatic vessel formation has been reported in several animal models of inflammation (Ji R C., "Lymphatic Endothelial Cells, Inflammatory Lymphangiogenesis, and Prospective Players," *Curr Med Chem* 14(22):2359-68 (2007), which is hereby incorporated by reference in its entirety). However, it remains unclear if increased lymphangiogenesis only reflects the consequences of inflammation or if it plays an active role in the development and progression of inflammation. In the examples above, using TNF-Tg mice as a model of chronic inflammatory arthritis, it was demonstrated that blockade of VEGF-C/VEGFR-3 signaling by VEGFR-3 neutralizing antibody reduces lymphangiogenesis and lymphatic drainage and increases the severity of joint synovitis. In contrast, VEGF-2 blockade reduces both lymphangiogenesis and synovitis. These findings indicate that lymphangiogenesis and lymphatic drainage actively contribute to the progression of inflammatory reactions in chronic inflammation. Improvement and maintenance of sufficient lymphatic drainage represents a new therapeutic strategy for chronic inflammatory disorders.

Clinical studies in patients with RA have demonstrated high levels of pro-inflammatory cytokines in lymph draining arthritic joints and the enlargement of local draining lymph nodes in the ipsilateral limb (Motulsky et al., "Lymph Nodes in Rheumatoid Arthritis," *AMA Arch Intern Med* 90(5):660-76 (1952); Cambiaggi G., "Lymph Nodes in Rheumatoid Arthritis; Lymph Node Hyperplasia of Symmers' Type in a Case of Still's Disease," *Progr Med* (Napoli) 10(16):488-91 (1954), which are hereby incorporated by reference in their entirety), indicating that the local lymphatic circulation from inflamed joints to draining lymph nodes may affect the progression of inflammatory processes. It is predictable that lymph from arthritic joints and surrounding tissues carries large amounts of cytokines and immune cells. When this inflammatory lymph reaches lymph nodes, it could stimulate lymphangiogenesis. Thus, inhibition of inflammation could reduce lymphangiogenesis. However, it is not clear whether or not lymphangiogenesis affects the natural progression of inflammation. This is an important distinction because accumulated evidence from animal models (Xing et al., "Lymphangiogenesis, Myeloid Cells and Inflammation," *Expert Rev Clin Immunol* 4(5):599-613 (2008); Zhang et al., "Increased Lymphangiogenesis in Joints of Mice with Inflammatory Arthritis," *Arthritis Res Ther* 9(6):R118 (2007); Baluk et al., "Pathogenesis of Persistent Lymphatic Vessel Hyperplasia in Chronic Airway Inflammation," *J Clin Invest* 115(2):247-57 (2005), which are hereby incorporated by reference in their entirety) and clinical studies (Paavonen et al., "Vascular Endothelial Growth Factors C and D and their VEGFR-2 and 3 Receptors in Blood and Lymphatic Vessels in Healthy and Arthritic Synovium," *J Rheumatol* 29(1):39-45 (2002); Wauke et al., "Expression and Localization of Vascular Endothelial Growth Factor-C in Rheumatoid Arthritis Synovial Tissue," *J Rheumatol* 29(1):34-8 (2002); Polzer et al., "Tumour Necrosis Factor Blockade Increases Lymphangiogenesis in Murine and Human Arthritic Joints," *Ann Rheum Dis* 67(11):1610-6 (2008), which are hereby incorporated by reference in their entirety) have demonstrated increased lymphangiogenesis in inflammatory tissues.

Both VEGF-A and VEGF-C signaling pathways have been implicated in inflammatory lymphangiogenesis (Shibuya et al., "Signal Transduction by VEGF Receptors in Regulation of Angiogenesis and Lymphangiogenesis," *Exp Cell Res* 312 (5):549-60 (2006), which is hereby incorporated by reference in its entirety). VEGFR-2 transduces signals in blood and lymphatic endothelial cells, while VEGFR-3 mediates signaling only in lymphatic endothelial cells. Thus, VEGFR-3 blockade affects lymphatics specifically (Pytowski et al., "Complete and Specific Inhibition of Adult Lymphatic Regeneration by a Novel VEGFR-3 Neutralizing Antibody," *J Natl Cancer Inst* 97(1): 14-21 (2005), which is hereby incorporated by reference in its entirety). VEGFR-3 neutralizing antibody treatment of TNF-Tg mice reduces the number and area of joint and PLN lymphatic vessels, but it significantly increases the severity of joint inflammation. Decreased lymphangiogenesis is accompanied by reduced or slower transport of the lymphatic tracer, ICG, from paws to PLNs and reduced clearance of ICG from paws and PLNs. These findings strongly indicate that adequate lymph drainage from inflamed paws to local draining lymph nodes plays a beneficial role in the inflammatory process. These findings are consistent with a recent report in which the same VEGFR-3 neutralizing antibody reduced the size of draining lymph nodes and increased lung weight, an outcome measure for lung inflammation, in a bacterial-induced airway inflammation model (Baluk et al., "Pathogenesis of Persistent Lymphatic Vessel Hyperplasia in Chronic Airway Inflammation," *J Clin Invest* 115(2):247-57 (2005), which is hereby incorporated by reference in its entirety). Thus sufficient lymphatic trafficking between the primary inflammation sites and local draining lymph nodes may play an important role limiting the progression of inflammation.

In contrast to VEGFR-3 blockage, VEGFR-2 neutralizing antibody significantly reduces both joint inflammation and lymphangiogenesis, indicating that VEGFR-2 and VEGFR-3 signal pathway have different mechanisms for reducing inflammatory lymphangiogenesis. VEGFR-2 blockade-induced reduction in lymphatics is likely indirect and is through its inhibitory effect on angiogenesis. VEGF-A or VEGFR-1 inhibition reduces joint damage in various models of arthritis (De Bandt et al., "Blockade of Vascular Endothelial Growth Factor Receptor I (VEGF-RI), but not VEGF-RII, Suppresses Joint Destruction in the K/BxN Model of Rheumatoid Arthritis," *J Immunol* 171(9):4853-9 (2003); Mould et al., "Prophylactic but not Therapeutic Activity of a Monoclonal Antibody that Neutralizes the Binding of VEGF-B to VEGFR-1 in a Murine Collagen-Induced Arthritis Model," (Oxford) 47(3): 263-6 (2008), which are hereby incorporated by reference in its entirety). However, a previous study reported no effects of VEGFR-2 neutralization on arthritis in K/BxN arthritic mice model (De Bandt et al., "Blockade of Vascular Endothelial Growth Factor Receptor I (VEGF-RI), but not VEGF-RII, Suppresses Joint Destruction in the K/BxN Model of Rheumatoid Arthritis," *J Immunol* 171(9):4853-9 (2003), which is hereby incorporated by reference in its entirety). The discrepancy between the present findings and the previous report may reflect differences in the animal models used. K/BxN mice develop severe and aggressive joint lesions around 4 weeks of age (Kyburz et al., "The KRN Mouse Model of Inflammatory Arthritis," *Springer Semin Immunopathol* 25(1):79-90 (2003); Korganow et al., "From Systemic T Cell Self-Reactivity to Organ-Specific Autoimmune Disease via Immunoglobulins," *Immunity* 10(4):451-61 (1999), which are hereby incorporated by reference in their entirety) and the disease is triggered following recognition of a NOD-derived MHC class II molecule by the transgenic TCR (Matsumoto et al., "Arthritis Provoked by Linked T and B Cell Recognition of a Glycolytic Enzyme," *Science* 286(5445):1732-5 (1999), which is hereby incorporated by reference in its entirety). The 3647 line of TNF-Tg line used in these studies develop arthritis at a much slower pace (Li et al., "Systemic Tumor Necrosis Factor Alpha Mediates an Increase in Peripheral CD11b-high Osteoclast Precursors in Tumor Necrosis Factor Alpha-Transgenic Mice," *Arthritis Rheum* 50(1):265-76 (2004), which is hereby incorporated by reference in its entirety), and TNF is the pathogenic mediator. Thus, VEGFR-2 inhibition may be more effective in chronic inflammatory arthritis.

CD11b$^+$ myeloid cells are the major source of VEGF-C in primary inflammatory sites and are responsible for promoting new lymphatic vessel formation. In PLNs of TNF-Tg mice the majority of CD11b$^+$ cells express VEGF-C, suggesting that VEGF-C in the lymph nodes is also produced by CD11b$^+$ myeloid cells. Currently, the origin of these CD11b$^+$ cells is not clear. They may migrate from the blood circulation or through afferent lymphatics from joints or both. The mechanisms that regulate the recruitment and retention of CD11b$^+$ cells in the PLNs are not known. The CCL19-CCL21/CCR7 axis is the major chemokine system expressed in the inflammatory lymphoid tissues and lymph nodes (Page et al., "Paired Synovium and Lymph Nodes from Rheumatoid Arthritis Patients Differ in Dendritic Cell and Chemokine Expression," *J Pathol* 204(1):28-38 (2004), which is hereby incorporated by reference in its entirety). CCL19/CCL21 is produced by non-hematopoietic stromal and fibroblast-like cells and attracts CCR7 expressing dendritic cells to the lymphoid tissues and lymph nodes (Manzo et al., "CCL21 Expression Pattern of Human Secondary Lymphoid Organ Stroma is Conserved in Inflammatory Lesions with Lymphoid Neogenesis," *Am J Pathol* 171(5):1549-62 (2007); Timmer et al., "Inflammation and Ectopic Lymphoid Structures in Rheumatoid Arthritis Synovial Tissues Dissected by Genomics Technology: Identification of the Interleukin-7 Signaling Pathway in Tissues with Lymphoid Neogenesis," *Arthritis Rheum* 56(8):2492-502 (2007), which are hereby incorporated by reference in their entirety). CD11b$^+$ cells are composed of dendritic cells and their precursors, thus whether or not the CCL19-CCL21/CCR7 axis is responsible for increased CD11b$^+$ cells in the TNF-Tg PLNs needs to be studied in the future. Furthermore, the chemokine, CXCR12, maintains the CD11b$^+$ hematopoietic cells in peripheral organs after they have been recruited from bone marrow by VEGF-A (Grunewald et al., "VEGF-Induced Adult Neovascularization: Recruitment, Retention, and Role of Accessory Cells," *Cell* 124(1): 175-89 (2006), which is hereby incorporated by reference in its entirety), and bone marrow derived CD11b$^+$ cells migrate along the CXCL12 gradient (Zhang et al., "TNF Inhibits Production of Stromal Cell-Derived Factor 1 by Bone Stromal Cells and Increases Osteoclast Precursor Mobilization from Bone Marrow to Peripheral Blood," *Arthritis Res Ther* 10(2):R37 (2008), which is hereby incorporated by reference in its entirety). In preliminary studies, CXCR12 mRNA levels are increased in TNF-Tg mouse PLNs compared to WT PLNS, suggesting that the CXCL12/CXCR4 axis may also be involved in retaining CD11b$^+$ cells in TNF-Tg PLNs.

Based on the current findings, a model to explain the importance of the lymphatic system in development and progression of inflammatory arthritis is proposed (FIG. 22). Joint inflammation recruits circulating CD11b$^+$ myeloid cells from circulation. These cells produce lymphatic growth factors, such as VEGF-C, to stimulate lymphatic vessel formation. The functional lymphatic vessels transport inflammatory lymph carrying inflammatory cells, catabolic factors and cytokines to the draining lymph nodes and promote lymphangiogenesis, leading to an expansion of the lymph nodes and dilation of lymphatic sinuses containing inflammatory cells. Thus, sufficient lymphatic drainage could limit the degree of joint inflammation and the manipulation of the lymphatic system may represent a novel therapy for inflammatory disorders.

Example 16

Administration of VEGF-C Reduces the Severity of Joint Lesions in Chronic Inflammatory Arthritic Mice by Enhancing Local Lymphatic Drainage Two major functions of the lymphatic system are removal of excess tissue fluid and the transfer of cells to local lymph nodes (LNs). Interestingly, the accumulation of interstitial fluid and cells is a major feature of synovitis in inflammatory-erosive arthritis (Tammela et al., "Molecular Lymphangiogenesis: New Players," *Trends Cell Biol* 15:434-41 (2005); and Alitalo et al., "Lymphangiogenesis in Development and Human Disease," *Nature* 438:946-53 (2005), which are hereby incorporated by reference in their entirety).

To test whether stimulation of lymphangiogenesis could have beneficial effects on arthritic joints, lymphangiogenesis was induced by over-expressing VEGF-C in the joints of TNF-Tg mice and its effect on synovial inflammation and vascularity, bone erosion, and lymphatic draining function from foot to local LNs were examined using an adeno-associated virus (AAV) delivery approach (Ito et al., "Remodeling of Cortical Bone Allografts Mediated by Adherent rAAV-RANKL and VEGF Gene Therapy," Nat Med 11:291-7 (2005), which is hereby incorporated by reference in its entirety). The exogenous administration of AAV-VEGF-C into the joints of TNF-Tg mice reduces the severity of joint lesions in chronic inflammatory arthritic mice by enhancing lymphatic drainage. This result indicates that the modification of lymphatic function may be a new therapy for chronic inflammatory arthritis.

VEGF-C is a potent lymphatic growth factor which stimulates lymphangiogenesis in multiple animal models (Yoon et al., "VEGF-C Gene Therapy Augments Postnatal Lymphangiogenesis and Ameliorates Secondary Lymphedema," J Clin Invest 111:717-25 (2003); and Hirakawa et al., "VEGF-C-Induced Lymphangiogenesis in Sentinel Lymph Nodes Promotes Tumor Metastasis to Distant Sites," Blood 109:1010-7 (2007), which are hereby incorporated by reference in their entirety). In these studies, VEGF-C was administrated in a form of recombinant or adenovirus encoded protein (Hirakawa et al., "VEGF-C-Induced Lymphangiogenesis in Sentinel Lymph Nodes Promotes Tumor Metastasis to Distant Sites," Blood 109:1010-7 (2007); and Saaristo et al., "Adenoviral VEGF-C Overexpression Induces Blood Vessel Enlargement, Tortuosity, and Leakiness but No Sprouting Angiogenesis in the Skin or Mucous Membranes," FASEB J 16:1041-9 (2002), which are hereby incorporated by reference in their entirety). Because the adenovirus itself causes inflammation and immune responses after 2-3 weeks of administration, these studies consisted of short term treatment protocols. Adeno-associated virus (AAV) (type 2) has previously been used successfully as a long term gene therapy approach in mice (Ito et al., "Remodeling of Cortical Bone Allografts Mediated by Adherent rAAV-RANKL and VEGF Gene Therapy," Nat Med 11:291-7 (2005); and Yang et al., "Adeno-Associated Virus-Mediated Osteoprotegerin Gene Transfer Protects Against Particulate Polyethylene-Induced Osteolysis in a Murine Model," Arthritis Rheum 46:2514-23 (2002), which are hereby incorporated by reference in their entirety). Thus, AAV expression vector was used to deliver VEGF-C to the joints of TNF-Tg mice. The pAAV-hVEGF-C (pAAV-VEGF-C) expression vector was generated by replacing the human VEGF-C cDNA for the OPG cDNA in pAAV-OPG (Yang et al., "Adeno-Associated Virus-Mediated Osteoprotegerin Gene Transfer Protects Against Particulate Polyethylene-Induced Osteolysis in a Murine Model," Arthritis Rheum 46:2514-23 (2002), which is hereby incorporated by reference in its entirety). Human VEGF-C was incorporated in the AAV vector, because it is fully functional in mouse tissues (Goldman et al., Overexpression of VEGF-C Causes Transient Lymphatic Hyperplasia but Not Increased Lymphangiogenesis in Regenerating Skin," Circ Res 96:1193-1199 (2005), which is hereby incorporated by reference in its entirety), an ELISA kit for measuring human VEGF-C is commercially available, and the same vector could be used later in human studies if lymphangiogenesis is proven to be important.

The pAAV-VEGF-C or pAAV-Luc expression vectors were transiently transfected into PlatE cells for 48 hours. The expression of VEGF-C mRNA (FIG. 23A) and protein in the whole cell lysate or in the conditioned medium (FIG. 23B) was assessed by real time RT-PCR or Western blot analysis. Both VEGF-C mRNA and protein expression levels were significantly increased in VEGF-C-transfected cells compared to Luciferase (Luc)-transfected cells. Three bands of different molecular sizes were detected in whole cell lysates (FIG. 23B), corresponding to the dimerized propeptide (~116 kD), propeptide (~58 kD) and secreted form of VEGF-C protein (29 kD) (Joukov et al., "Proteolytic Processing Regulates Receptor Specificity and Activity of VEGF-C," Embo J 16:3898-911 (1997), which is hereby incorporated by reference in its entirety). In conditioned medium, only the 29 kD secreted form of VEGF-C was detected. The 21 kD or 15 kD mature forms of VEGF-C protein were not observed. This indicates that the majority of VEGF-C protein produced by the AAV-VEGF-C virus is not in a mature form. Because mature forms of VEGF-C have higher affinity to VEGFR2 and affect angiogenesis (Joukov et al., "Proteolytic Processing Regulates Receptor Specificity and Activity of VEGF-C," Embo J 16:3898-911 (1997); and Saaristo et al., "Adenoviral VEGF-C Overexpression Induces Blood Vessel Enlargement, Tortuosity, and Leakiness but No Sprouting Angiogenesis in the Skin or Mucous Membranes," FASEB J 16:1041-9 (2002), which are hereby incorporated by reference in their entirety), it is expected that AAV-delivered VEGF-C will mainly bind to VEGFR3 and function in lymphatic endothelium cells.

The infection efficiency of AAV-VEGF-C virus was examined by infecting PlatE cells with various MOI of AAV-VEGF-C virus and AAV-Luc control virus as described previously (Yang et al., "Adeno-Associated Virus-Mediated Osteoprotegerin Gene Transfer Protects Against Particulate Polyethylene-Induced Osteolysis in a Murine Model," Arthritis Rheum 46:2514-23 (2002); and Ulrich-Vinther et al., "Recombinant Adeno-Associated Virus-Mediated Osteoprotegerin Gene Therapy Inhibits Wear Debris-Induced Osteolysis," J Bone Joint Surg Am 84:1405-12 (2002), which are hereby incorporated by reference in their entirety). AAV-VEGF-C-infected cells expressed very high levels of VEGF-C mRNA (FIG. 23C) and protein (FIG. 23D) in the conditioned medium. The 29 kD secreted form of VEGF-C was detected in the conditioned medium, similar to VEGF-C produced by pAAV-VEGF-C transfected cells. The expression level of VEGF-C protein in the conditioned medium was also assessed by an ELISA kit for detecting human VEGF-C (R&D Systems, Catalog # DVEC00). The VEGF-C protein levels were increased in a dose-dependent manner (FIGS. 23E-F).

Example 17

Assessment of the Duration of Intra-Articular Delivery of AAV Virus Encoded Genes In Vivo by Bioluminescent Images The AAV viral gene delivery method has been used in several murine disease models, such as polyethylene-induced osteolysis (Yang et al., "Adeno-Associated Virus-Mediated Osteoprotegerin Gene Transfer Protects Against Particulate Polyethylene-Induced Osteolysis in a Murine Model," Arthritis Rheum 46:2514-23 (2002), which is hereby incorporated by reference in its entirety) and bone allografts (Ito et al., "Remodeling of Cortical Bone Allografts Mediated by Adherent rAAV-RANKL and VEGF Gene Therapy," Nat Med 11:291-7 (2005), which is hereby incorporated by reference in its entirety). However, the longest duration of in vivo therapy in those models was 4 weeks. Since the TNF-Tg mouse is a chronic arthritis model, taking 2-3 months to observe clear joint lesions, it was necessary to determine over what period of time the AAV virus can be detected after injection to help guide proposed rAAV-VEGF-C therapy.

rAAV-Luc was injected into the left knee joints and the right quadriceps muscles of 2.5-month-old TNF-Tg mice (N=3). Bioluminescent (BL) images were taken at different times for up to 110 days thereafter (FIG. 24A) and luciferase signal intensity in the knee (FIG. 24B) and thigh muscle (FIG. 24C) was quantified. All other factors including f/stop, position of stage, binding ratio, and time after AAV-Luc injection were kept constant throughout the study. Animals were sacrificed on day 110 and luciferase activity in various tissues including spleen, liver, heart, lung, kidney, right and left of knee, ankle and quadriceps muscles was determined using a luciferase assay kit from Promega. High luciferase activity was detected in tissues of left knees and the right quadriceps muscles and all other tissues were luciferase negative (FIG. 24D). This indicates that AAV mediated gene expression is retained at the injected sites and does not enter systemic circulation. Further, high levels of AAV encoded gene expression can be maintained for at least 3 months in inflamed joints.

Example 18

Intra-Articular Injection of AAV-VEGF-C Reduces the Severity of Joint Lesions in Chronic Inflammatory Arthritic Mice by Enhancing Lymphatic Drainage As shown in Examples 12-14, blockade of lymphangiogenesis with VEGFR3 neutralizing antibody in TNF-Tg mice increases joint inflammation and decreases lymphatic drainage from foot to PLNs. This indicates that sufficient lymphatic flow plays a protective role during arthritis progression, and enhancement of lymphatic function may improve joint damage. To test this hypothesis, rAAV-VEGF-C was injected into knee and ankle joints of 1.5-month-old TNF-Tg mice, at a time when ankle, but not knee, inflammatory cell infiltration occurs, and lymphangiogenesis and VEGF-C expression are still relatively normal. This time point was used because it is similar to the clinical status of patients who have had the onset of joint lesions, but the disease is not advanced and inflammation-induced lymphangiogenesis has not occurred. Previous work has shown that joint damage in both ankle and knee joints progresses rapidly over the course of three months in TNF-Tg mice and increased joint lesions are associated with increased lymphangiogenesis and VEGF-C expression (Zhang et al., "Increased Lymphangiogenesis in Joints of Mice with Inflammatory Arthritis," *Arthritis Res Ther* 9:R118 (2007); Proulx et al., "Longitudinal Assessment of Synovial, Lymph Node, and Bone Volumes in Inflammatory Arthritis in Mice by In Vivo Magnetic Resonance Imaging and Microfocal Computed Tomography," *Arthritis Rheum* 56:4024-37 (2007); and Proulx et al., "MRI and Quantification of Draining Lymph Node Function in Inflammatory Arthritis," *Ann N Y Acad Sci* 1117:106-23 (2007), which are hereby incorporated by reference in their entirety). Accordingly, three months after rAAV-VEGF-C injection, VEGF-C expression at the injection sites was examined by RT-PCR. As expected, tissues isolated from AAV-hVEGF-C injection sites expressed human VEGF-C mRNA while the tissues that did not received AAV virus or received AAV-Luc control virus did not express human VEGF-C (FIG. 25A). In contrast, all tissues express murine VEGF-C (FIG. 25B). These data confirm the long term expression of AAV-hVEGF-C specifically in the injection sites.

During the three month period after AAV-VEGF-C injection, joint phenotype was monitored clinically. A clear difference in joint swelling and deformity was not observed between control virus and VEGF-C injected joints. However, the VEGF-C-injected joints were relatively easier to move. To examine this further, a clinical method of measuring joint flexibility was adapted. The knee or ankle joints that have received and expressed human VEGF-C (FIG. 26A) had a larger range of motion, demonstrating that those joints have better function than those that received the control AAV-Luc (FIG. 26B).

To examine the effect of AAV-VEGF-C on local lymphatic flow from foot to PLNs, the indocyanine green near infrared (ICG-NIR) lymphatic imaging method was used (FIG. 27). Compared to the AAV-Luc control injected legs (FIG. 27B), the ICG signal intensity of PLNs at one hour after ICG footpad injection was higher in legs that received AAV-VEGF-C virus (FIG. 27A), demonstrating that more ICG is transported to the PLNs through lymphatic vessels between feet and PLNs. Interestingly, the signal intensity of foot and PLN in the AAV-VEGF-C legs declined rapidly and was significantly lower than the AAV-Luc legs 24 hours after the ICG injection (compare FIGS. 27C-D). This indicates that more ICG was drawn away from the foot and PLNs through lymphatics, demonstrating that AAV-VEGF-C may stimulate lymphangiogenesis in joints and PLNs and improve the lymphatic drainage function locally.

Finally, the effect of VEGF-C over-expression on joint pathology was determined by histology analysis on H&E-stained sections. In control injected joints, serious synovitis and bone and cartilage destruction were observed in knee and ankle joints (FIGS. 28A, C), while in VEGF-C-injected joints these changes were significantly decreased (FIGS. 28B, D).

In summary, using the AAV-VEGF-C joint delivery method, stimulation of lymphangiogenesis at the early phase of chronic inflammatory arthritis significantly improved joint functions such as lymphatic drainage and the degree of joint movement. The VEGF-C over-expression reduced inflammation and bone and cartilage erosion. These data indicate that lymphatic circulation plays an important role during the progression of chronic inflammatory arthritis and the improvement in lymphatic function may represent a new therapy for patients with arthritis.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating an inflammatory joint condition in a patient comprising:
providing a therapeutic agent comprising a nucleic acid molecule encoding a vascular endothelial growth factor receptor-3 (VEGFR-3) agonist selected from the group consisting of VEGF-C protein or active fragment thereof, VEGF-C C152S mutant protein or active peptide fragment thereof, and VEGF-C C156S mutant protein or active peptide fragment thereof, wherein said nucleic acid molecule is operably linked to a promoter sequence that initiates expression of the VEGFR-3 agonist in an affected joint; and
administering the therapeutic agent directly to the affected joint of the patient having the inflammatory joint condition under conditions effective to initiate expression of the VEGFR-3 agonist in the joint, wherein said administering is effective to treat the inflammatory joint condition.

2. The method according to claim 1, wherein the inflammatory joint condition is a condition occurring around a joint.

3. The method according to claim 1, wherein the nucleic acid molecule is present in an expression vector.

4. The method according to claim 1 wherein the therapeutic agent is administered to the patient in combination with an agent that inhibits VEGF/VEGFR-1 or VEGF/VEGFR-2 signaling.

5. The method according to claim 4, wherein the agent is selected from the group consisting of a VEGFR-1 or VEGFR-2 antibody or aptamer; a VEGFR-1 or VEGFR-2 inhibitory peptide or polypeptide fragment; a polypeptide comprising a soluble VEGFR-1 or VEGFR-2 or fragment thereof; and a VEGF, VEGFR-1, or VEGFR-2 antisense polynucleotide or siRNA.

6. The method according to claim 1 wherein the therapeutic agent is administered to the patient in combination with an anti-inflammatory agent selected from the group consisting of a non-steroidal anti-inflammatory drug (NSAID), an analgesic, a glucocorticoid, a disease-modifying anti-rheumatic drug, a dihydrofolate reductase inhibitor, a TNFα inhibitor, a biologic response modifiers, and combinations thereof.

7. The method according to claim 1, wherein said administering is carried out intrasynovially or intra-articularly.

8. A method of treating a patient having an arthritic joint condition, the method comprising:
providing a therapeutic agent comprising a nucleic acid molecule encoding a vascular endothelial growth factor receptor-3 (VEGFR-3) agonist selected from the group consisting of VEGF-C protein or active fragment thereof, VEGF-C C152S mutant protein or active peptide fragment thereof, and VEGF-C C156S mutant protein or active peptide fragment thereof, wherein said nucleic acid molecule is operably linked to a promoter sequence that initiates expression of the VEGFR-3 agonist in an arthritic joint; and
administering the therapeutic agent directly to the arthritic joint of the patient having the arthritic condition under conditions effective to initiate expression of the VEGFR-3 agonist, wherein said administering is effective to treat the arthritic joint condition.

9. The method according to claim 8, wherein the arthritic condition is rheumatoid arthritis.

10. The method according to claim 8, wherein the arthritic condition is psoriatic arthritis.

11. The method according to claim 8, wherein the arthritic condition is inflammatory arthritis.

12. The method according to claim 8, wherein the arthritic condition is ankylosing spondylitis.

13. The method according to claim 8, wherein the nucleic acid molecule is present in an expression vector.

14. The method according to claim 8, wherein the therapeutic agent is administered to the patient in combination with an agent that inhibits VEGF/VEGFR-1 or VEGF/VEGFR-2 signaling.

15. The method according to claim 14, wherein the agent is selected from the group consisting of a VEGFR-1 or VEGFR-2 antibody or aptamer; a VEGFR-1 or VEGFR-2 inhibitory peptide or polypeptide fragment; a polypeptide comprising a soluble VEGFR-1 or VEGFR-2 or fragment thereof; and a VEGF, VEGFR-1, or VEGFR-2 antisense polynucleotide or siRNA.

16. The method according to claim 8, wherein the therapeutic agent is administered to the patient in combination with an anti-inflammatory agent selected from the group consisting of a non-steroidal anti-inflammatory drug (NSAID), an analgesic, a glucocorticoid, a disease-modifying anti-rheumatic drug, a dihydrofolate reductase inhibitor, a TNFα inhibitor, a biologic response modifiers, and combinations thereof.

17. The method according to claim 8, where said administering is effective to maintain joint function, reduce synovitis, inhibit bone destruction, and/or inhibit cartilage destruction.

18. The method according to claim 8, wherein the arthritic condition is osteoarthritis.

19. The method according to claim 1, wherein the inflammatory joint condition is a condition occurring in a joint.

20. A method of treating an inflammatory joint condition in a patient comprising:
 providing a therapeutic agent comprising an adenoviral vector, adeno-associated viral vector, retroviral vector, or plasmid vector, wherein said vector comprises a nucleic acid sequence encoding a vascular endothelial growth factor receptor-3 (VEGFR-3) agonist selected from the group consisting of VEGF-C protein or active fragment thereof, VEGF-C C152S mutant protein or active peptide fragment thereof, and VEGF-C C156S mutant protein or active peptide fragment thereof, wherein said nucleic acid sequence is operably linked to a promoter sequence that initiates expression of the VEGFR-3 agonist in an affected joint; and
 administering the therapeutic agent directly to the affected joint of the patient having the inflammatory joint condition under conditions effective to initiate expression of the VEGFR-3 agonist, wherein said administering is effective to treat the inflammatory joint condition.

21. The method according to claim 20, wherein the inflammatory joint condition is a condition occurring around a joint.

22. The method according to claim 20, wherein the inflammatory joint condition is a condition occurring in a joint.

23. The method according to claim 20, wherein the therapeutic agent is administered to the patient in combination with an agent that inhibits VEGF/VEGFR-1 or VEGF/VEGFR-2 signaling.

24. The method according to claim 20, wherein the agent is selected from the group consisting of a VEGFR-1 or VEGFR-2 antibody or aptamer; a VEGFR-1 or VEGFR-2 inhibitory peptide or polypeptide fragment; a polypeptide comprising a soluble VEGFR-1 or VEGFR-2 or fragment thereof; and a VEGF, VEGFR-1, or VEGFR-2 antisense polynucleotide or siRNA.

25. The method according to claim 20 wherein the therapeutic agent is administered to the patient in combination with an anti-inflammatory agent selected from the group consisting of a non-steroidal anti-inflammatory drug (NSAID), an analgesic, a glucocorticoid, a disease-modifying anti-rheumatic drug, a dihydrofolate reductase inhibitor, a TNFα inhibitor, a biologic response modifiers, and combinations thereof.

26. The method according to claim 20, wherein said administering is carried out intrasynovially or intra-articularly.

* * * * *